US006469047B1

(12) United States Patent
Jackson et al.

(10) Patent No.: US 6,469,047 B1
(45) Date of Patent: Oct. 22, 2002

(54) TYROSINE DERIVATIVES

(75) Inventors: David Y. Jackson, San Bruno, CA (US); Frederick C. Sailes, Stone Mountain, GA (US); Daniel P. Sutherlin, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 1 day.

(21) Appl. No.: 09/669,779

(22) Filed: Sep. 25, 2000

Related U.S. Application Data

(60) Provisional application No. 60/156,062, filed on Sep. 24, 1999.

(51) Int. Cl.$^7$ .................. A61K 31/535; A61K 31/40; C07D 403/00; C07D 471/10; C07D 295/00
(52) U.S. Cl. .............. 514/422; 514/235.8; 514/254.01; 514/291; 514/297; 514/298; 514/307; 514/322; 514/326; 514/423; 544/141; 544/372; 546/20; 546/146; 546/148; 546/208; 548/531
(58) Field of Search .................. 514/422, 423, 514/235.8, 254.01, 291, 297, 298, 307, 322, 326; 548/531; 544/141, 372; 546/146, 148, 20, 208

(56) References Cited

U.S. PATENT DOCUMENTS 4,278,793    7/1981    Durckheimer et al.

FOREIGN PATENT DOCUMENTS

WO    98 01133    *    1/1998

OTHER PUBLICATIONS

Barbadillo, C. et al. *Springer Semin. Immunopathol.* 16:375–379 (1995).

Laberge, S. et al., "Role of VLA–4 and LFA–1 in Allergen–Induced Airway Hyperresponsiveness and Lung Inflammation in the Rat" *Am. J. Respir. Crit. Care Med.* 151:822–829 (1995).

Podolsky, D.K., "Inflammatory Bowel Disease" *New England J. of Medicine* 325:928–937 (1991).

Powrie and Leach, "Genetic and Spontaneous Models of Inflammatory Bowel Disease in rodents: Evidence for Abnormalities in Mucosal Immune Regulation" *Ther. Immunol.* 2:115–123 (1995).

Viney et al., "Mucosal Addressin Cell Adhesion Molecule–1: A Structural and Functional Analysis Demarcates the Integrin Binding Motif" *J. Immunol.* 157:2488–2497 (1996).

* cited by examiner

*Primary Examiner*—D. Margaret Seaman
(74) *Attorney, Agent, or Firm*—David W Evans

(57) ABSTRACT

The compounds of the invention are inhibitors of alpha4 containing integrin-mediated binding to ligands such as VCAM-1 and MAdCAM.

18 Claims, No Drawings

TYROSINE DERIVATIVES

This application claims the benefit of provisional application No. 60/156,062 filed Sep. 24, 1999.

BACKGROUND OF THE INVENTION

The integrins are α/β heterodimeric cell surface receptors involved in numerous cellular processes from cell adhesion to gene regulation. Hynes, R. O., Cell, 1992, 69:11–25; HEMLEr, M. E., Annu. Rev. Immunol., 1990, 8:365–368. Several integrins have been implicated in disease processes and have generated widespread interest as potential targets for drug discovery. Sharar, S. R. et al., Springer Semin. Immunopathol., 1995, 16:359–378. In the immune system integrins are involved in leukocyte trafficking, adhesion and infiltration during inflammatory processes. Makajima, H. et al., J. Exp. Med., 1994, 179:1145–1154. Differential expression of integrins regulates the adhesive properties of cells and different integrins are involved in different inflammatory responses. Butcher, E. C. et al., Science, 1996, 272:60–66. The alpha4 integrins (i.e. alpha4beta1 (α4β1) and alpha4beta7 (α4β7)) are expressed primarily on monocytes, lymphocytes, eosinophils, basophils, and macrophages but not on neutrophils. Elices, M. J. et al., Cell, 1990, 60:577–584. The primary ligands for α4 integrins are the endothelial surface proteins mucosal addressin cell adhesion molecule (MAdCAM) and vascular cell adhesion molecule (VCAM) with lower affinity. Makarem, R. et al., J. Biol. Chem., 1994, 269:4005–4011. The binding of the α4β7 or α4β1 to MAdCAM and/or VCAM expressed on high endothelial venules (HEVs) at sites of inflammation results in firm adhesion of the leukocyte to the endothelium followed by extravasation into the inflamed tissue. Chuluyan, H. E. et al., Springer Semin. Immunopathol., 1995, 16:391–404. Monoclonal antibodies directed against α4β1, α4β7, MAdCAM or VCAM have been shown to be effective modulators in animal models of chronic inflammatory diseases such as asthma (Laberge, S. et al., Am. J. Respir. Crit. Care Med., 1995, 151:822–829), Rheumatoid arthritis (RA; Barbadillo, C. et al., Springer Semin. Immunopathol., 1995, 16:375–379), colitis (Viney et al, J. Immunol., 1996, 157: 2488–2497) and inflammatory bowel diseases (IBD; Podalski, D. K., N. Eng. J. Med., 1991, 325:928–937; Powrie, F. et al., Ther. Immunol., 1995, 2:115–123).

A need exists for non-protein small molecule compounds which inhibit the interaction between the α4β7 integrin and its ligands MAdCAM and/or VCAM. These compounds are useful for treatment of chronic inflammatory diseases such as arthritis, asthma, multiple sclerosis, Crone's disease, ulcerative colitis, and Hepatitis C.

SUMMARY OF THE INVENTION

Accordingly, the present invention relates to new compounds of the formula I, II or III:

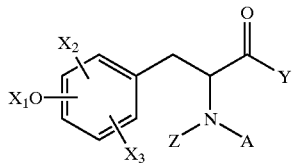

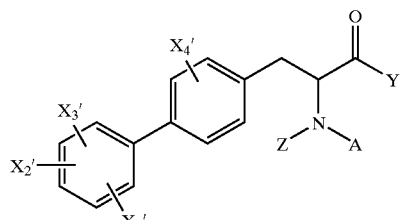

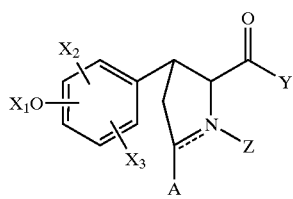

wherein
Z is H or lower alkyl;
A has the structure:

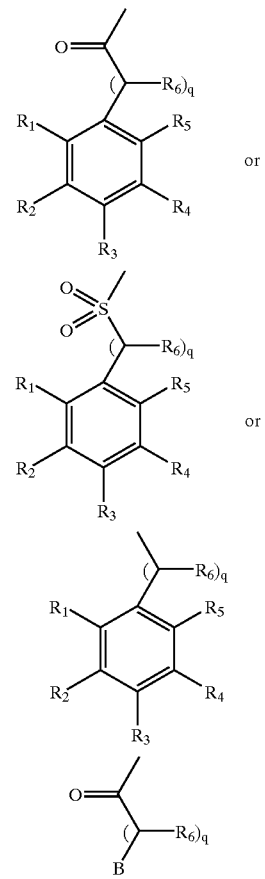

in which
B is cyanoalkyl, a carbocycle or a heterocycle optionally substituted with one or more $R_1$ substituents;
q is 0–3;
$R_1$, $R_2$, $R_3$, $R_4$, $R_5$ and $R_6$ independently are hydrogen, alkyl, amino, alkylamino, dialkylamino, nitro, urea, cyano, thio, alkylthio, hydroxy, alkoxy, alkoxyalkyl, alkoxycarbonyl, alkoxycarbonylamino, aryloxycarbonylamino, alkylsulfinyl, sulfonyl, alkylsulfonyl, aralkylsulfonyl, arylsulfonyl, heteroarylsulfonyl, alkanoyl, alkanoylamino, cycloalkanoylamino, aryl, arylalkyl, halogen, or alkylphosphonyl, and $R_1$, $R_2$, $R_3$, $R_4$ and $R_5$ are substituted with 0–3 substituents selected from the group consisting of hydroxy, carboxyl, lower alkoxycarbonyl, lower alkyl, nitro, oxo, cyano, carbocycyl, heterocyclyl, heteroaryl, lower alkylthio, lower alkoxy, lower alkylamino, lower alkanoylamino, lower alkylsulfinyl, lower sulfonyl, lower alkylsulfonyl, lower alkanoyl, aryl, aroyl, heterocyclylcarbonyl, halogen and lower alkylphosphonyl; or two of $R_1$ to $R_5$ together form a carbocycle or heterocyclic ring;

Y is H, alkoxy, alkoxyalkoxy, aryloxy, alkylaminoalkoxy, dialkylaminoalkoxy, alkylamino, arylamino, heterocyclyl or heteroarylalkyl, where each of the forgoing may be substituted or unsubstituted;

$X_1$ is H, C(O)OR, C(O)NRaRb, C(O)R, or C(O)SR wherein R, Ra and Rb, individually, is hydrogen or alkyl, alkoxy, aryl, heterocyclyl, heteroaryl, substituted with 0–4 substituents selected from the group consisting of halogen, hydroxy, amino, carboxyl, nitro, cyano, heterocyclyl, heteroaryl, aryl, aroyl, aryloxy, aralkyl, aralkyloxy, aryloxycarbonyl, aralkyloxycarbonyl, alkylenedioxy, lower alkoxycarbonyl, lower alkyl, lower alkenyl, lower alkynyl, lower alkylthio, lower alkoxy, lower alkylamino, lower alkylsulfinyl, lower sulfonyl, lower alkylsulfonyl, lower alkanoyl, lower alkylphosphonyl, aminosulfonyl lower alkyl, hydroxy lower alkyl, alkylsulfinyl lower alkyl, alkylsulfonyl lower alkyl, alkylthio lower alkyl, heteroarylthio lower alkyl, heteroaryloxy lower alkyl, heteroarylamino lower alkyl, halo lower alkyl, and alkoxy lower alkyl; wherein said heterocyclyl, heteroaryl, aryl, aroyl, aryloxy, aralkyl, aralkyloxy, aryloxycarbonyl and aralkyloxycarbonyl is optionally substituted with halogen, hydroxyl, amino, carboxyl, nitro, cyano, alkyl and alkoxy; and wherein Ra and Rb together with the nitrogen to which they are attached may form a heterocyclyl or heteroaryl group substituted with 0–5 substituents R or Rd; wherein Rd has the structure

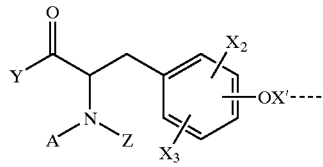

wherein

X' is a divalent linker selected from the group consisting of C(O)NRa, C(O) or a bond;

$X_2$ and $X_3$ are each independently hydrogen, halogen, hydroxy, amino, carboxyl, nitro, cyano, or substituted or unsubstituted alkyl, aryl, heterocylyl, heteroaryl, aryl, aroyl, aryloxy, alkylenedioxy, lower alkyl carbonylamino, lower alkenyl carbonylamino, aryl carbonylamino, arylalkyl carbonylamino, lower alkoxy carbonylamino, lower alkylamino carbonylamino, arylamino carbonylamino, lower alkoxycarbonyl, lower alkyl, lower alkenyl, lower alkynyl, lower alkylthio, lower alkoxy, lower alkylamino, lower alkylsulfinyl, lower sulfonyl, lower alkylsulfonyl, lower alkanoyl, lower alkylphosphonyl, aminosulfonyl lower alkyl, hydroxy lower alkyl, alkylsulfinyl lower alkyl, alkyl-sulfonyl lower alkyl, alkylthio lower alkyl, heteroarylthio lower alkyl, heteroaryloxy lower alkyl, heteroarylamino lower alkyl, halo lower alkyl, alkoxy lower alkyl; and wherein $X_1$ and $X_2$ or $X_3$ may be bonded together to form a heterocylic or heteroaryl ring(s); or $X_3$ and Z together form a heterobicyclic ring;

$X_{1'}$, $X_{2'}$, $X_{3'}$ and $X_{4'}$ are each independently hydrogen, halogen, hydroxy, amino, carboxyl, nitro, cyano, or substituted or unsubstituted alkyl, alkenyl, alkynyl, arylalkyl, heterocylyl, heteroaryl, aryl, aroyl, aryloxy, alkylenedioxy, lower alkyl carbonylamino, lower alkenyl carbonylamino, aryl carbonylamino, arylalkyl carbonylamino, lower alkoxy carbonylamino, lower alkylamino carbonylamino, arylamino carbonylamino, lower alkoxycarbonyl, lower alkyl, lower alkenyl, lower alkynyl, lower alkylthio, lower alkoxy, lower alkylamino, lower alkylsulfinyl, lower sulfonyl, lower alkylsulfonyl, lower alkanoyl, lower alkylphosphonyl, aminosulfonyl lower alkyl, hydroxy lower alkyl, alkylsulfinyl lower alkyl, alkylsulfonyl lower alkyl, alkylthio lower alkyl, heteroarylthio lower alkyl, heteroaryloxy lower alkyl, heteroarylamino lower alkyl, halo lower alkyl, alkoxy lower alkyl;

or a pharmaceutically acceptable salt thereof.

These compounds inhibit the binding of α4β7 or α4β7 to MAdCAM and/or VCAM. The invention also relates to methods of making such compounds, compositions and medicaments containing the compounds and to methods of inhibiting the binding of α4β7 or α4β1 to MAdCAM and/or VCAM and to treating diseases associated with this binding.

DETAILED DESCRIPTION OF THE PREFERRED EMBODIMENTS

A. Definitions:

The term "alkyl", used alone or as part of another term, for example alkylamino, alkylsulfonyl, alkylthio, etc., means a branched or unbranched, saturated or unsaturated aliphatic hydrocarbon group, having the number of carbon atoms specified, or if no number is specified, having up to and including 12 carbon atoms. "Alkyl" when used alone or as part of another term preferably means a saturated hydrocarbon chain, however also includes unsaturated hydrocarbon carbon chains such as "alkenyl" and "alkynyl". Examples of alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$–$C_6$ alkyl" and "alkyl of 1 to 6 carbon atoms" are synonymous and used interchangeably. Preferred "$C_1$–$C_6$ alkyl" groups are methyl, ethyl, 1-propyl, isopropyl, 1-butyl or sec-butyl.

The term "substituted alkyl" or "substituted $C_n$–$C_m$ alkyl" where m and n are integers identifying the range of carbon atoms contained in the alkyl group, denotes the above alkyl groups that are substituted by one, two, three or four halogen, trifluoromethyl, hydroxy, unsubstituted and substituted $C_1$–$C_7$ alkoxy, protected hydroxy, amino (including alkyl and dialkyl amino), protected amino, unsubstituted and substituted $C_1$–$C_7$ acyloxy, unsubstituted and substituted $C_3$–$C_7$ heterocyclyl, unsubstituted and substituted phenoxy, nitro, carboxy, protected carboxy, unsubstituted and substituted carboalkoxy, unsubstituted and substituted acyl, carbamoyl, carbamoyloxy, cyano, methylsulfonylamino, unsubstituted and substituted benzyloxy, unsubstituted and substituted $C_3$–$C_6$ carbocyclyl or $C_1$–$C_4$ alkoxy groups. The substituted alkyl groups may be substituted once (preferably), twice or three times with the same or with different substituents.

Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl gropu may also be substituted with a carbocyclyl group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. A preferred group of examples within the above group includes the substituted methyl group, e.g. a methyl group substituted by the same substituent as the "substituted $C_n$–$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

The term "alkoxy" denotes groups having the number of carbon atoms specified such as methoxy, ethoxy, n-propoxy, isopropoxy, n-butoxy, t-butoxy and like groups. The term "substituted alkyl" means these alkoxy group substituted by the same substituents as the "substituted alkyl" group.

The term "acyloxy" denotes carboacyloxy groups having the specified number of carbon atoms such as formyloxy, acetoxy, propionyloxy, butyryloxy, pentanoyloxy, hexanoyloxy, heptanoyloxy, and the like. The term "substituted acyloxy" means these acyloxy groups substituted by the same substituents as the "substituted alkyl" group.

The term "alkylcarbonyl", "alkanoyl" and "acyl" are used interchangeably herein encompass groups having the specified number of carbon atoms such as formyl, acetyl, propionyl, butyryl, pentanoyl, hexanoyl, heptanoyl, benzoyl and the like.

The term "alkylsulfonyl" denotes the groups —NH—$SO_2$-alkyl, —$SO_2$—N-alkyl, —N—($SO_2$-alkyl)$_2$ and —$SO_2$—N(alkyl)$_2$. Preferred alkylsulfonyl groups are —NH—$SO_2$—Me, —NO—$SO_2$—Et, —NH—$SO_2$—Pr, —NH—$SO_2$—iPr, —N—($SO_2$—Me)$_2$ and —N—($SO_2$—Cu)$_2$.

The term "amino" denotes primary (i.e. —$NH_2$), secondary (i.e. —RNH) and tertiary (i.e. —NRR) amines. Preferred secondary and tertiary amines are alkylamine and dialkyl amines such as methylamine, ethylamine, proylamine, isopropylamine, dimethylamine, diethylamine, dipropylamine and disopropylamine.

The terms "carbocyclyl", "carbocyclic" and "carbocyclo" alone and when used as a moiety in a complex group such as a carbocycloalkyl group, refers to a mono-, bi-, or tricyclic aliphatic ring having 3 to 14 carbon atoms and preferably 3 to 7 carbon atoms. Preferred carbocyclic groups include cyclopropyl, cyclobutyl, cyclopentyl and cyclohexyl groups. The terms "substituted carbocyclyl" and "carbocyclo" means these groups substituted by the same substituents as the "substituted alkyl" group.

A "carbocycloalkyl" group is a carbocyclo group as defined above covalently bonded to an alkyl group as defined above.

The term "alkenyl" means a branched or unbranched hydrocarbon group having the number of carbon atoms designated containing one or more carbon-carbon double bonds, each double bond being independently cis, trans, or a nongeometric isomer. The term "substituted alkenyl" means these alkenyl groups substituted by the same substituents as the "substituted alkyl" group.

The term "alkynyl" means a branched or unbranched hydrocarbon group having the number of carbon atoms designated containing one or more carbon-carbon triple bonds. The term "substituted alkynyl" means these alkynyl groups substituted by the same substituents as the "substituted alkyl" group.

The terms "alkylthio" and "$C_1$–$C_{12}$ substituted alkylthio" denote $C_1$–$C_{12}$ alkyl and $C_1$–$C_{12}$ substituted alkyl groups, respectively, attached to a sulfur which is in turn the point of attachment for the alkylthio or substituted alkylthio group to the group or substituent designated.

An "alkylenedioxy" group is a —O-alkyl-O— group, where alkyl is as defined above. Preferred alkylenedioxy groups are methylenedioxy and ethylenedioxy.

The term "aryl" when used alone or as part of another term means a homocyclic aromatic group whether or not fused having the number of carbon atoms designated or if no number is designated, up to 14 carbon atoms. Preferred aryl groups include phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]).

The term "aroyl" means an aryl group bonded to a carbonyl, such as benzoyl, etc.

The term "substituted phenyl" or "substituted aryl" denotes a phenyl group or aryl group substituted with one, two, three, four or five, preferably 1–2, 1–3 or 1–4 substituents chosen from halogen (F, Cl, Br, I), hydroxy, protected hydroxy, cyano, nitro, alkyl (preferably $C_1$–$C_6$ alkyl), alkoxy (preferably $C_1$–$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or methyne (CH) and/or methylene ($CH_2$) groups in these substituents may in tern be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, ; a mono- or di(hydroxymethyl)phenyl or (protected hydroxymethyl) phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl)

phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Preferred substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl) benzyloxy-phenyl, 3-methoxy-4-(1-chloromethyl) benzyloxy-6-methyl sulfonyl aminophenyl groups. Also, the term "substituted phenyl" represents phenyl groups having an aryl, phenyl or heteroaryl group fused thereto. The fused ring may also be substituted with any, preferably 1, 2 or 3, of the substituents identified above for "substituted alkyl" groups.

The term "arylalkyl" means one, two, or three aryl groups having the number of carbon atoms designated, appended to an alkyl group having the number of carbon atoms designated including but not limited to; benzyl, napthylmethyl, phenethyl, benzhydryl (diphenylmethyl), trityl, and the like. A preferred arylalkyl group is the benzyl group.

The term "substituted arylalkyl" denotes an alkyl group, preferably a $C_1$–$C_6$alkyl group, substituted at any carbon with an aryl group, preferably a $C_6$–$C_{10}$aryl group, bonded to the alkyl group though any aryl ring position and substituted on the alkyl portion with one, two or three groups chosen from halogen (F, Cl, Br, I), hydroxy, protected hydroxy, amino, protected amino, $C_1$–$C_7$acyloxy, nitro, carboxy, protected carboxy, carbamoyl, carbamoyloxy, cyano, $C_1$–$C_6$alkylthio, N-(methylsulfonylamino) or $C_1$–$C_4$alkoxy. Optionally the aryl group may be substituted with one, two, three, four or five groups chosen from halogen, hydroxy, protected hydroxy, nitro, $C_1$–$C_6$alkyl, $C_1$–$C_6$alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the $C_1$–$C_6$ alkyl portion or the aryl portion or both are disubstituted, the substituents can be the same or different. This group may also appear as the substituted aralkyl moiety of a substituted aralkoxy group.

Examples of the term "substituted aralkyl" and this group when it occurs in a "substituted aralkoxy" group include groups such as 2-phenyl-1-chloroethyl, 1-phenyl-1-chloromethyl, 1-phenyl-1-bromomethyl, 2-(4-methoxyphenyl)ethyl, 2,6-dihydroxy-4-phenyl(n-hexyl), 5-cyano-3-methoxy-2-phenyl(n-phenyl), 3-(2,6-dimethylphenyl)n-propyl, 4-chloro-3-aminobenzyl, 6-(4-methoxyphenyl)-3-carboxy(n-hexyl), 5-(4-aminomethyl phenyl)-3-(aminomethyl)(n-phenyl), and the like.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl) methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the allyl and p-nitrobenzyl groups. Similar carboxy-protecting groups used in the cephalosporin, penicillin and peptide arts can also be used to protect a carboxy group substitutents. Further examples of these groups are found in T. W. Greene and P. G. M. Wuts, "Protective Groups in Organic Synthesis", 2nd ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley & Sons, New York, N.Y., 1981, Chapter 5. The term "protected carboxy" refers to a carboxy group substituted with one of the above carboxy-protecting groups.

The term "hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, acetoxy, carbamoyloxy, trifluoro, chloro, carboxy, bromo and iodo groups. Further examples of these groups are found in T. W. Greene and P. G. M. Wuts, "Protective Groups in Organic Synthesis", 2nd ed., John Wiley & Sons, Inc., New York, N.Y., 1991, chapters 2–3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley & Sons, New York, N.Y., 1981. The term "protected hydroxy" refers to a hydroxy group substituted with one of the above hydroxy-protecting groups.

The term "amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino"

refers to an amino group substituted with one of the above amino-protecting groups.

The term "inhibitor" means a compound which reduces or prevents the binding of an alpha4beta1 integrin to a VCAM-1 ligand or reduces or prevents the binding of an alpha4beta7 integrin to a MAdCAM-1 ligand or which reduces or prevents the initiation of a cellular response mediated by the ligand. An "effective amount" is an amount is an amount sufficient to at least partially inhibit the binding and and may be an inhibitory amount.

The terms "heterocyclic group", "heterocyclic", "heterocyclyl", or "heterocyclo" alone and when used as a moiety in a complex group such as a heterocycloalkyl group, are used interchangeably and refer to any mono-, bi-, or tricyclic saturated or non-aromatically unsaturated ring having the number of atoms designated, generally from 3 to about 10 ring atoms, where the ring atoms are carbon and 1,2,3 or 4 nitrogen, sulfur or oxygen atoms. Typically, a 5-membered ring has 0 to 2 double bonds and 6- or 7-membered ring has 0 to 3 double bonds and the nitrogen or sulfur heteroatoms may optionally be oxidized, and any nitrogen heteroatom may optionally be quaternized. Examples include morpholinyl, pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperidinyl, and 3,4,5,6-tetrahydropiperidinyl. A preferred group is the morphilinyl group.

A "heterocycloalkyl" or a "heterocycloalkenyl" group is a heterocyclo group as defined above covalently bonded to an alkyl or alkenyl group as defined above.

Unless otherwise specified, "heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and preferably at least one heteroatom is nitrogen (*Lang's Handbook of Chemistry*, supra). Included in the definition are any bicyclic groups where any of the above heteroaryl rings are fused to a benzene ring. Heteroaryls in which nitrogen or oxygen is the heteroatom are preferred.

The following ring systems are example of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl.

Heterocyclic 5-membered ring systems containing a sulfur or oxygen atom and one to three nitrogen atoms are also suitable for use in the instant invention. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. A preferred group of examples of benzo-fused derivatives are benzoxazol-2-yl, benzthiazol-2-yl and benzimidazol-2-yl.

Further suitable specific examples of the above heterocylic ring systems are 6-membered ring systems containing one to three nitrogen atoms and optionally a sulfur or oxygen atom. Such examples include pyridyl, such as pyrid-2-yl, pyrid-2-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a preferred group. The substituents for the optionally substituted heterocyclic ring systems, and further examples of the 5- and 6-membered ring systems discussed above can be found in W. Druckheimer et al., U.S. Pat. No. 4,278,793.

A particularly preferred group of "heteroaryl" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodiums salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl.

An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-dimethylamino)eth-2-yl-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

The term "lower" when used with a term such as alkyl to form "lower alkyl", for example, means containing from 1 to 6 carbon atoms.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The term "prodrug" as used herein means a derivative of a parent drug molecule that enhances pharmaceutically desirable characteristics or properties (e.g. transport, bioavailability, pharmacodynamics, etc.) and that requires biotransformation, either spontaneous or enzymatic, within the organism to release the active parent drug.

The following definitions are used herein:

DIPC: diisopropylcarbodiimide
DMAP: dimethylaminopyridine
FMOC: fluorenylmethoxycarbonyl
DMA: dimethylacetamide
HBTU: 2-(H-benzotriazole)-1-yl-1,1,3,3-tetramethyluronium hexafluorophosphate
HOBT: N-hydroxy benzotriazole
TFA: trifluoracetic acid
HPLC: high pressure liquid chromatography
NMM: N-methylmorpholine
DIPEA: diisopropyethylamine
DCM: dichloromethane
THF: tetrahydrofuran
NMP: N-methylpyrolidone
CDI: carbonyldiimidazole

B. PREFERRED EMBODIMENTS

The compounds of the invention have the general structures I, II and III shown below.

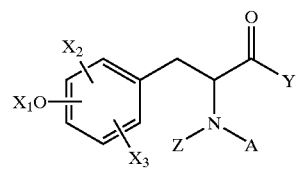

I

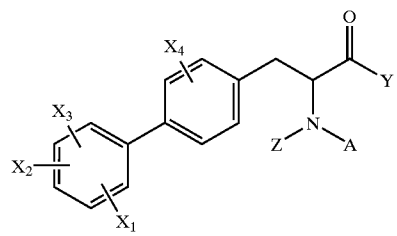

II

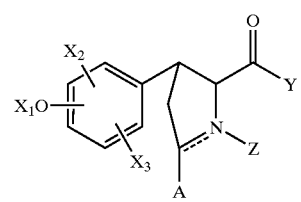

III where A, Z, Y, $X_1$, $X_2$, $X_3$ and $X_4$ are as defined above, both generally and preferably.

The compounds of the invention contain one or more asymmetric carbon atoms. Accordingly, the compounds may exist as diasteriomers, enantiomers or mixtures thereof. The syntheses described above may employ racemates, diasteriomers or enantiomers as starting materials or as intermediates. Diasteriomeric compounds may be separated by chromatographic or crystallization methods. Similarly, enatiomeric mixtures may be separated using the same techniques or other known in the art. Each of the asymmetric carbon atoms may be in the R or S configuration and both of these configurations are within the scope of the invention. Compounds having the S configuration are preferred.

In one preferred embodiment, $X_1$ in structure I is C(O) OR, C(O)R, or C(O)SR, more preferably C(O)NRaRb, with the remaining variables A, Z, Y, $X_2$, $X_3$ and $X_4$ having any of the definitions given above. The $X_1$ group is preferably in the para position relative to the point of ring attachment, but may also be preferably in the meta position. Ra and Rb together with the nitrogen to which they are attached may preferably form a 5-membered or 6-membered heterocyclyl or heteroaryl group substituted with 0–5 substituents R. The heterocyclyl or heteroaryl ring system will preferably contain one nitrogen atom, but may also preferably contain another nitrogen or an oxygen atom in the ring system. The hetero ring systems may contain fused heterocyclyl or heteroaryl rings or a combination of both and the rings may be substituted or unsubstituted. Representative examples of suitable specific heterocyclyl and heteroaryl groups are:

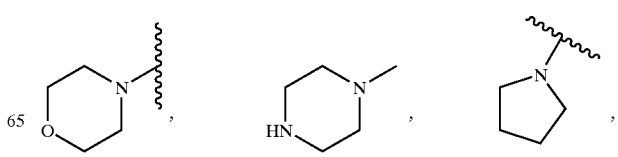

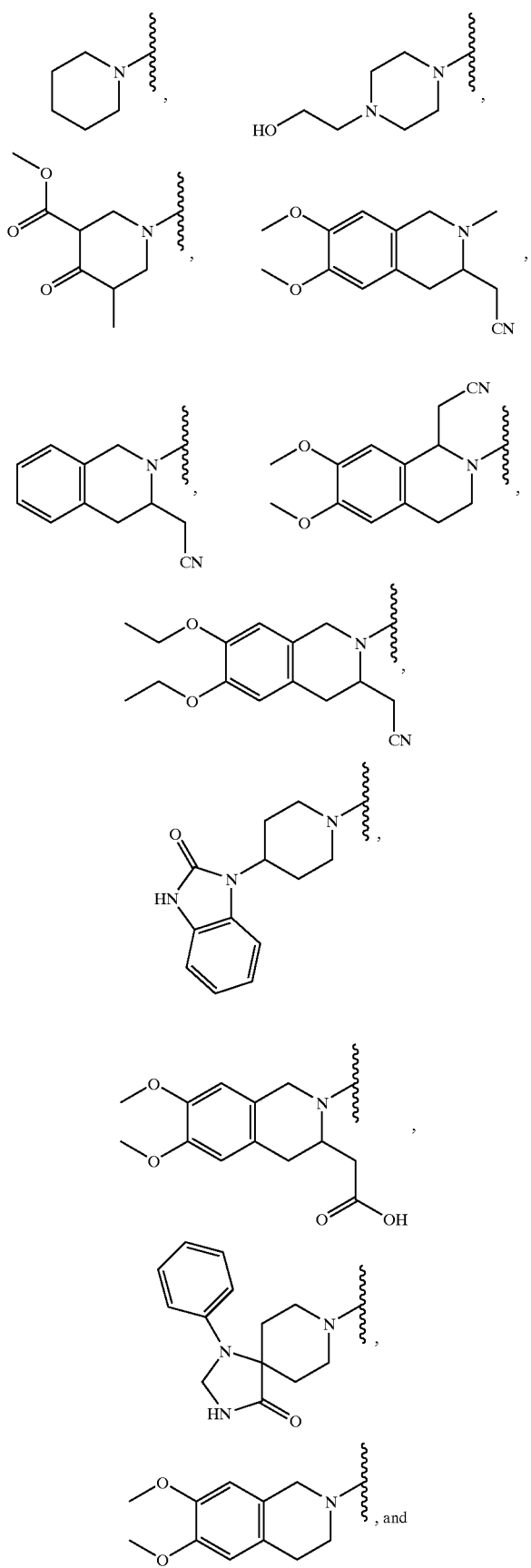

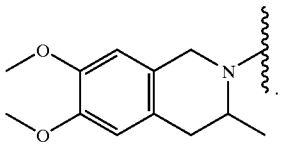

In a particular embodiment, $X_1$ is any one of the groups shown in table 2 below which is designated as substituent R when combined with the carbonyl from which it depends.

R, Ra and Rb may also be non-cyclic, for example an hydrogen or alkyl, aryl, heterocyclyl, heteroaryl, substituted with 0–4 substituents selected from the group consisting of halogen, hydroxy, amino, carboxyl, nitro, cyano, heterocylyl, heteroaryl, aryl, aroyl, aryloxy, alkylenedioxy, lower alkoxycarbonyl, lower alkyl, lower alkenyl, lower alkynyl, lower alkylthio, lower alkoxy, lower alkylamino, lower alkylsulfinyl, lower sulfonyl, lower alkylsulfonyl, lower alkanoyl, lower alkylphosphonyl, aminosulfonyl lower alkyl, hydroxy lower alkyl, alkylsulfinyl lower alkyl, alkylsulfonyl lower alkyl, alkylthio lower alkyl, heteroarylthio lower alkyl, heteroaryloxy lower alkyl, heteroarylamino lower alkyl, halo lower alkyl, alkoxy lower alkyl; optionally substituted as described above. Preferred groups are substituted and unsubstituted lower alkyl, lower alkenyl, aryl, and aryl lower alkyl. Some representative examples of such R, Ra and Rb groups are shown below:

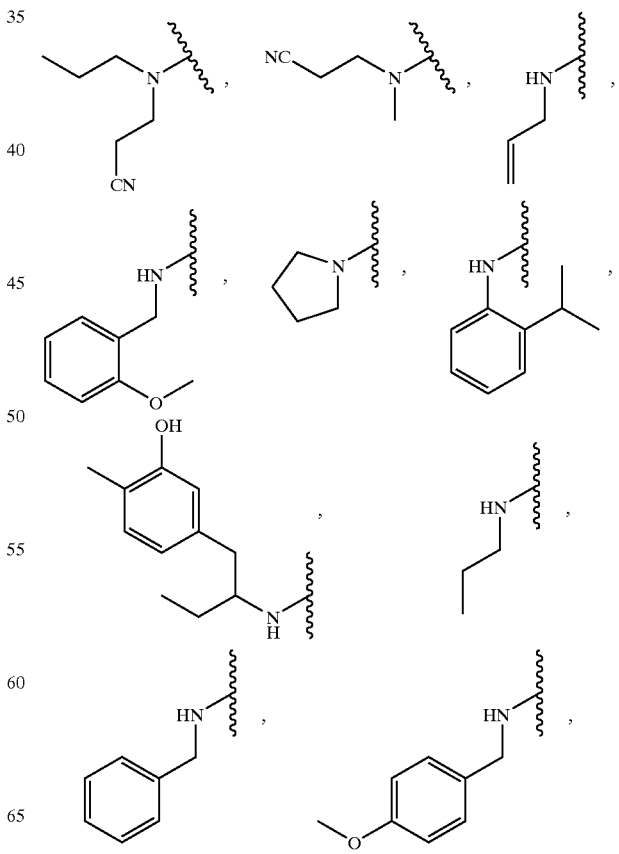

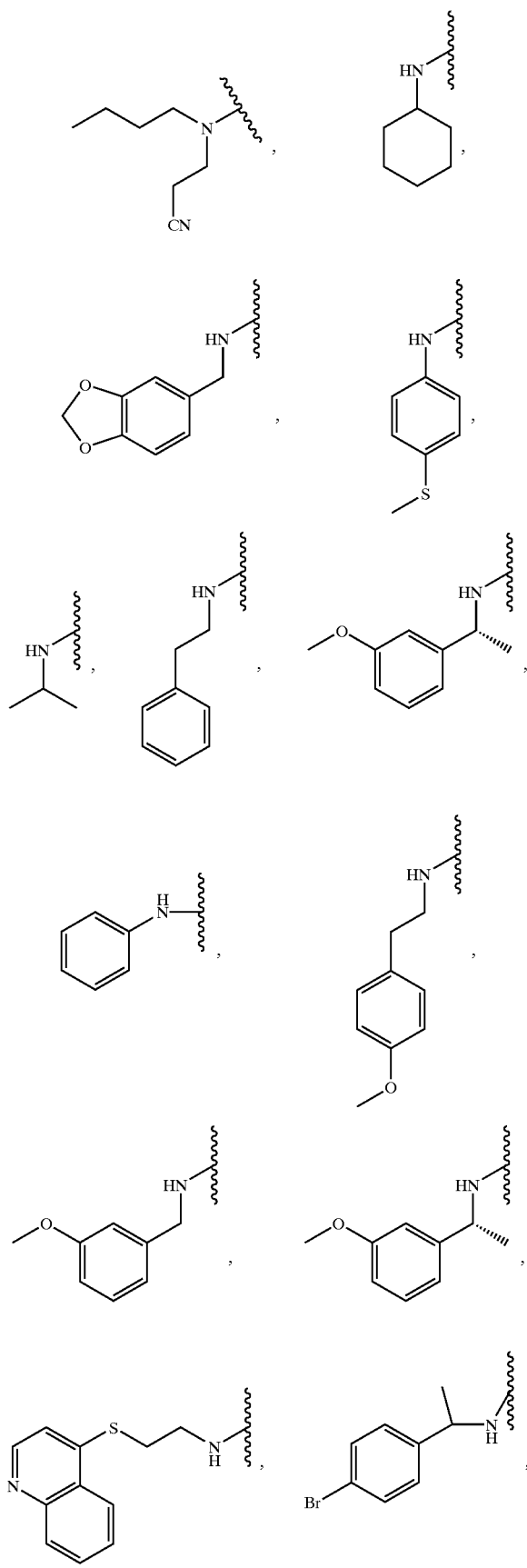

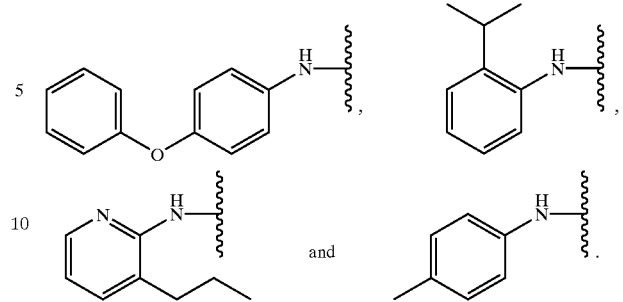

In a particular embodiment, A has the structure:

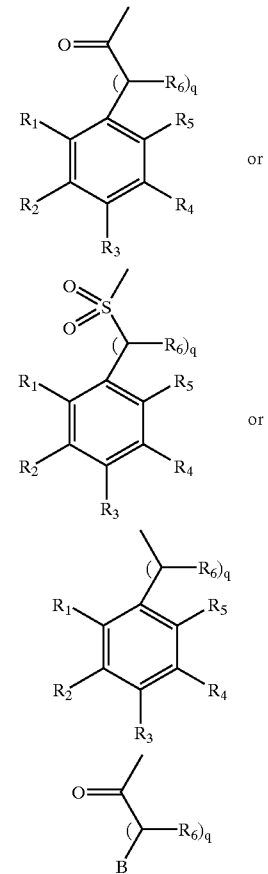

in which
B is cyanoalkyl, a carbocycle or a heterocycle optionally substituted with one or more $R_1$ substituents;
q is 0–3;
$R_1$, $R_2$, $R_3$, $R_4$, $R_5$ and $R_6$ independently are hydrogen, alkyl, amino, alkylamino, dialkylamino, nitro, urea, cyano, thio, alkylthio, hydroxy, alkoxy, alkoxyalkyl, alkoxycarbonyl, alkoxycarbonylamino, aryloxycarbonylamino, alkylsulfinyl, sulfonyl, alkylsulfonyl, aralkylsulfonyl, arylsulfonyl, heteroarylsulfonyl, alkanoyl, alkanoylamino, cycloalkanoylamino, aryl, aralkyl, halogen, or alkylphosphonyl, and $R_1$, $R_2$, $R_3$, $R_4$ and $R_5$ are substituted with 0–3 substituents selected from the group consisting of hydroxy, carboxyl, lower alkoxycarbonyl, lower alkyl, nitro, oxo, cyano, carbocyclyl, heterocyclyl, heteroaryl, lower alkylthio, lower alkoxy, lower alkylamino, lower alkanoylamino, lower alkylsulfinyl, lower sulfonyl, lower alkylsulfonyl, lower alkanoyl, aryl, aroyl, heterocyclylcarbonyl, halogen and lower alkylphosphonyl; or two of $R_1$ or $R_5$ together form a carbocycle or heterocyclic ring. In a preferred embodiment, A is the group

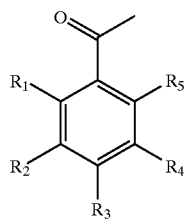

where preferably $R_1$, $R_5$ or both $R_1$ and $R_5$ are not hydrogen. That is, preferred A groups are ortho-substituted benzoyl groups. Particularly preferred ortho substituents are chloro, bromo, amino and hydroxy. In addition to $R_1$ and/or $R_5$, the phenyl ring of the benzoyl may preferably have one or two additional substituents at $R_2$, $R_3$ or $R_4$. Preferred $R_1$, $R_2$, $R_3$ $R_4$, and $R_5$ include nitro, halogen (Cl, Br, F, I), amino, aryl, lower alkyl, lower alkylthio, lower alkoxy, lower alkylamino, lower alkyl sulfinyl, lower alkylsulfonyl, lower alkanoyl, and lower alkylphosphonyl, which may each be substituted or unsubstituted. Some representative example include:

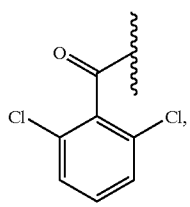 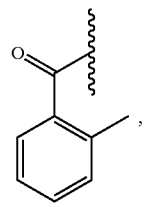 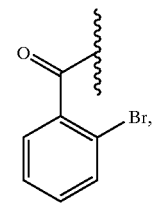

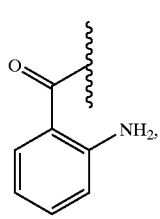 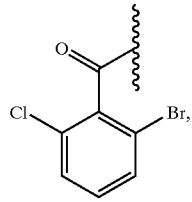 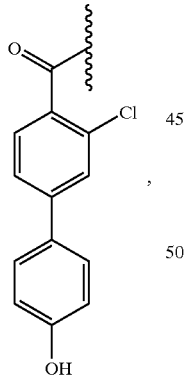

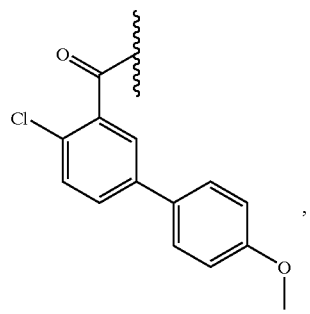 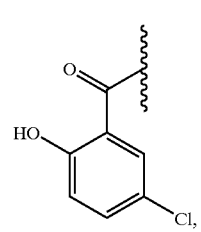

-continued

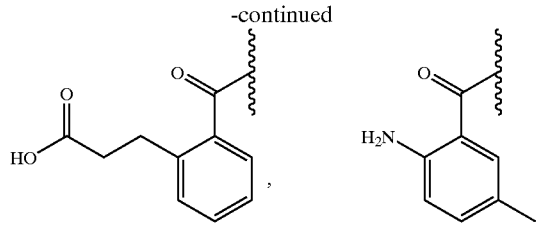

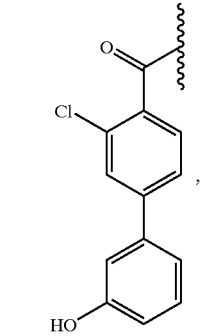

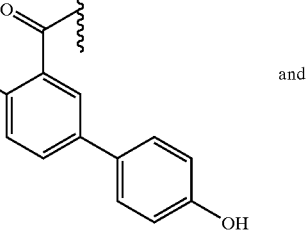

and

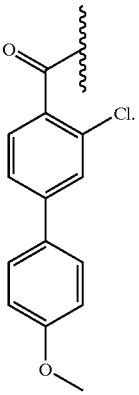

In a particular embodiment, A is any one of the groups shown in table 2 which is designated as substituent R'.

Y is preferably OH or an ester or pharmaceutically acceptable carboxylic acid salt thereof. Preferred esters are substituted or unsubstituted alkyl, alkenyl, aryl, and aryl alkyl esters.

Z is preferably hydrogen.

Preferred $X_2$, $X_3$ and $X_4$ include halogen, alkyl, amino, alkylamino, and alkyl carbonylamino, the alkyl group of which may be substituted or unsubstituted. For compounds having structure I, $X_2$ and $X_3$ are more preferably hydrogen. For compounds having structure II, $X_2$, $X_3$ and $X_4$ are more preferably hydrogen.

In another embodiment, preferred compounds have structure I, the S configuration, the $OX_1$ group is in the 4-position on the phenyl ring, Z is hydrogen, $X_1$ is C(O)NRaRb, and Y is OH or a salt or prodrug thereof.

In another embodiment, preferred compounds have structure I, the S configuration, the $OX_1$ group is in the 4-position on the phenyl ring, Z is hydrogen, $X_1$ is C(O)NRaRb, Y is OH, and $R_3$, $R_5$, $X_2$, and $X_3$ are all hydrogen or a salt or prodrug thereof.

In another embodiment, preferred compounds have structure I, the S configuration, the $OX_1$ group is in the 4-position on the phenyl ring, Z is hydrogen, $X_1$ is C(O)NRaRb, Y is OH, Ra and Rb together with the nitrogen atom to which they are attached form a substituted or unsubstituted 5-membered or 6-membered heterocyclic or heteroaromatic ring; $R_3$, $R_5$, $X_2$, and $X_3$ are all hydrogen, or a salt or prodrug thereof.

In another embodiment, preferred compounds have structure I, the S configuration, the $OX_1$ group is in the 4-position on the phenyl ring, Z is hydrogen, $X_1$ is C(O)NRaRb, Y is OH, Ra and Rb together with the nitrogen atom to which they are attached form a substituted or unsubstituted 5-membered or 6-membered heterocyclic ring containing up to 2 additional nitrogen atoms, oxygen atoms or a combination thereof; $R_2$, $R_3$ $R_4$, $R_5$, $X_2$, and $X_3$ are all hydrogen, or a salt or prodrug thereof.

In another embodiment, preferred compounds have structure I, the S configuration, the $OX_1$ group is in the 4-position on the phenyl ring, Z is hydrogen, $X_1$ is C(O)NRaRb, Y is OH, Ra and Rb together with the nitrogen atom to which they are attached form an unsubstituted 5-membered or 6-membered heterocyclic ring or such a ring substituted with 1–3 lower alkoxy, lower alkylamino, lower alkyl, lower alkoxycarbonyl, lower alkylenedioxy, lower alkylthio, lower alkenyl, lower cyanoalkyl, phenyl, phenoxy or halo groups; $R_2$, $R_3$ $R_4$, $R_5$, $X_2$, and $X_3$ are all hydrogen, or a salt or prodrug thereof.

In another embodiment, preferred compounds have structure I, the S configuration, the $OX_1$ group is in the 4-position on the phenyl ring, Z is hydrogen, $X_1$ is C(O)NRaRb, Y is OH Ra and Rb, are independently, substituted or unsubstituted alkyl, aryl, arylalkyl, heterocylyl, heteroaryl, heterocyclylalkyl, heteroarylalkyl or cycloalkylalkyl; $R_3$, $R_5$, $X_2$, and $X_3$ are all hydrogen, or a salt or prodrug thereof.

In another embodiment, preferred compounds have structure I, the S configuration, the $OX_1$ group is in the 4-position on the phenyl ring, Z is hydrogen, $X_1$ is C(O)NRaRb, Y is OH, Ra and Rb, are independently, substituted or unsubstituted alkyl, aryl, arylalkyl, heterocylyl, heteroaryl, heterocyclylalkyl, heteroarylalkyl or cycloalkylalkyl; $R_2$, $R_3$, $R_4$, $R_5$, $X_2$, and $X_3$ are all hydrogen, or a salt or prodrug thereof.

C. USES

The compounds of the invention inhibit the binding of alpha4beta1 and alpha4beta7 on lymphocytes, eosinophiles, basophiles and monocytes to a cell expressing VCAM-1 and/or MAdCAM on the cell surface. The inhibitory compounds of the invention are useful to prevent the interaction of an epithelial cell bearing VCAM-1 and/or MAdCAM on the cell surface with a leukocyte cell bearing alpha4beta1 and/or alpha4beta7 on the surface by contacting the epithelial cell or the leukocyte with an inhibitory amount of the compound of the invention. The compounds are useful in assays to determine the inhibitory effect of a compound which antagonizes the binding of alpha4beta1 and/or alpha4beta7 integrin to VCAM-1 ligand and/or MAdCAM ligand. The inhibitory compound may be a small molecule, a protein or peptide or an antibody. In an in vitro assay, the ligand or the integrin may be directly or indirectly bound to a surface, such as microtiter plate, using known methods described for example in WO 9820110, WO 9413312, WO 9624673, WO 9806248, WO 9936393, and WO 9910312. The other member of the binding pair, e.g. the integrin or the ligand, respectively, (or a cell expressing the same on its surface) is then added to the surface bound member and the inhibitory effect of a test molecule is determined. The inhibitory activity of the compounds of the invention can also be determined with this type of assay.

The binding of the integrins to their respective ligands is known to be involved in inflammatory conditions associated with leukocyte infiltration of tissues lined with epithelial cells expressing VCAM-1 or MAdCAM. Such tissues include the gastrointestinal tract, skin, urinary tract, respiratory airways and joint synovial tissues. The compounds of the invention are useful in treating diseases in which such binding is implicated as a cause of the disease or symptoms of the disease. Undesired disease symptoms may arise from cell adhesin and/or cell activation which releases proinflammatory mediators, typically when there is an increase or upregulation in the expression of VCAM-1 and/or MAdCAM on the surface of endothelial cells. Various disease states which can be treated and for which the inflammatory symptoms can be reduced upon administration of the compounds of the invention include rheumatoid arthritis, asthma, psoriasis, multiple sclerosis, inflammatory bowel disease including ulcerative colitis, pouchitis and Chron's disease, Celiac disease, nontropical Sprue, graft-versus-host pancreatitis, insulin-dependent diabetes mellitus, mastitis, cholecystitis, pericholangitis, chronic sinusitis, chronic bronchitis, pneumonitis, collagen disease, eczema, and systemic lupus erythematosis. The compounds of the invention are useful in treating these diseases and conditions by inhibiting the integrin/ligand binding.

The compounds of the invention can be assayed for ability to block the alpha4beta7/MAdCAM-1 or alpha4beta1/VCAM-1 binding interaction by addition of serial dilutions of the samples to plates with the receptors as follows. 96-well plates are coated with mouse anti-human alpha4 (31470D, PharMingen, San Diego, Calif.) The plates are decanted and blocked with 0.5% BSA. After washing $alpha_4beta_7$ or $alpha_4beta_1$ is added, followed by incubation for 2 h at room temperature. The plates are washed and samples of the small molecule antagonist are added to the plates with MAdCAM-1-Ig-HRP or VCAM-1-Ig-HRP for 2 h at room temperature. After an additional wash, the bound MAdCAM-1Ig-HRP or VCAM-1-Ig HRP is detected by addition of tetramethylbenzidine (TMB, Kirkegaard & Perry, Gaithersberg, Md.), followed by detection of the absorbance of the product.

Alternatively, the compounds can be assayed using any known protein-protein or cell-based assay method, such as those described, for example, in WO 99/10312 (examples 179–180) and WO 99/36393 (RPMI-CS-1 cell adhesion assay); Cardarelli et al., 1994, J. Biol. Chem, 269:18668–18673; and Viney et al., J. Immunol., 1996, 157:2488–2497 (cell adhesion assay).

For example, 96-well ELISA plates are coated overnight at 4° C. with 2 µg/ml with anti-human CD49d, (31470D, PharMingen, San Diego, Calif.) in phosphate buffered saline. The plates are decanted and blocked with assay buffer (50 mM Tris-HCl, pH 7.5, 150 mM NaCl, 1 mM $MnCl_2$, 0.05% Tween-20 and 0.5% BSA) at room temperature for one hour, with gentle shaking. The plates are washed three times (in 50 mM Tris-HCl, pH 7.5, 100 mM NaCl, 1 mM $MnCl_2$, 0.05% Tween-20) and 2 µg/ml of the desired integrin (Genentech, Inc.) in assay buffer is added, followed by incubation at room temperature for two hours, with gentle shaking. After washing three times, 50 µl of samples of the small molecule antagonists (serial dilutions from 10 mM stocks in 100% DMSO) are added to the plates with 50 µl of 1 µg/ml MAdCAM-1-Ig-HRP or VCAM-1-Ig-HRP (Genetech, Inc) in assay buffer. The plates are incubated two hours at room temperature, with gentle shaking, followed by washing six times. The bound MAdCAM-1-Ig-HRP or VCAM-1-Ig-HRP is detected by addition of the peroxidase substrate, 3, 3', 5, 5', tetramethylbenzidine (TMB, Kirkegaard & Perry, Gaithersberg, Md.), for 10 minutes, followed by addition of 1M phosphoric acid to stop the reaction. The absorbance of the solutions are read at 450 nm on a plate reader.

Suitable animal models exist for many diseases and conditions which can be treated with the compounds of the invention. Additional confirmation of the efficacy of these compounds in specific diseases and at desired doses can be assayed using these established models. For example animal models of chronic inflammatory diseases such as asthma (Laberge, S. et al., Am. J. Respir. Crit. Care Med., 1995, 151:822–829.), rheumatoid arthritis (RA; Barbadillo, C. et al., Springer Semin. Immunopathol., 1995, 16:375–379), colitis (Viney et al, J. Immunol., 1996, 157: 24488–2497) and inflammatory bowel diseases (IBD; Podalski, D. K., N. Eng. J. Med., 1991, 325:928–937; Powrie, F. et al., Ther. Immunol., 1995, 2:115–123) may be used to demonstrate the activity of the compounds of the invention and to conduct dose and efficacy studies.

The invention also includes pharmaceutical compositions or medicaments containing the compounds of the invention and a therapeutically inert carrier or excipient, as well as methods of using the compounds of the invention to prepare such compositions and medicaments. Typically, the inhibitors used in the method of this invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to prevent, ameliorate, or treat the alpha4 mediated disorder. Such amount is preferably below the amount that is toxic to the host or renders the host significantly more susceptible to severe infection.

As a general proposition, the initial pharmaceutically effective amount of the inhibitor administered parentally per dose will be in the range of about 0.01–100 mg/kg, preferably about 0.1 to 20 mg/kg of patient body weight per day, with the typical initial range of compound used being 0.3 to 15 mg/kg/day. Oral unit dosage forms, such as tablets and capsules, preferably contain from about 25 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration.

An example of a suitable oral dosage form is a tablet containing 25 mg, 50 mg, 100 mg, 250 mg, or 500 mg of the compound of the invention compounded with about 90–30 mg anhydrous lactose, about 5–40 mg sodium croscarmellose, about 5–30 mg polyvinylpyrrolidone (PVP) K30, and about 1–10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5–400 mg, if the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

D. METHODS OF MAKING

Synthesis of Acyltyrosine Compounds (I)

I. Solid phase synthesis:

The compounds of invention are prepared from tyrosine and tyrosine derivatives using known chemical reactions and according to the method shown below.

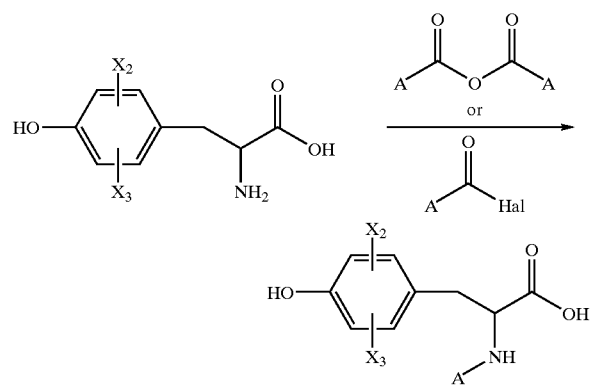

In this method, the amino group of tyrosine or a derivative thereof is reacted with an acyl halide of the formula ZC(O) Hal, where Hal is a halogen, preferably Cl or Br, or an acyl anhydride of the formula ZC(O)OC(O)Z to acylate the amino nitrogen atom. Typically, the reaction conditions are dilute base in a suitable solvent, for example bicarbonate in water/THF. Other suitable mild bases and solvents/solvent mixtures will be readily apparent to those having ordinary skill in organic synthesis. Numerous starting tyrosine derivatives are commercially available or can be readily synthesized using standard chemical reactions. An example of the synthesis of a compound within the scope of the invention is shown below.

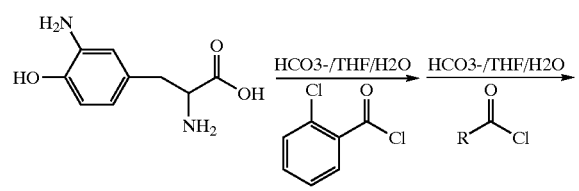

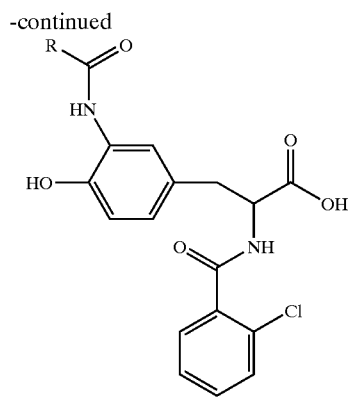

In this scheme, R may be any suitable group which is non-reactive under the reaction conditions. Examples of suitable R groups include substituted and unsubstituted alkyl, alkenyl, aryl, arylalkyl, etc. Additional compounds of the invention can then be prepared by acylating the phenyl hydroxy group with an activated carbonyl followed by the formation of a carbamate, carbonate or thiocarbamate as described below.

Solid phase reaction chemistry provides a convenient method for synthesizing the compounds of the invention. FMOC— or BOC— protected amino acids and derivatives thereof are readily available and can be used as starting materials in the synthesis of the compounds of the invention. The protected amino acid is initially attached to a synthetic resin having an available coupling group, such as an available hydroxy (e.g. benzyloxy resin beads). Coupling is achieved using known chemical reactions, e.g. condensation reactions using for example DIPC or DMAP, to attach the amino acid to the solid support. Any known coupling reactions and resin surfaces may be used. The amino nitrogen is then deprotected using, for example, a weak base such as piperidine or other suitable base. The free amino group can then be reacted with an activated ester such a HBTU or HOBT ester of a suitable benzoic acid to form the desired A group. The resulting hydroxy compounds are within the scope of the invention.

Additional compounds can be prepared by further reacting the hydroxy group to form esters, carbamates, carbonates, etc. using known chemistry. For example, the hydroxy compounds can be reacted with a carbonyl synthon such as phosgene, carbonyldiimidazole or p-nitrophenylformate followed by a primary or secondary amine, including cyclic amines, to form carbamates as shown in the reaction scheme below.

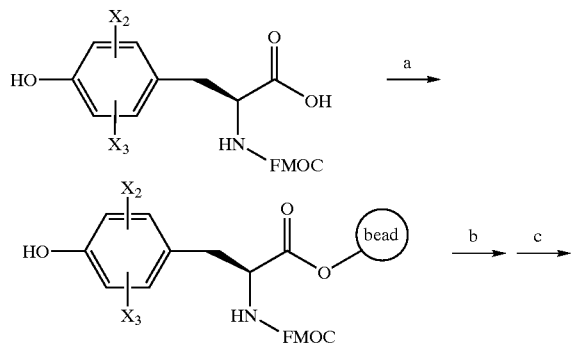

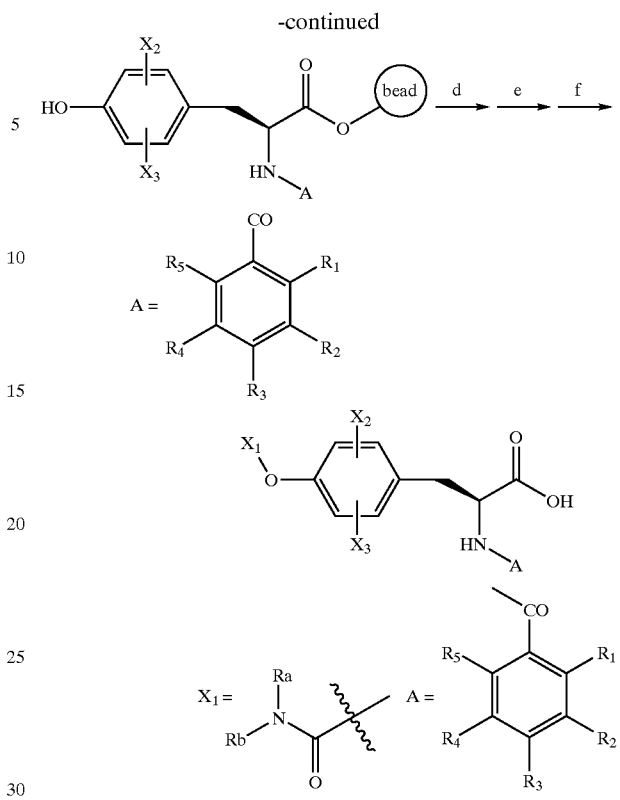

In this scheme, a=DIPC cat./DMAP; b=20% piperidine/DMA or DMF; c=a substituted benzoid acid/HBTU or other amide coupling agent/TEA or other weak base; d=primary or secondary amine; e=TFA/triethylsilane, for example.

Compounds of structure I were typically synthesized manually via solid phase synthesis on p-alkoxybenzyl alcohol resin (Advanced Chemtech, USA) as shown above. Commercially available FMOC protected tyrosine or other tyrosine analogs (X2/X3) were purchased from BACHEM Calif., Advanced ChemTech U.S.A., or Calbiochem Corp. (Calif.). Typically 1 mmol of FMOC-tyrosine (or tyrosine analog) was added to 1 g of p-alkoxybenzylalcohol resin in 50 mL dichloromethane. Diisopropylcarbodiimide (DIPC, 1 mmol) was added followed by catalytic dimethylaminopyridine (DMAP, 0.1 mmol) and the resulting mixture was stirred under nitrogen at 20C. for 4 hours. The resin was then washed with dicloromethane and dimethylacetamide (DMA) and the FMOC group was removed via mixing with 20% piperidine in DMA for fifteen minutes. The resin was then washed three times with DMA to remove excess piperidine.

Ortho-Chlorobenzoic acid (2 mmol) or other substituted benzoic acid was mixed with HBTU (2 mmol) or other suitable activating agent in 20 mL of DMA and added the previously washed resin. N-methylmorpholine or triethylamine (4 mmol) was added and the mixture was sparged with nitrogen for 30 minutes. The resin was washed with dichloromethane and treated with 2 mmol of p-nitrophenylchloroformate (phosgene or carbonyldiimidazole can also be used) and 0.05 mmol DMAP in 20 mL of DMA for 1 h. Excess reagents were washed away and 2 mmol of morpholine or other substituted amine RaRb-NH in 20 mL dichloromethane was added. The mixture was sparged overnight at room temperature and washed with dichlormethane.

Treatment with RFA containing 5% triethylsilane for 1 hour afforded the crude product. The crude material was extracted from the resin by stirring with 100 mL of 2:1 H₂O/CH₃CN for 5 minutes followed by filtration to remove the resin. The crude filtrate was lyophilized and purified by preparative reverse phase $C_{18}$ HPLC (CH₃CN/H₂O gradient, 0.1% TFA) to afford purified material. Pure fractions (>98% pure by analytical HPLC) were characterized by electrospray ionization mass spectrometry (Sciex API100) and proton NMR, lyophilized to dryness and resuspended in DMSO at 10 mM just prior to biological assay. Serial dilutions of peptide starting at 0.5 mM were tritrated into an ELISA format assay and the $IC_{50}$ for each compound was determined.

II. Solution phase synthesis:

Alternatively, inhibitors with general structure I can be synthesized in three steps via solution phase chemistry starting with commercially available (L)-tyrosine or tyrosine analogs having substituents at X2/X3 and/or Y. A general synthesis of type I Analogs is depicted below. This type of synthesis is amenable to scale up and for introducing ester prodrugs.

Typically, 100 mmols of (L)-tyrosine or similar tyrosine analog is dissolved in 500 mL THF/H20 (1:1) and 300 mmols of sodium bicarbonate is added followed by 110 mmols (1.1 eq.) of a suitable benzoyl chloride or anhydride of general structure Z-COCI. The solution is stirred at room temperature for 1 h. The mixture is concentrated via rotary evaporation and acidified to pH< 3 with 1 N HCL. The acidified solution is extracted with ethyl acetate and the organic layer is washed with satd. NaCl and evaporated to dryness. Crystallization of the crude material from ethylacetate/hexane affords pure compound as determined by analytical HPLC (average yield; 75 mmol or 75%).

If a suitable benzoyl chloride or anhydride is not available then the corresponding substituted benzoic acid (100 mmols) is used in combination with HBTU or other amide coupling reagent. If this route is employed, 100 mmols of (L)-tyrosine or similar tyrosine analog is dissolved in 250 Ml of dimethylformamide. In a separate vessel, the appropriate benzoic acid (110 mmols) in DMF is mixed with 110 mmols of HBTU or other amide coupling agent and 300 mmols of triethylamine or other weak base (NMM, DIPEA etc.). The mixture is allowed to stand for 10 minutes and then added to the tyrosine in one portion. After stirring for 1 hour at room temperature, the reaction mixture is concentrated under high vacuum and resuspended in ethyl acetate. The suspension is washed with 1 N HCL, water and satd. NaCl and evaporated to dryness. Crystallization affords pure compound (average yield; 66 mmol or 66%).

Purified 2 (50 mmols) is dissolved in 400 mL of THF and 100 mmols of TEA (or other base) is added followed by 50 mmol of p-nitrophenylchloroformate (phosgene or carbonyldiimidazole can also be used). The reaction is stirred for 1 hour at room temp, filtered and the filtrate is concentrated to dryness to afford crude compound which can be isolated via crystallization form ethyacetate/hexane or used directly in the next step. If phosgene or CDI is used instead of p-nitrophenylchloroformate then isolation at this stage is not an option and an appropriate amine RaRb-NH is added to the above reaction 30 minutes after the addition of p-nitrophenylchloroformate.

The p-nitrophenylcarbonate (10 mmol is dissolved in 100 ml to THF, 15 mmol of an appropriate amine RaRb-NH is added, and the reaction is stirred overnight at room temp. The solvent is evaporated and the resulting residue is tritrated with hexane to remove by products. Crystallization affords the desired O-carbamoyl-N-acyltyrosine inhibitor.

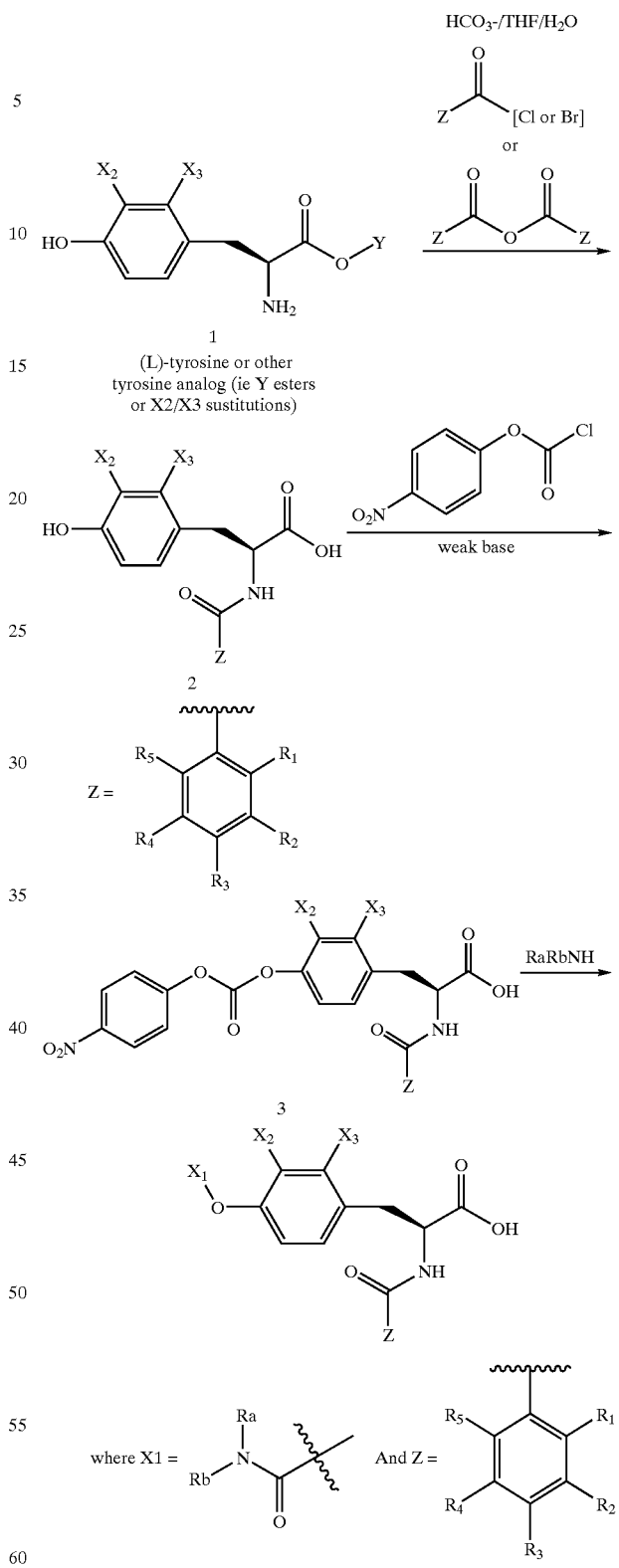

Synthesis of Biphenylalanine Compounds (II).

The biphenyl compounds of structure II can be synthesized starting from substituted or unsubstituted halo phenylalanine compounds as shown below. The protected amino acid starting material can be coupled to a resin as described above or using any known resin/coupling reaction system known in the art. The biphenyl ring system can then be prepared by reacting the halo amino acid with a substituted or unsubstituted phenyl boronic acid. If desired, a substituent on one of the phenyl rings may then be further elaborated using known chemical reactions. For example, a substituent containing a nitrogen atom can be further modified to provide amides, carbamates, etc. A substituent having a hydroxy or carboxy group can be converted to an ester, carbonate, etc.

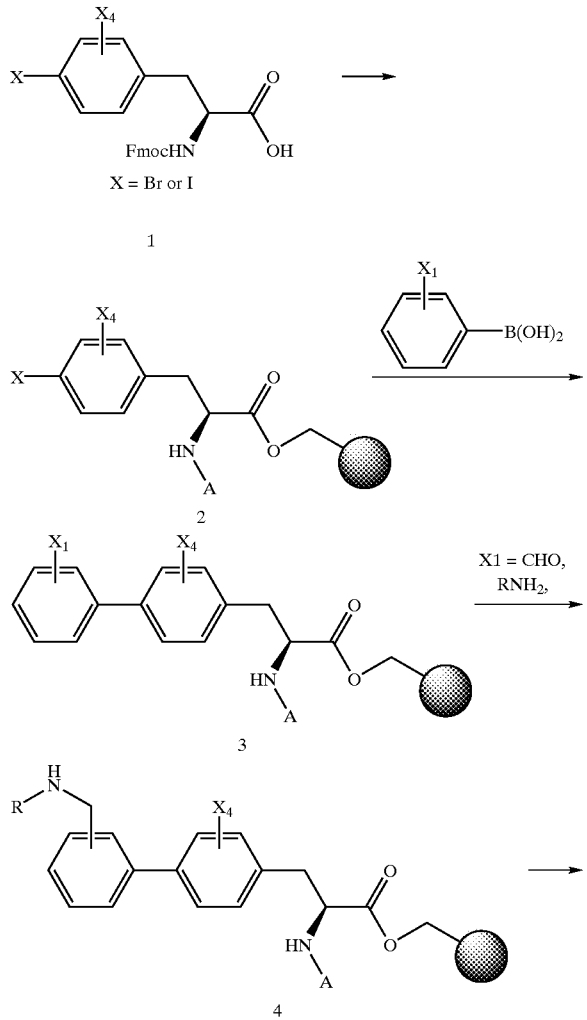

-continued

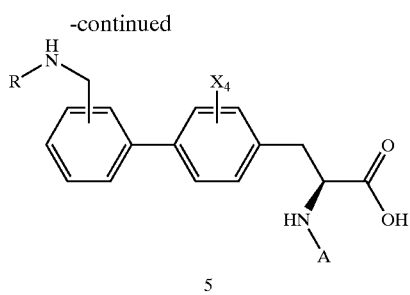

A representative synthetic procedure for preparing the compounds of the invention is set forth below and refers to the scheme shown above.

Halo-N-FMOC-Phe 1 (10 mmol) is suspended in 80 mL of DMC along with Wang resin (8 mmol) in a peptide synthesis flask with bubbling $N_2$ gas providing agitation. DIPC is added to a 0.25 M concentration followed by DMAP (1 mmol) and the reaction bubbled for 16 h. After washing the resin (3×80 mL with alternating DMF, methanol, and DCM) the resin is treated with 80 mL of 25% piperidine in NMP for 1 h followed by another wash cycle. A solution of 0.25M 2-Chlorobenzoic acid, HOBT, HBTU, and DIPEA in NMP is stirred for 0.5 h prior to addition to the resin 2. The reaction bubbled for 16 h and is washed as before. 100 mg portions of the resin can then be transferred to reaction vessels on the Argonaut Quest 210 parallel synthesis instrument and suspended with 0.25M boronic acid and DIPEA in 3 mL of degassed NMP that contained $Pd(PPH_3)_2Cl_2$ catalyst. The reactions were stirred magnetically and heated to 80 degrees C. for 16 h. The resin 3 was washed (3×5 mL with alternating DMF, methanol, and DCM). When in the previous step a formyl substituted boronic acid was used, the resin was swelled with 0.5M amine in 2 mL of 2% AcOH/NMP. After 1 h of stirring a 2 mL portion of 0.5M $Na(OAc)_3BH$ in NMP was added, followed by agitation for 16 h. After washing the resin 3 or 4 as before, 2 mL of TFA that contained 5% DCM and 2% triethylisilane was added followed by 1 h of agitation and filtration. The resin was washed with 1 mL of DCM and combined with the original filtrate. The reductive amination and TFA deblocking were also performed in polypropylene 48 well reaction blocks. The TFA was evaporated either by a vacuum centrifuge or via a stream of nitrogen gas to yield 20 mg of crude oil containing products 5 that were purified on HPLC and confirmed by Electrospray mass spectroscopy.

In cases where primary amines were used, compounds 4 can be further elaborated using standard methods to prepare sulfonamides 6, amides and carbamates 7, and disubstituted amines 8 as shown below.

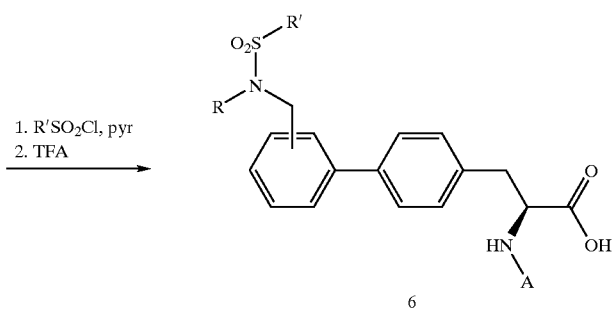

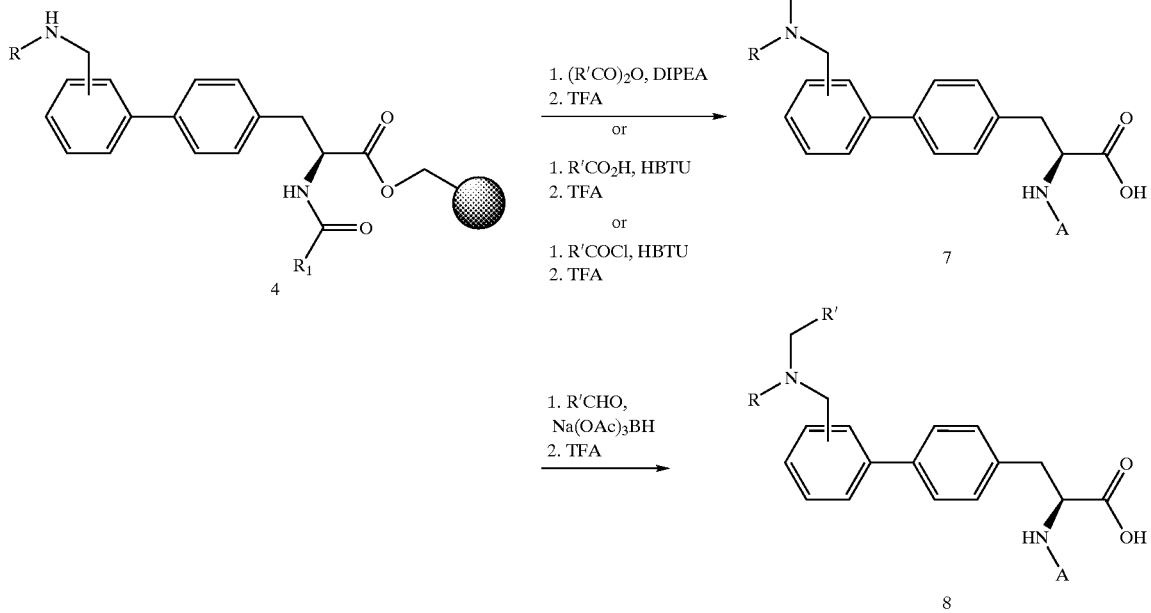

The free alpha carboxylic acid may be converted to an ester or to an amide using reactions well known in the art. For example, a free carboxyl group can be reacted with a suitable alcohol in the presence of an acid to esterify the carboxyl group using well known reactions and reagents. Similarly, amides are formed by reacting the carboxylic acid with an amine with removal of the water produced by the condensation using known methods. A example of a reaction for esterification is shown below.

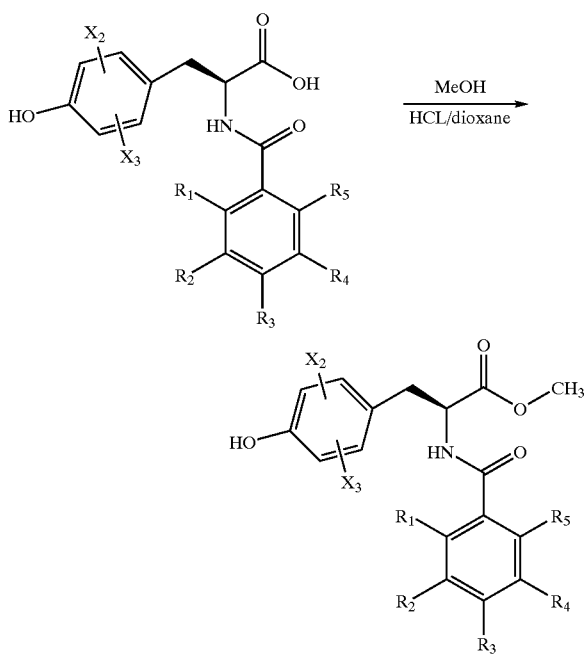

Also included in the scope of this invention are prodrugs of the compounds described above. Suitable prodrugs include known amino-protecting and carboxy-protecting groups which are released, for example hydrolyzed, to yield the parent compound under physiologic conditions. A preferred class of prodrugs are compounds in which a nitrogen atom in an amino, amidino, aminoalkyleneamino, iminoalkyleneamino or guanidino group is substituted with a hydroxy (OH) group, an alkylcarbonyl (—CO—W) group, an alkoxycarbonyl (—CO—OW), an acyloxyalkyl-alkoxycarbonyl (—CO—)—W—O—CO—W) group where W is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. Preferably the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and defluorophenoxy acyl. The reactions are generally exothermic and are carried out in inert solvents at reduced temperatures such as −78 to about 50C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 the contents of which are incorporated herein by reference in their entirety.

EXAMPLES

The invention will be more fully understood by reference to the following examples. They should not, however, be construed as limiting the scope of the invention. All patent and literature citations are herein incorporated by reference in their entirety.

Specific and representative compounds have been prepared and assayed for inhibitory binding activity using the methods described above and are shown in table 1 below. In the assay results, A represents an $IC_{50}$ value greater than 1.0 micromolar and B represents an $IC_{50}$ value less than 1.0 micromolar.

TABLE 1

| Structure | Compound number | Assay Result |
|---|---|---|
| 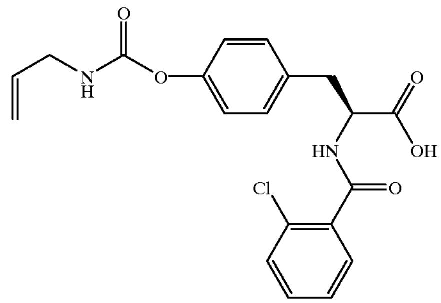 | 001 | B |
| 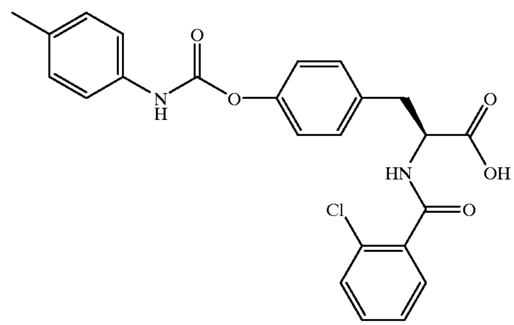 | 002 | B |
| 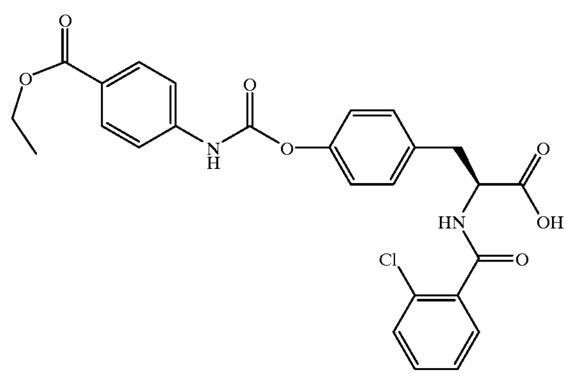 | 003 | B |
| 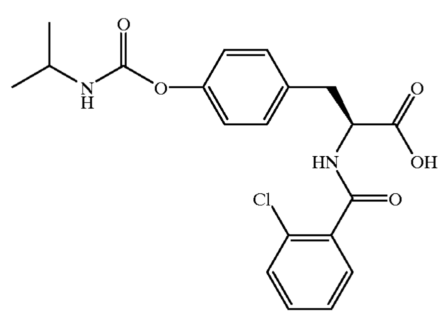 | 004 | B |

TABLE 1-continued

| Structure | Compound number | Assay Result |
|---|---|---|
| 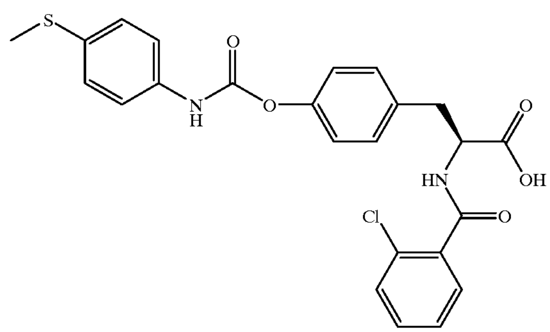 | 005 | B |
| 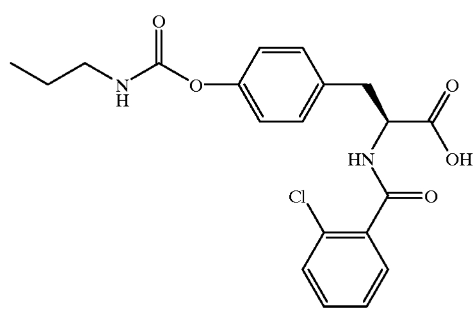 | 006 | B |
| 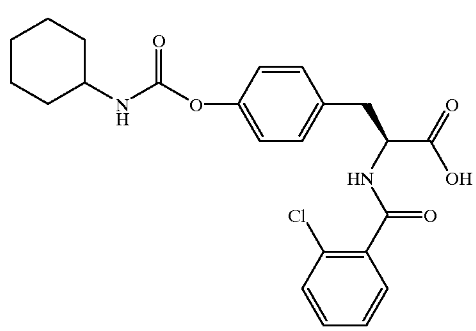 | 007 | B |
| 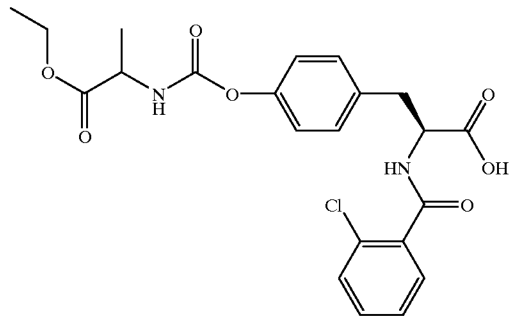 | 008 | B |

TABLE 1-continued
| Structure | Compound number | Assay Result |
|---|---|---|
| 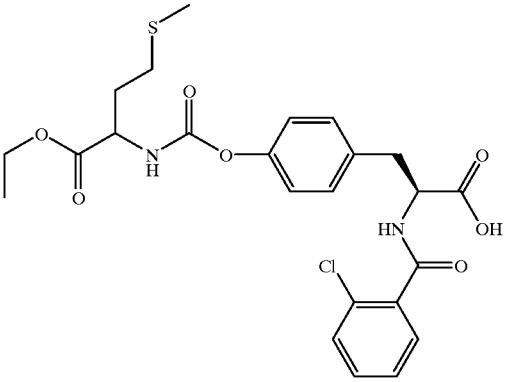 | 009 | B |
| 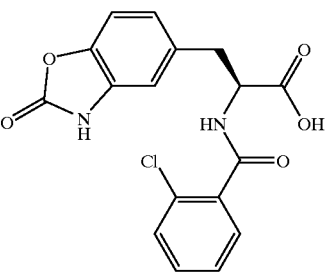 | 010 | B |
| 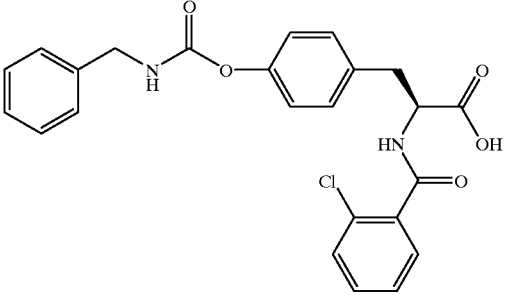 | 011 | B |
| 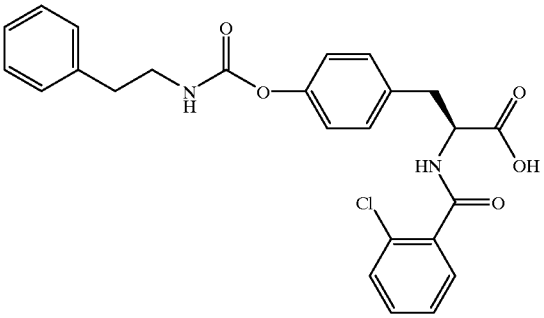 | 012 | B |

TABLE 1-continued

| Structure | Compound number | Assay Result |
|---|---|---|
| 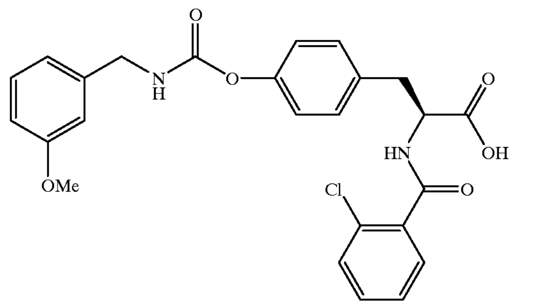 | 013 | B |
| 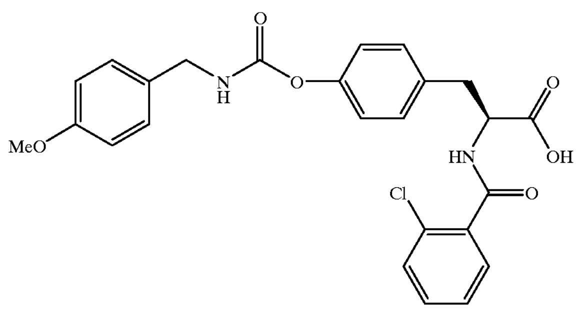 | 014 | B |
| 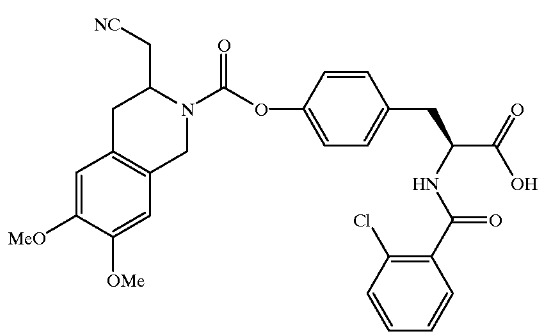 | 015 | B |
| 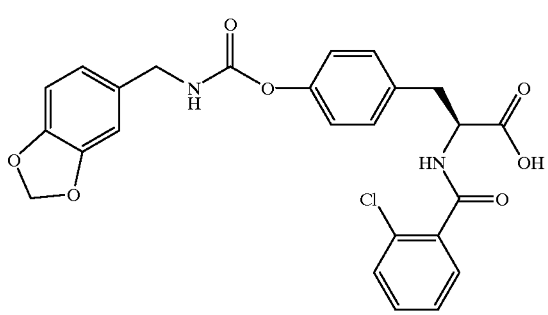 | 016 | B |

TABLE 1-continued

| Structure | Compound number | Assay Result |
|---|---|---|
| 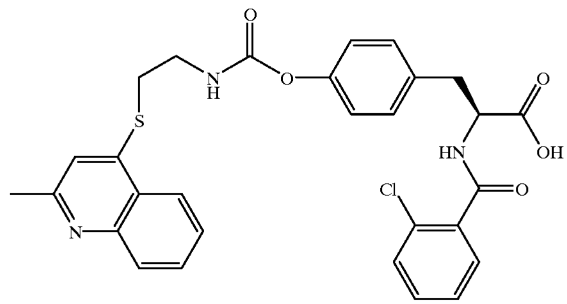 | 017 | B |
| 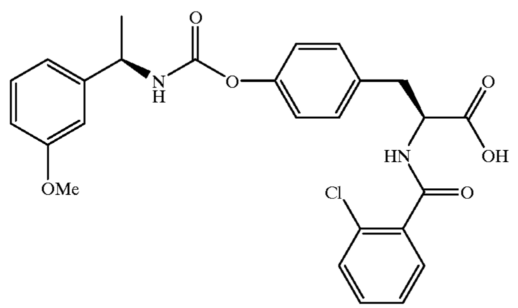 | 018 | B |
| 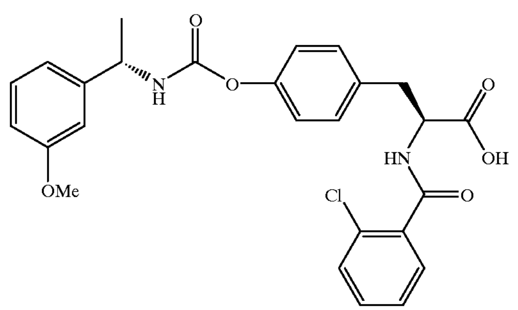 | 019 | B |
| 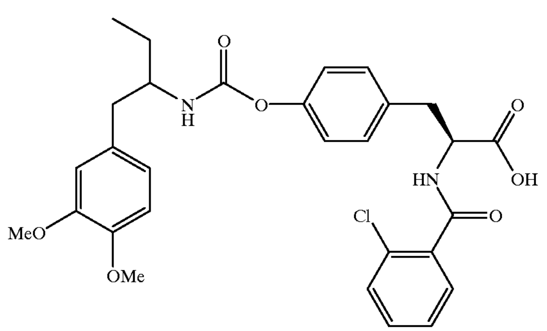 | 020 | B |

TABLE 1-continued

| Structure | Compound number | Assay Result |
|---|---|---|
| 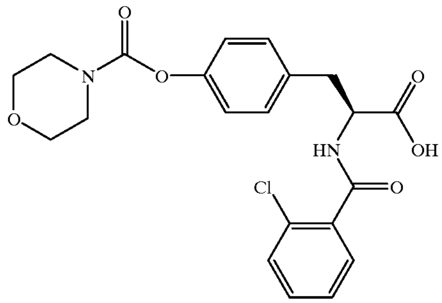 | 021 | B |
| 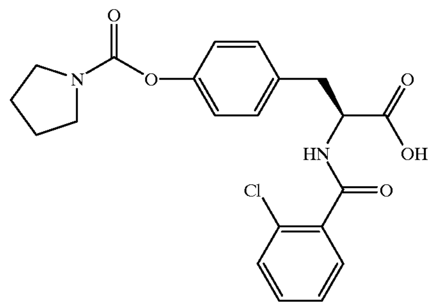 | 022 | B |
| 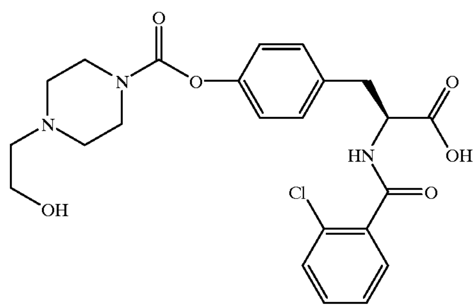 | 023 | B |
| 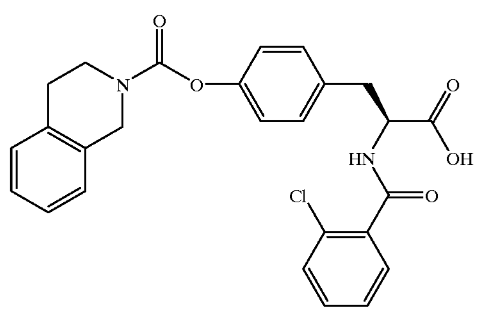 | 024 | B |
| 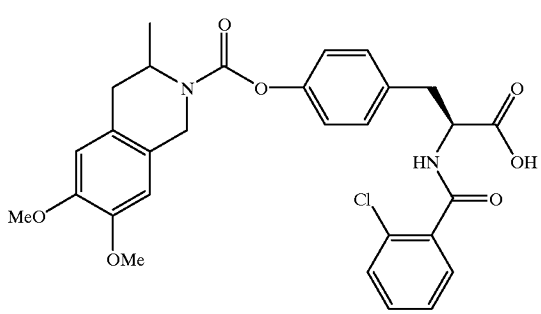 | 025 | B |

TABLE 1-continued

| Structure | Compound number | Assay Result |
|---|---|---|
| 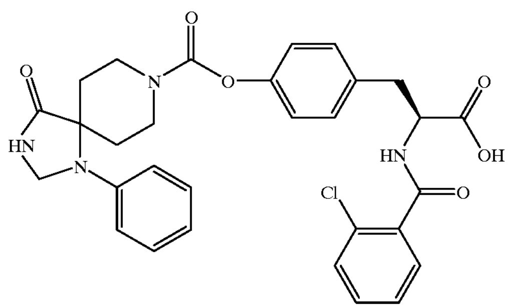 | 026 | B |
| 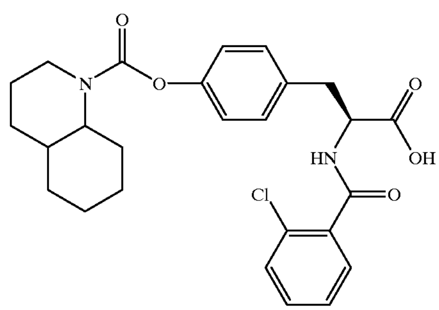 | 027 | B |
| 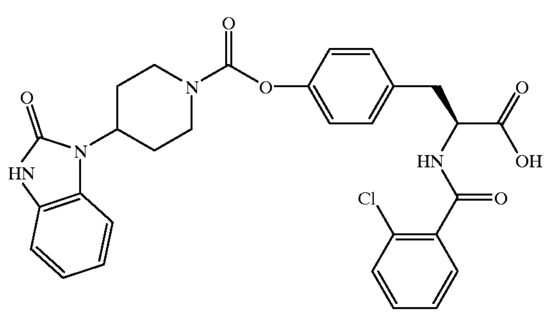 | 028 | B |
| 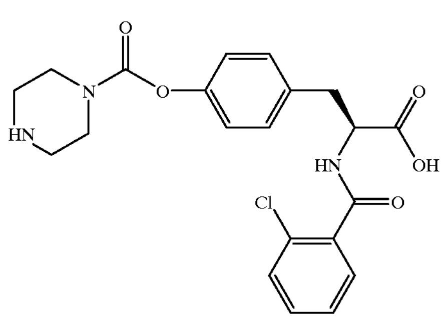 | 029 | B |

TABLE 1-continued

| Structure | Compound number | Assay Result |
|---|---|---|
| 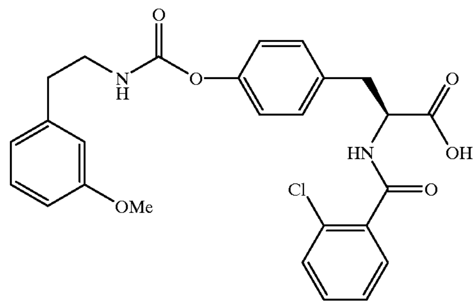 | 030 | B |
| 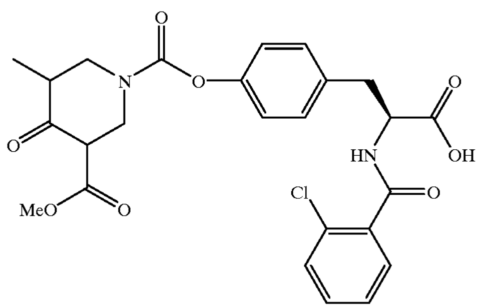 | 031 | B |
| 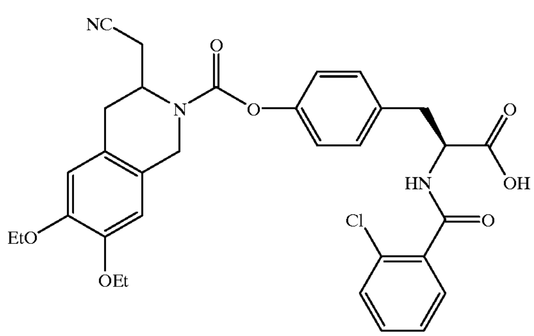 | 032 | B |
| 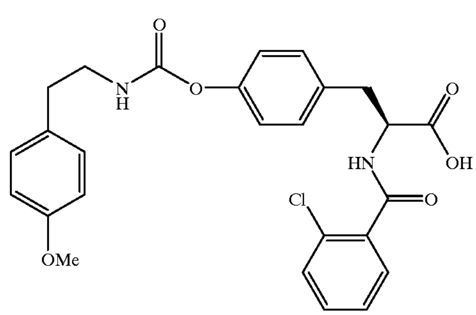 | 033 | B |

TABLE 1-continued

| Structure | Compound number | Assay Result |
|---|---|---|
| 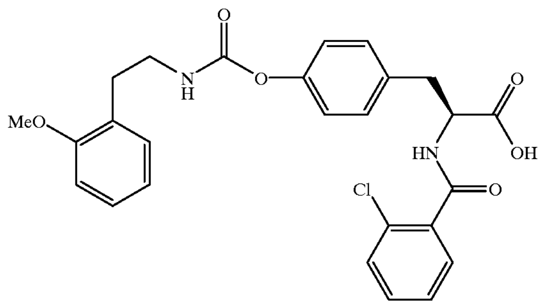 | 034 | B |
| 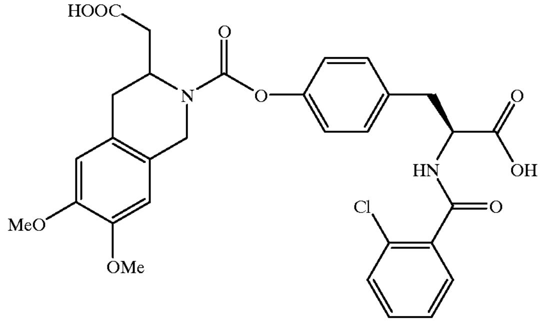 | 035 | B |
| 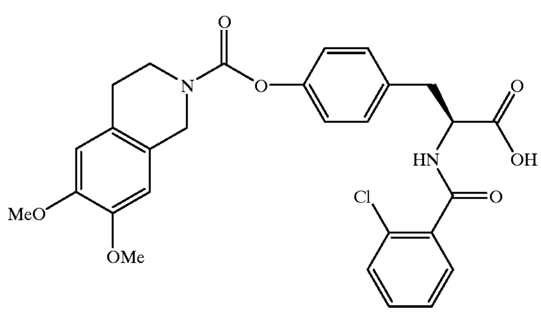 | 036 | B |
| 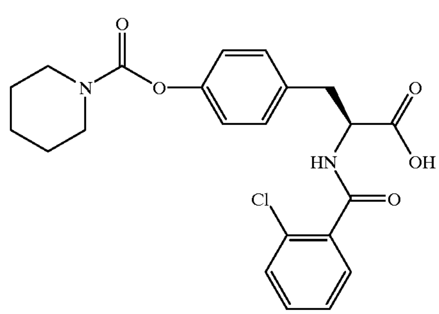 | 037 | B |

TABLE 1-continued
| Structure | Compound number | Assay Result |
|---|---|---|
| 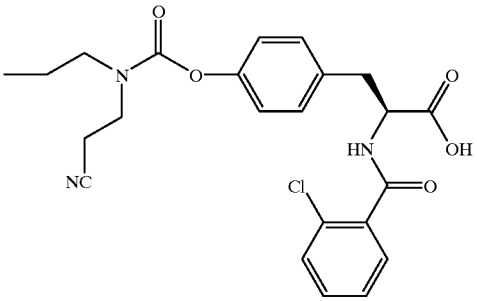 | 038 | B |
| 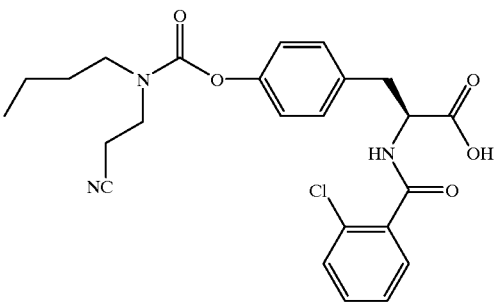 | 039 | B |
| 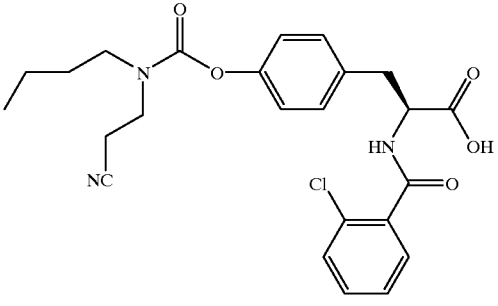 | 040 | B |
| 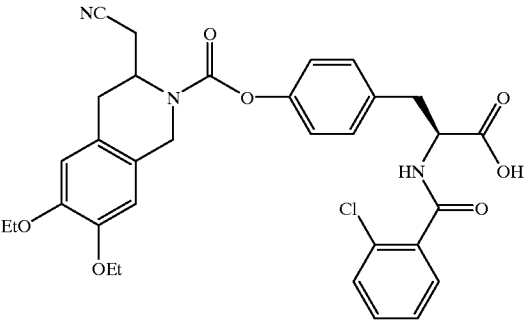 | 041 | B |

TABLE 1-continued

| Structure | Compound number | Assay Result |
|---|---|---|
| 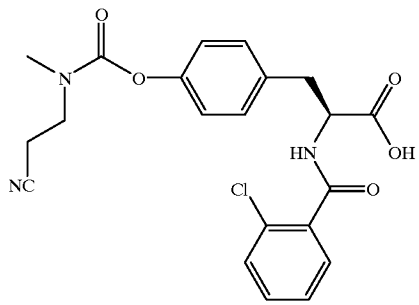 | 042 | B |
| 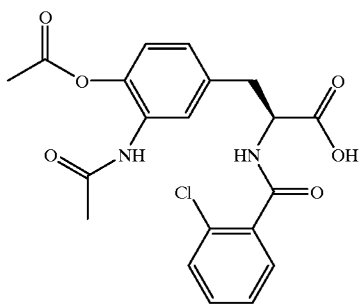 | 043 | A |
| 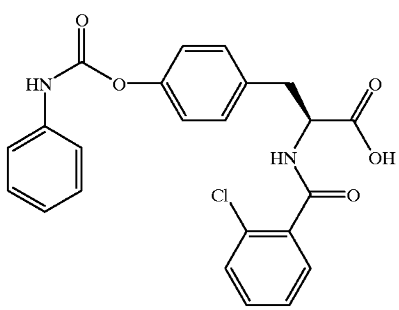 | 044 | A |
| 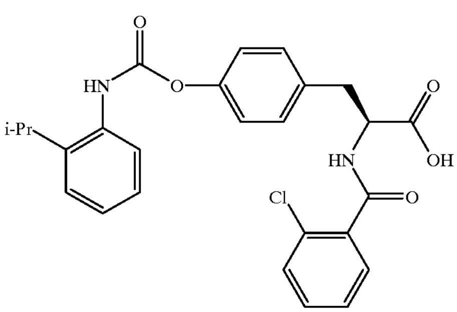 | 045 | A |

TABLE 1-continued

| Structure | Compound number | Assay Result |
|---|---|---|
| 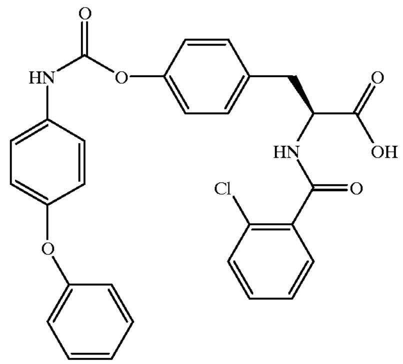 | 046 | A |
| 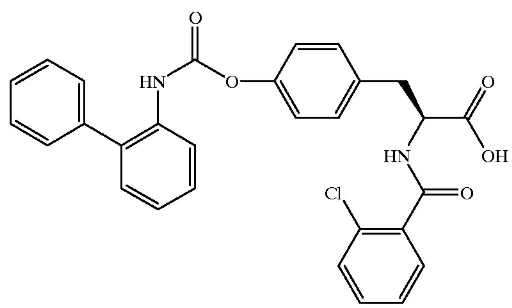 | 047 | A |
| 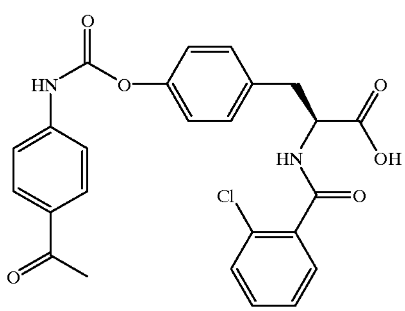 | 048 | A |
| 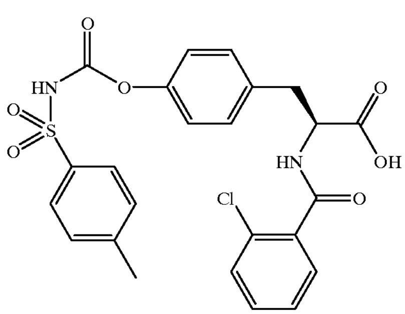 | 049 | A |

TABLE 1-continued

| Structure | Compound number | Assay Result |
|---|---|---|
| 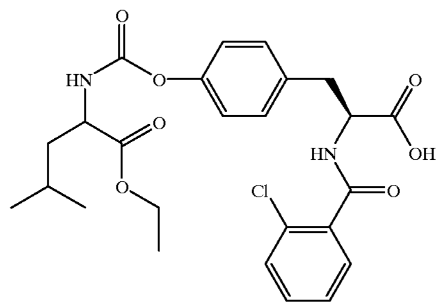 | 050 | A |
| 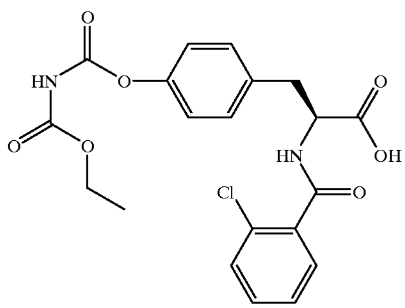 | 051 | A |
| 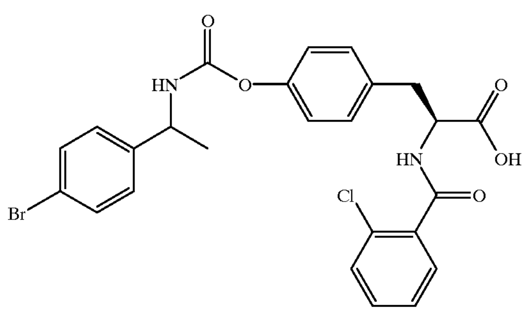 | 052 | A |
| 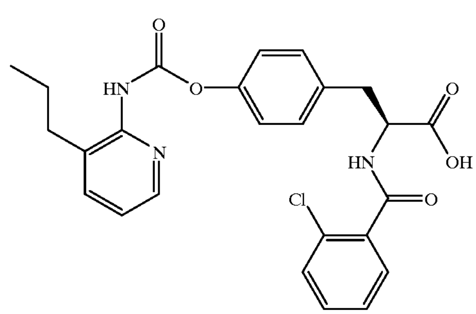 | 053 | A |
| 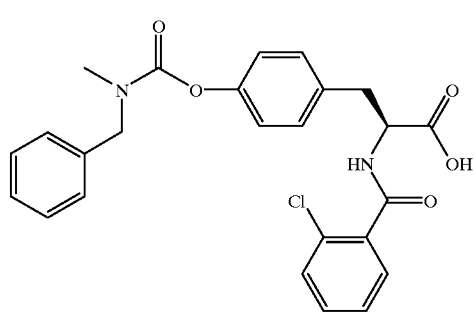 | 054 | A |

TABLE 1-continued

| Structure | Compound number | Assay Result |
| --- | --- | --- |
| 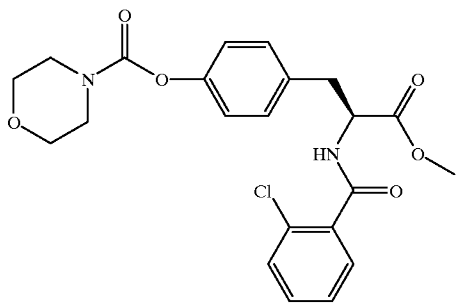 | 055 | A |
| 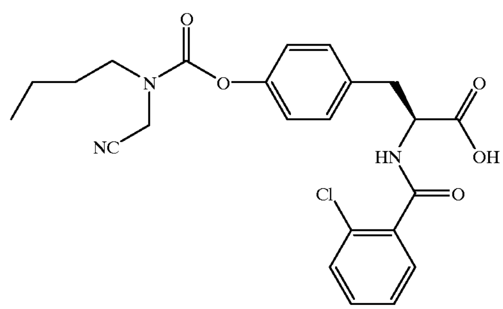 | 056 | A |
| 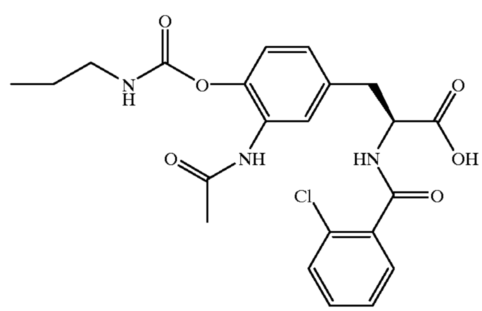 | 057 | A |
| 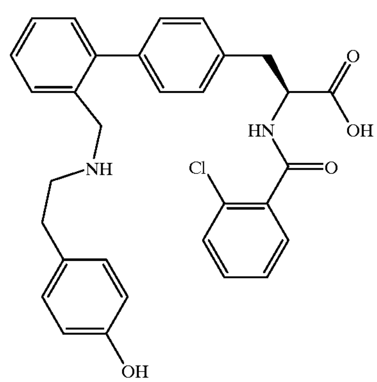 | 058 | B |

TABLE 1-continued

| Structure | Compound number | Assay Result |
|---|---|---|
| 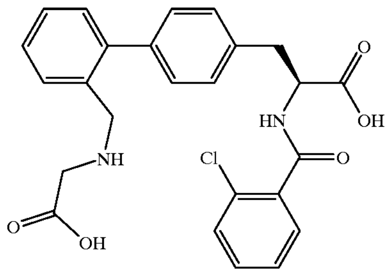 | 059 | B |
| 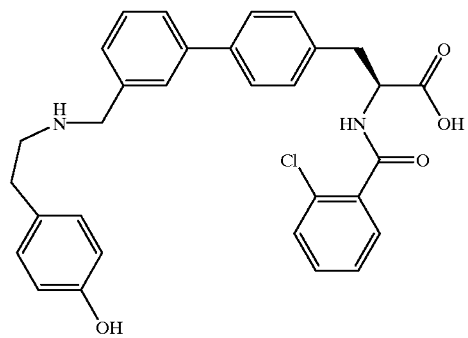 | 060 | B |
| 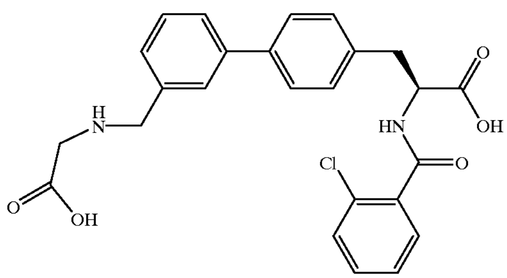 | 061 | B |
| 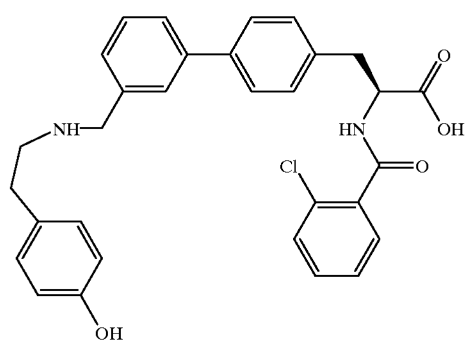 | 062 | B |
| 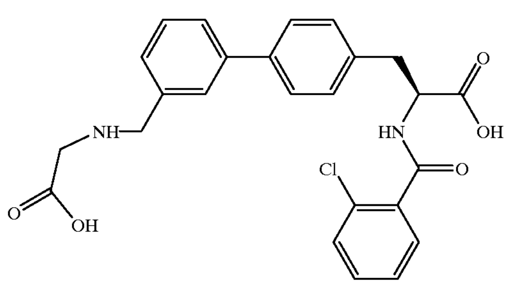 | 063 | B |

TABLE 1-continued
| Structure | Compound number | Assay Result |
|---|---|---|
| 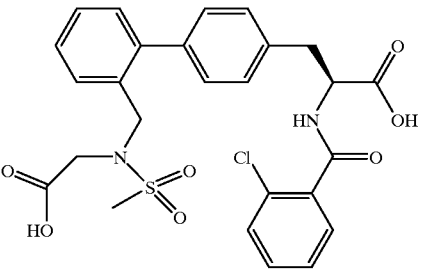 | 064 | B |
| 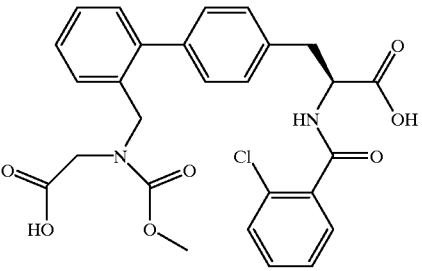 | 065 | B |
| 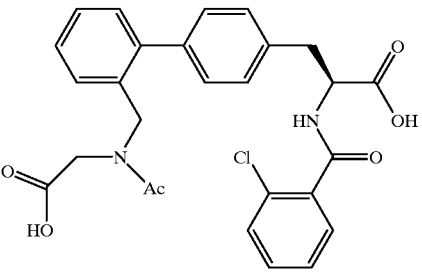 | 066 | B |
| 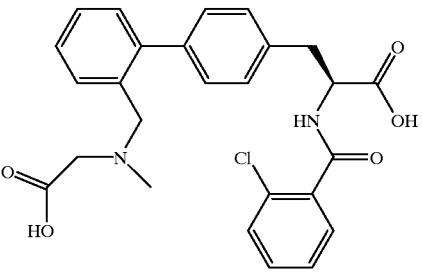 | 067 | B |
| 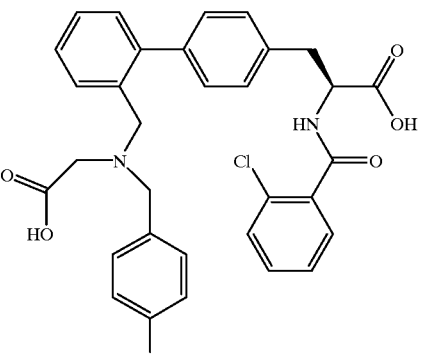 | 068 | B |

TABLE 1-continued

| Structure | Compound number | Assay Result |
|---|---|---|
| 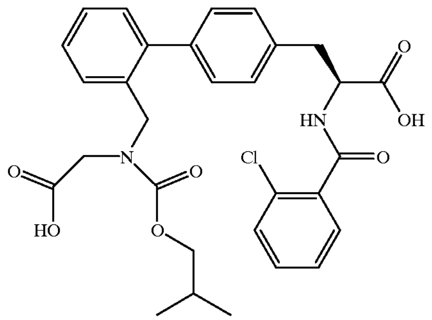 | 069 | B |
| 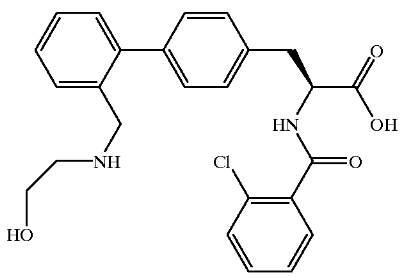 | 070 | B |
| 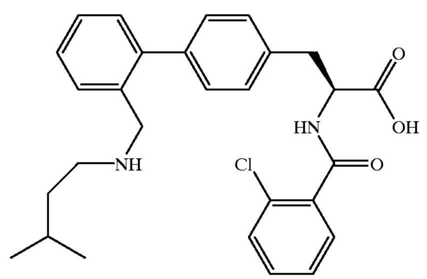 | 071 | B |
| 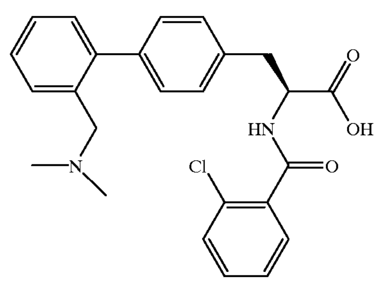 | 072 | B |
| 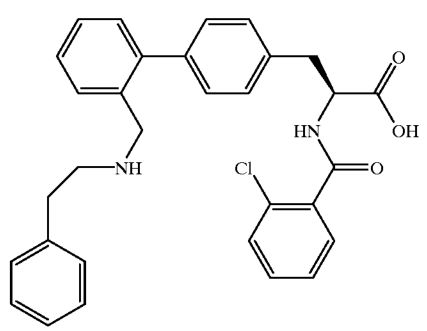 | 073 | B |

TABLE 1-continued

| Structure | Compound number | Assay Result |
|---|---|---|
| 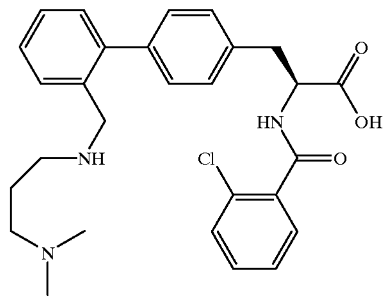 | 074 | B |
| 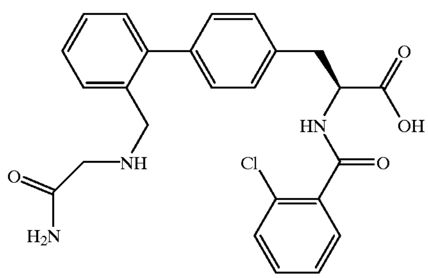 | 075 | B |
| 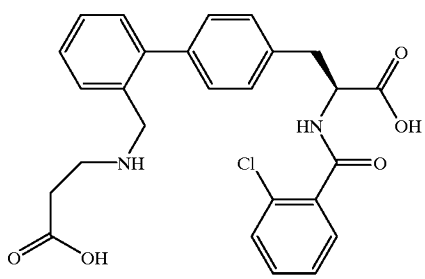 | 076 | B |
| 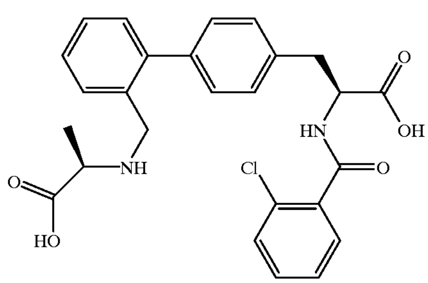 | 077 | B |
| 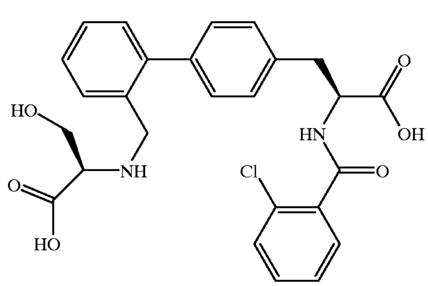 | 078 | B |

TABLE 1-continued
| Structure | Compound number | Assay Result |
|---|---|---|
| 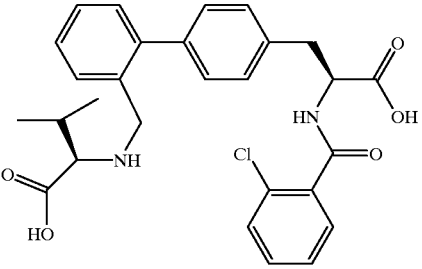 | 079 | B |
| 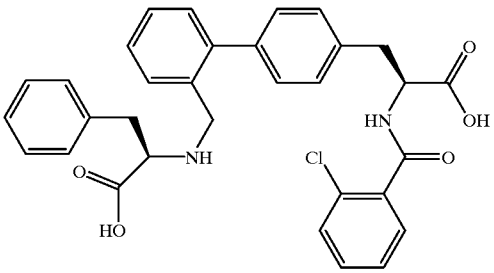 | 080 | B |
| 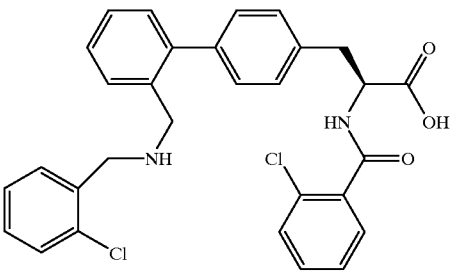 | 081 | B |
| 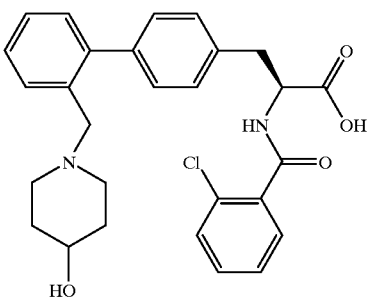 | 082 | B |
| 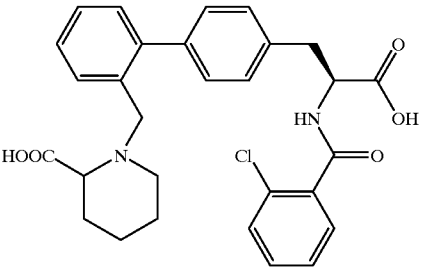 | 083 | B |

TABLE 1-continued

| Structure | Compound number | Assay Result |
|---|---|---|
| 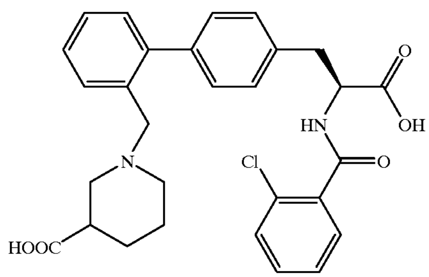 | 084 | B |
| 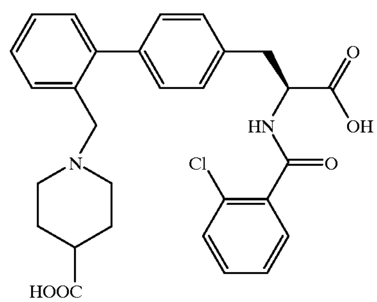 | 085 | B |
| 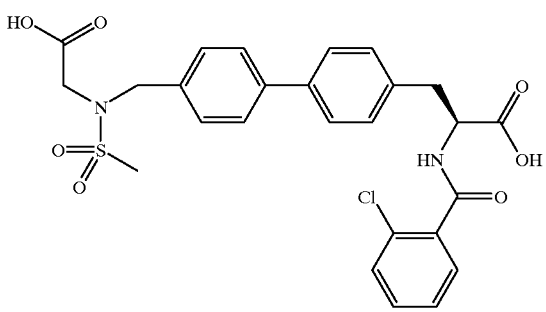 | 086 | B |
| 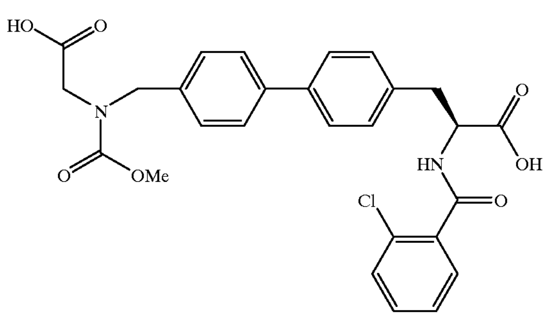 | 087 | B |
| 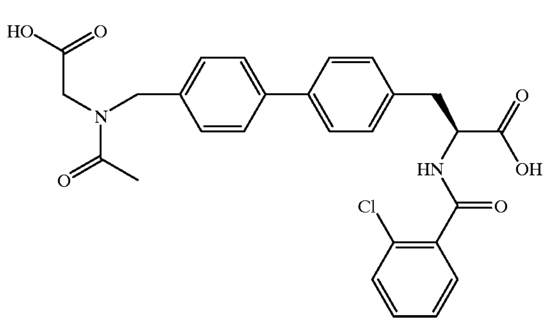 | 088 | B |

TABLE 1-continued

| Structure | Compound number | Assay Result |
|---|---|---|
| 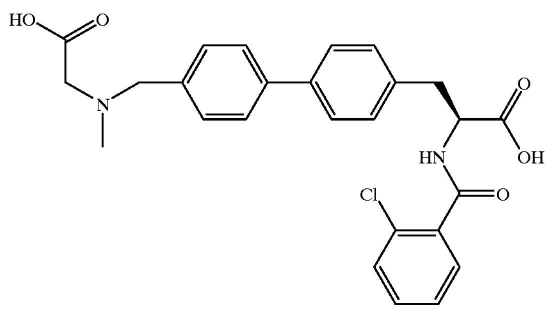 | 089 | B |
| 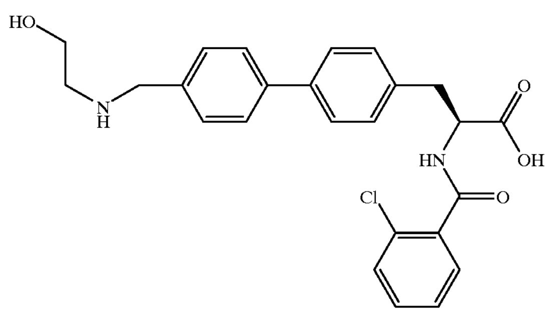 | 090 | B |
| 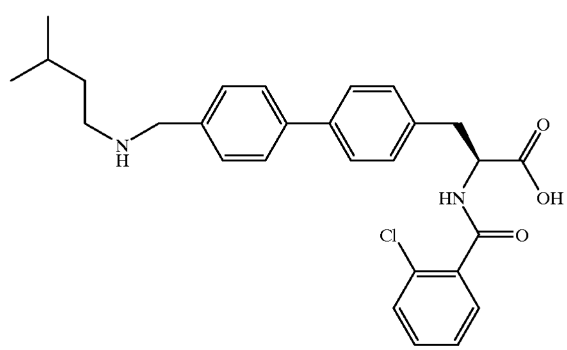 | 091 | B |
| 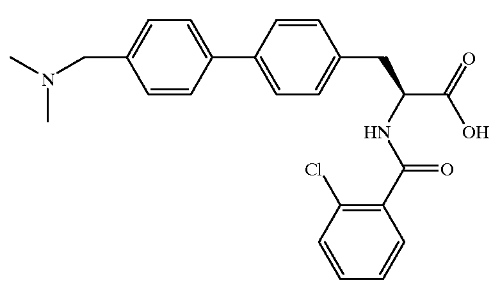 | 092 | B |

TABLE 1-continued
| Structure | Compound number | Assay Result |
|---|---|---|
| 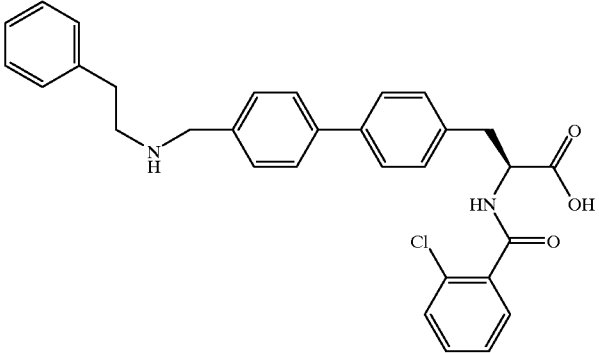 | 093 | B |
| 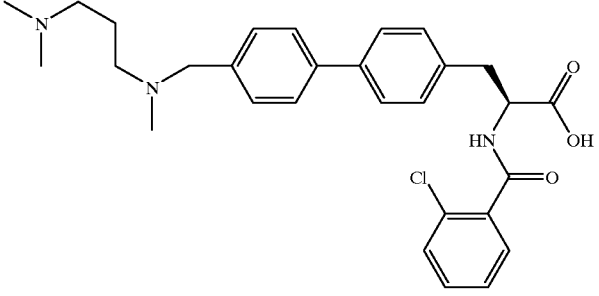 | 094 | B |
| 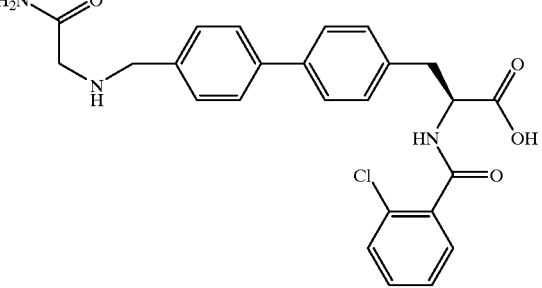 | 095 | B |
| 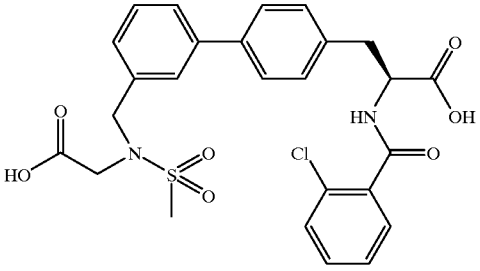 | 096 | B |
| 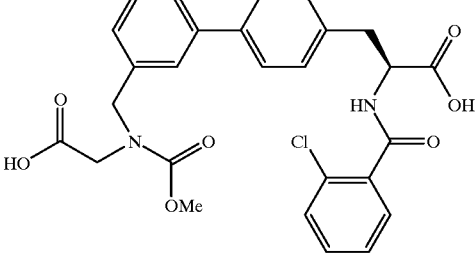 | 097 | B |

TABLE 1-continued

| Structure | Compound number | Assay Result |
|---|---|---|
| 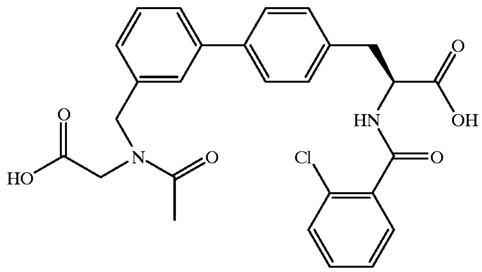 | 098 | B |
| 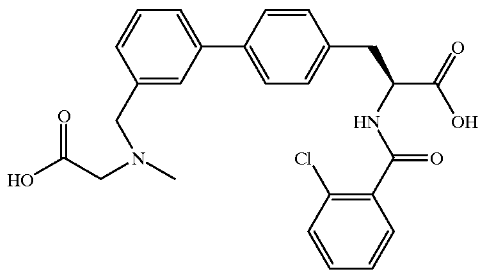 | 099 | B |
| 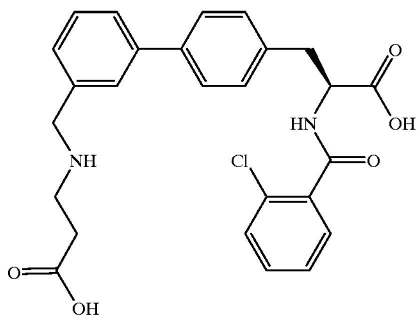 | 100 | B |
| 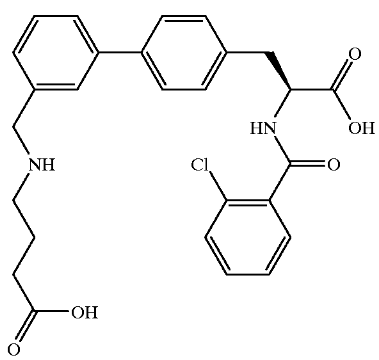 | 101 | B |
| 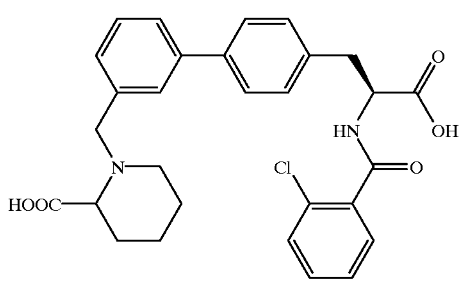 | 102 | B |

TABLE 1-continued

| Structure | Compound number | Assay Result |
|---|---|---|
| 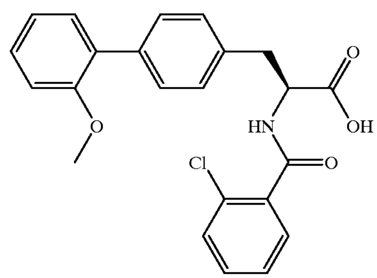 | 103 | B |
| 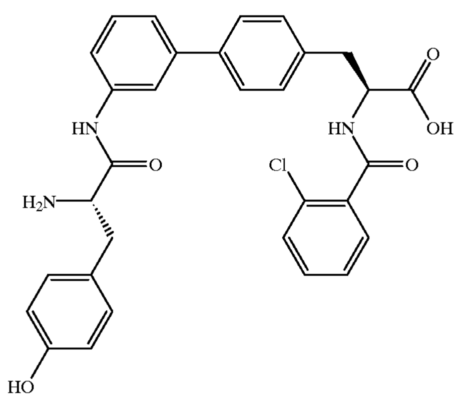 | 104 | A |
| 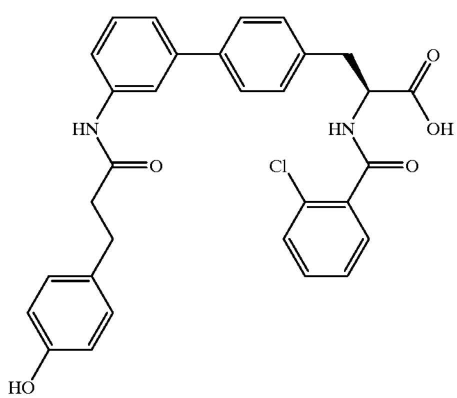 | 105 | A |
| 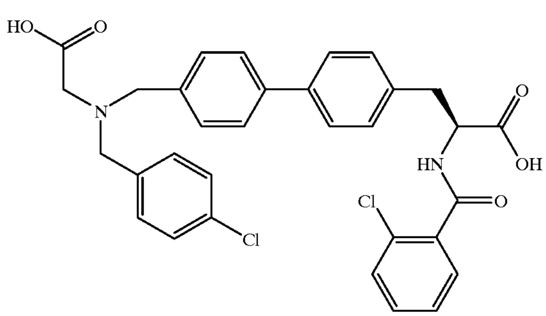 | 106 | A |

TABLE 1-continued

| Structure | Compound number | Assay Result |
|---|---|---|
| 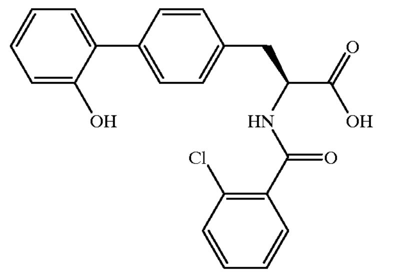 | 107 | A |
| 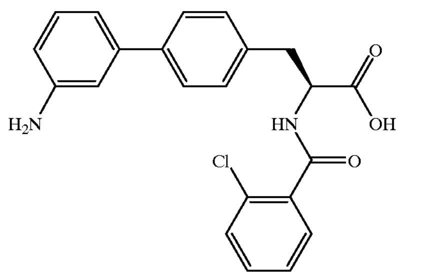 | 108 | A |
| 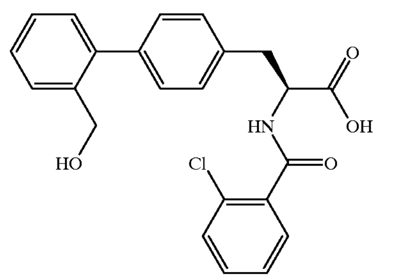 | 109 | A |
| 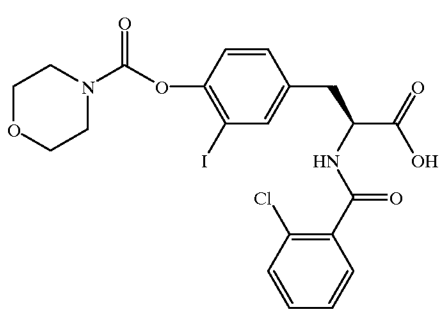 | 111 | B |
| 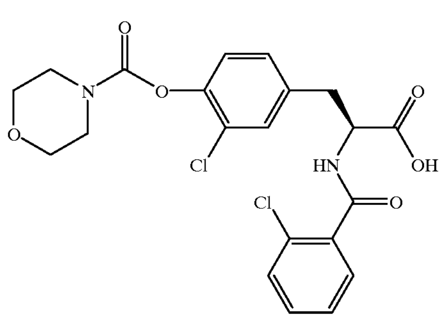 | 112 | B |

TABLE 1-continued

| Structure | Compound number | Assay Result |
|---|---|---|
| 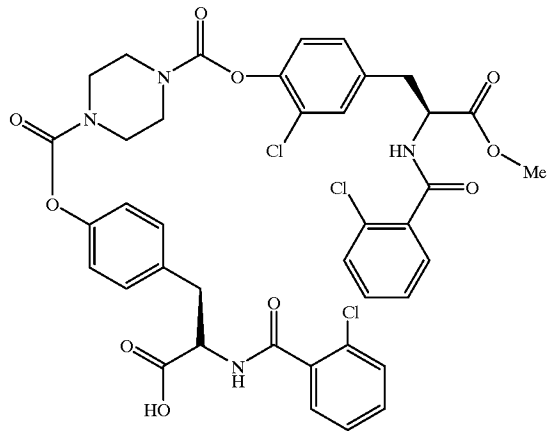 | 113 | B |
| 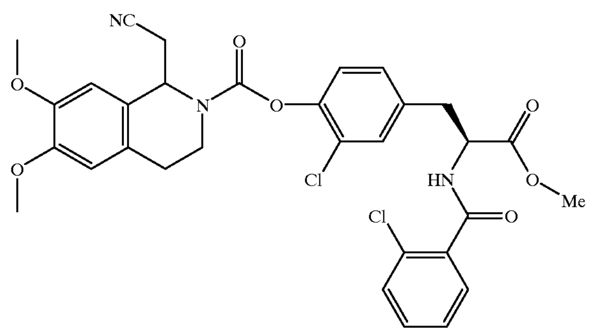 | 114 | B |
| 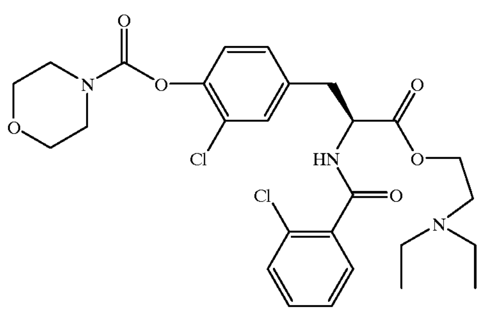 | 115 | B |
| 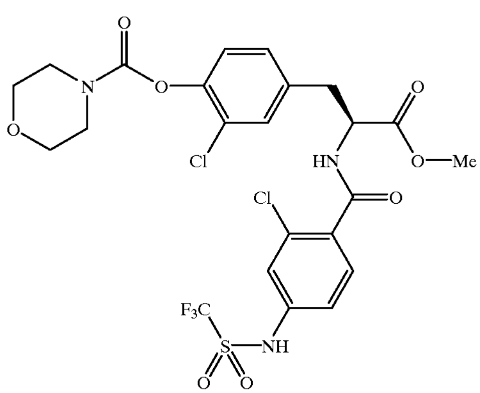 | 116 | A |

TABLE 1-continued

| Structure | Compound number | Assay Result |
|---|---|---|
| 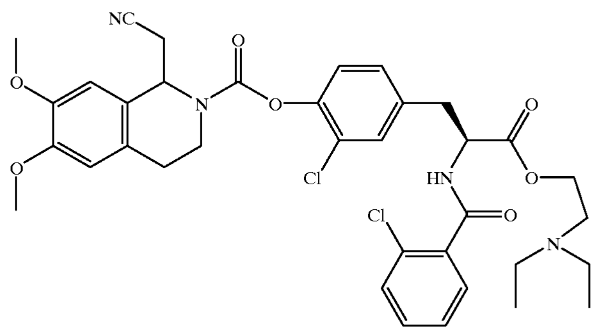 | 117 | B |
| 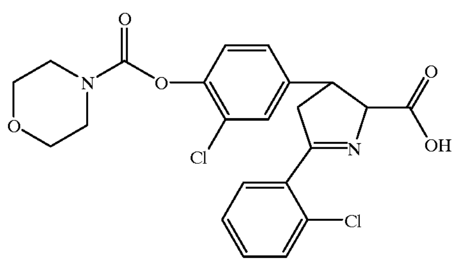 | 118 | B |
| 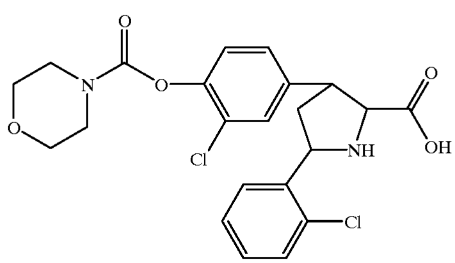 | 119 | B |
| 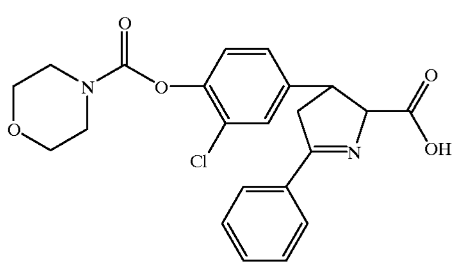 | 120 | B |
| 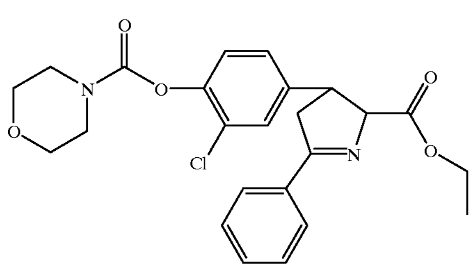 | 121 | B |

TABLE 1-continued

| Structure | Compound number | Assay Result |
|---|---|---|
| 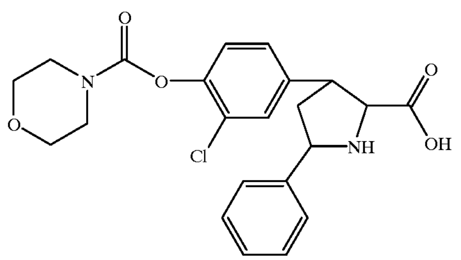 | 122 | B |
| 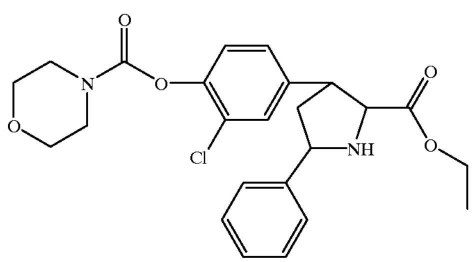 | 123 | B |
| 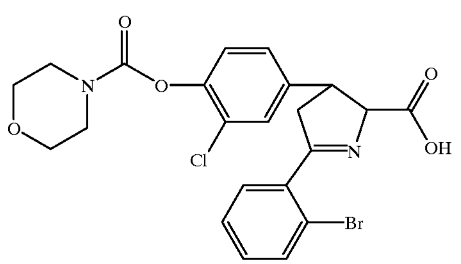 | 124 | B |
| 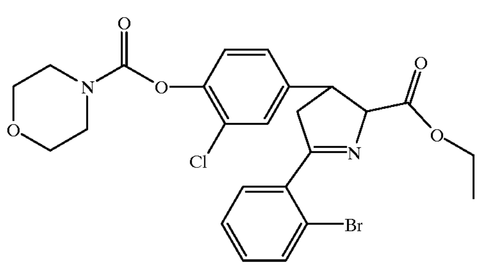 | 125 | B |
| 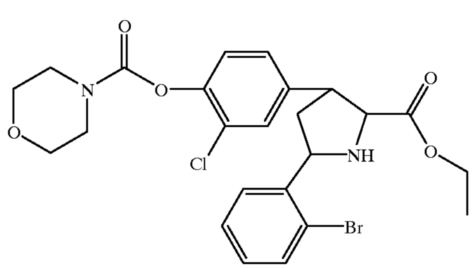 | 126 | B |

TABLE 1-continued

| Structure | Compound number | Assay Result |
|---|---|---|
| 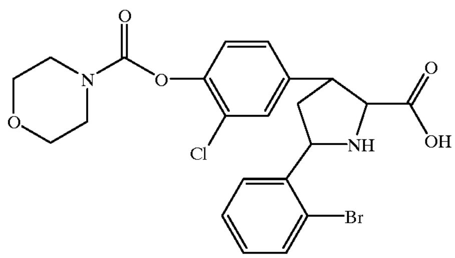 | 127 | B |
| 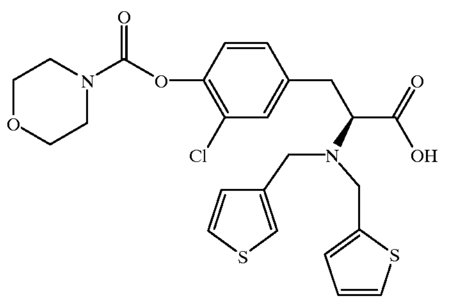 | 128 | B |

The following table 2 illustrates further compounds prepared and assayed, each of which was found to inhibit binding activity exhibiting an $IC_{50}$ value less than 1.0 micromolar using the methods described above.

TABLE 2

| R | R'-compd no. | R | R'-compd no. |
|---|---|---|---|
| 1-naphthyl-NH- | 129, 2-Cl-benzoyl | 2-(OCF₃)-phenyl-NH- | 130, 2-Cl-benzoyl |
| 2-Br-phenyl-NH- | 131, 2-Cl-benzoyl | 3-CN-phenyl-NH- | 132, 2-Cl-benzoyl |
| MeO-NH- | 133, 2-Cl-benzoyl | morpholin-4-yl | 134, 2-Cl-4-NO₂-benzoyl |
| 2-OCH₃-phenyl-NH- | 135, 2-Cl-benzoyl | morpholin-4-yl | 136, 2-Cl-5-NO₂-benzoyl |

TABLE 2-continued
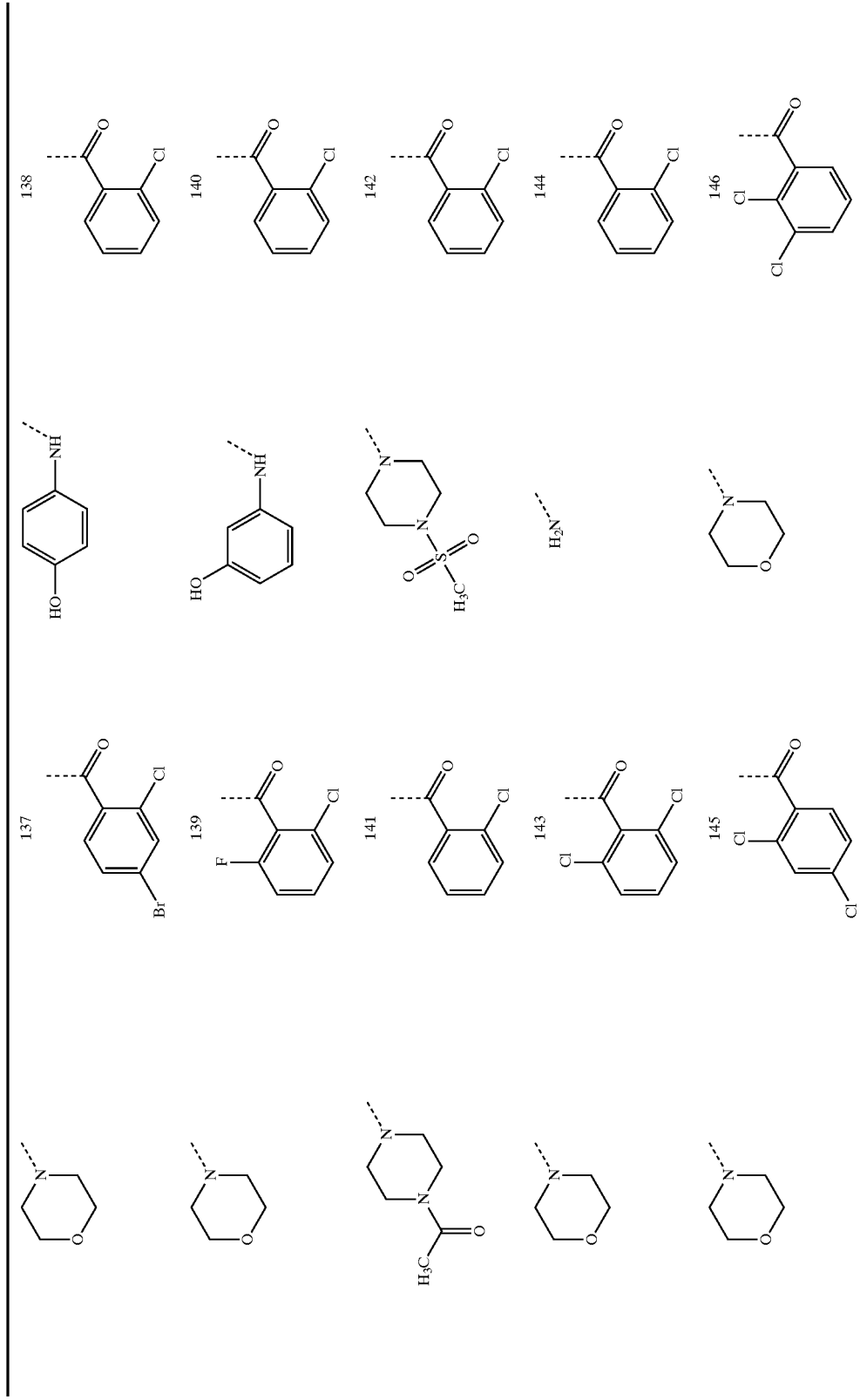

TABLE 2-continued
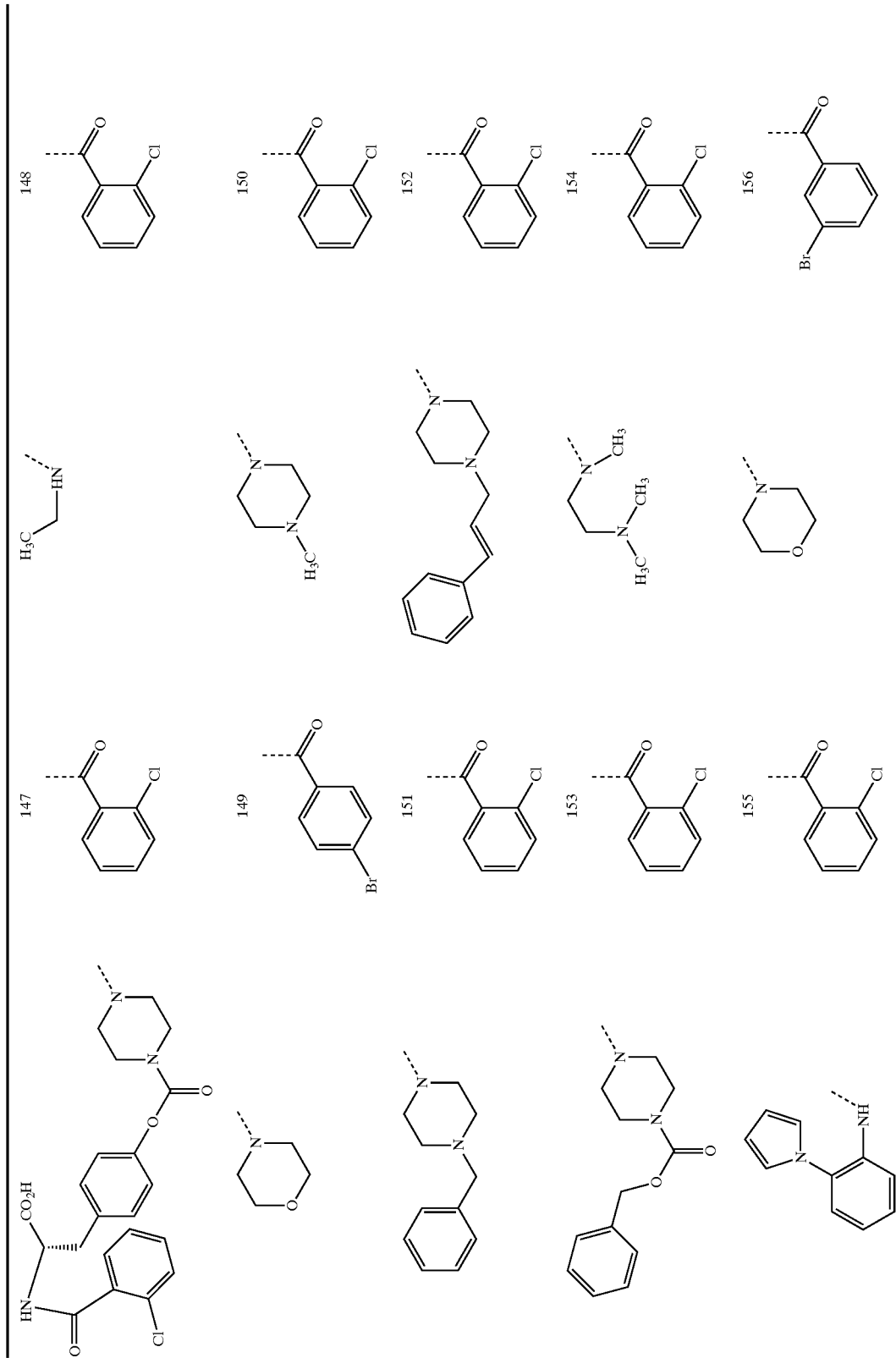

TABLE 2-continued

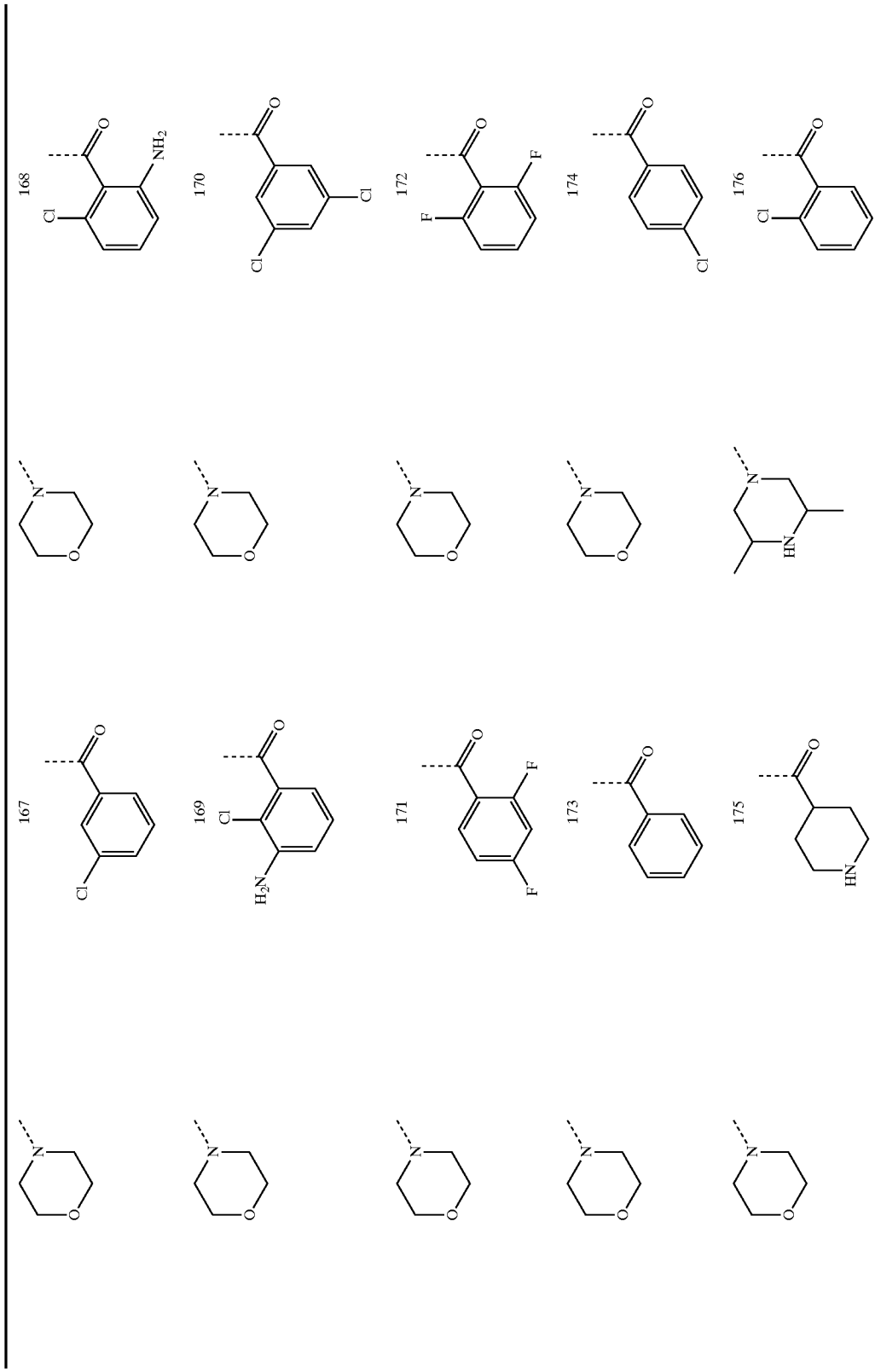

TABLE 2-continued

TABLE 2-continued

TABLE 2-continued
| | | | | |
|---|---|---|---|---|
| 195 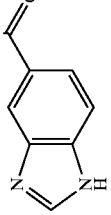 | 196 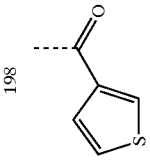 | 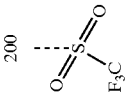 | 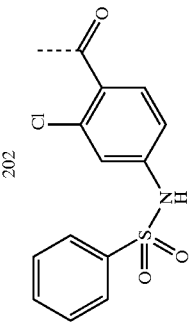 | 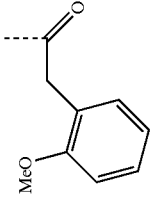 |
| 197 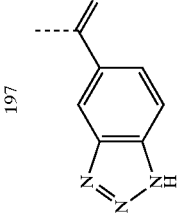 | 198 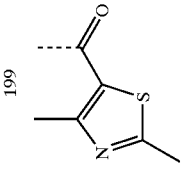 | 199 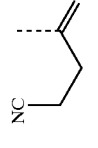 | 200 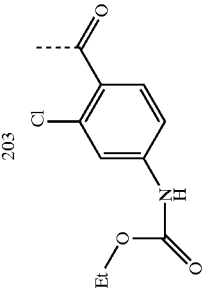 | 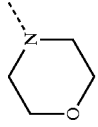 |
| 201 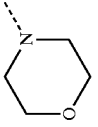 | 202 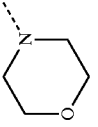 | 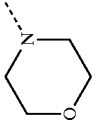 | 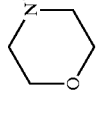 | 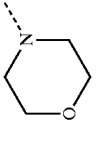 |
| 203 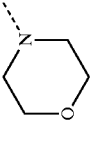 | 204 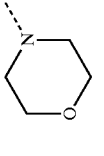 | | | |

TABLE 2-continued

TABLE 2-continued

TABLE 2-continued
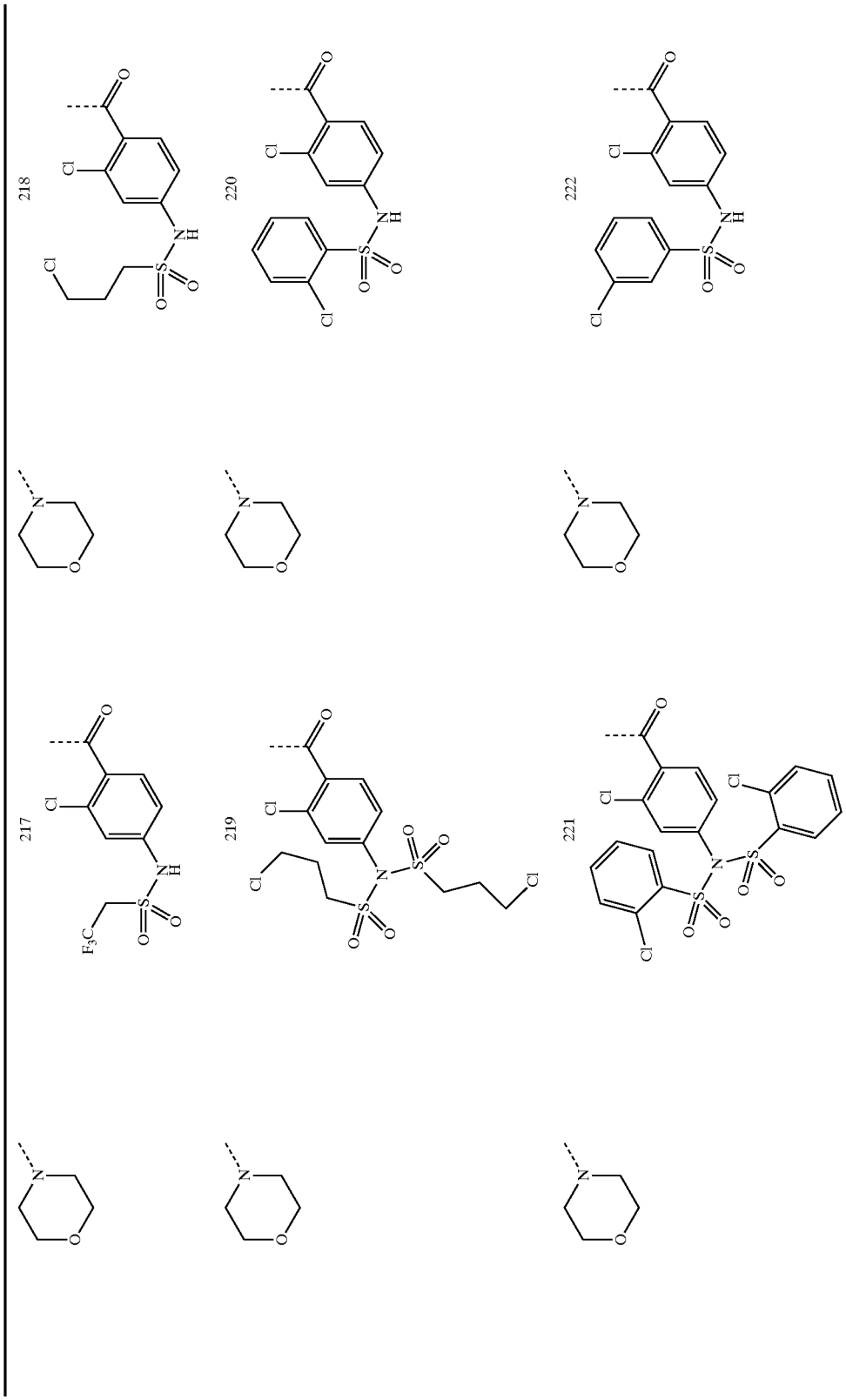

TABLE 2-continued
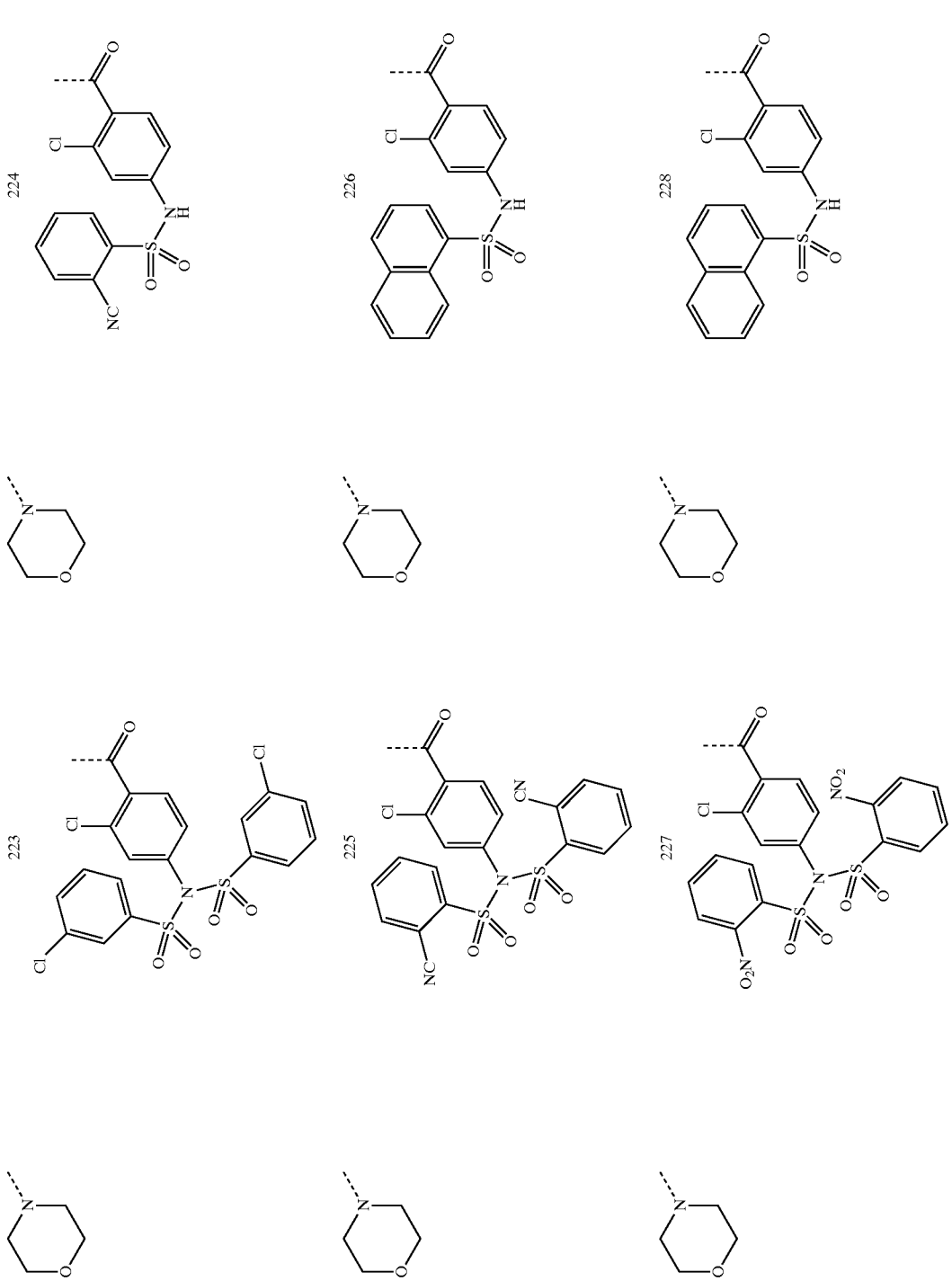

TABLE 2-continued

TABLE 2-continued

TABLE 2-continued
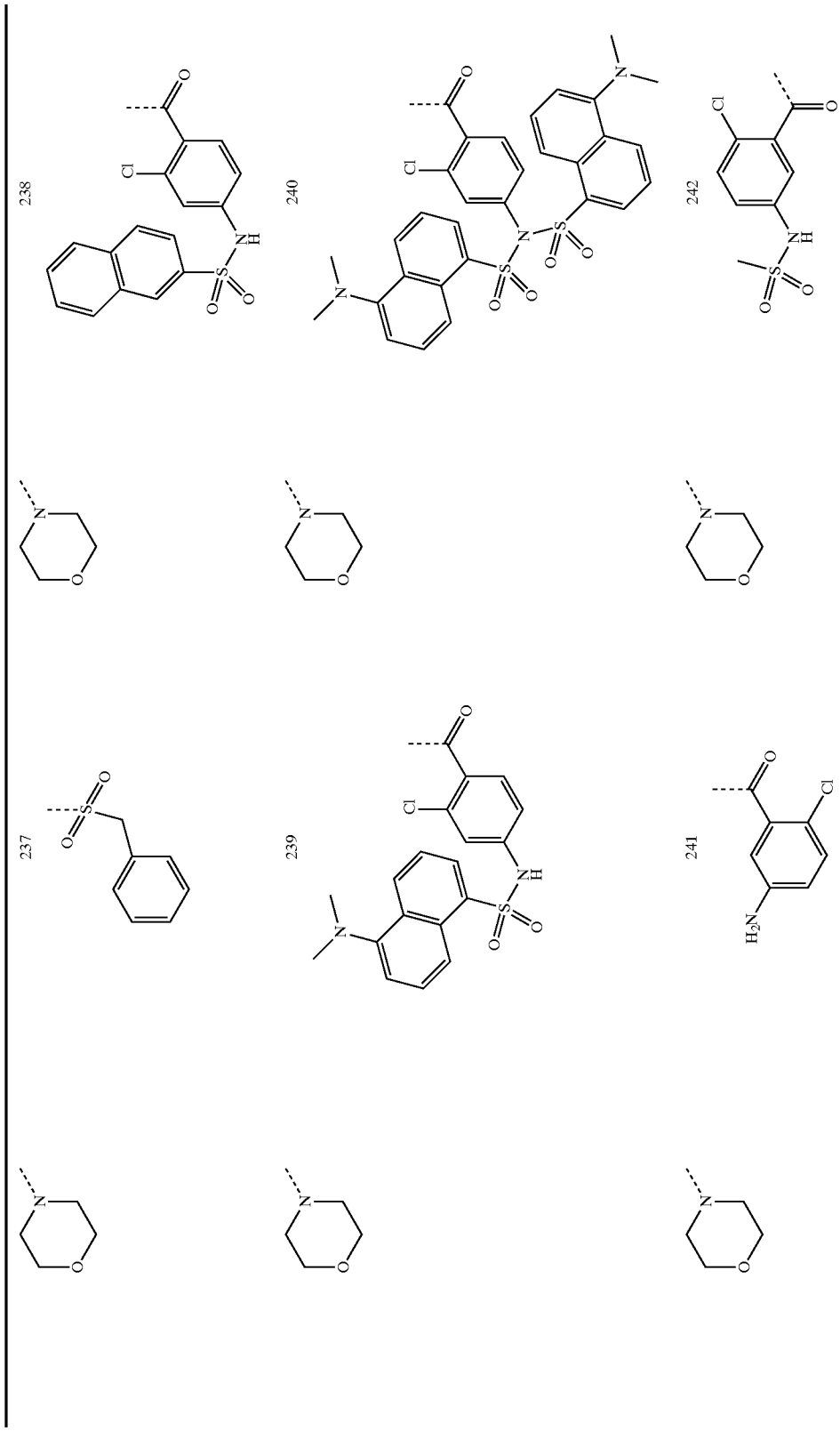

TABLE 2-continued

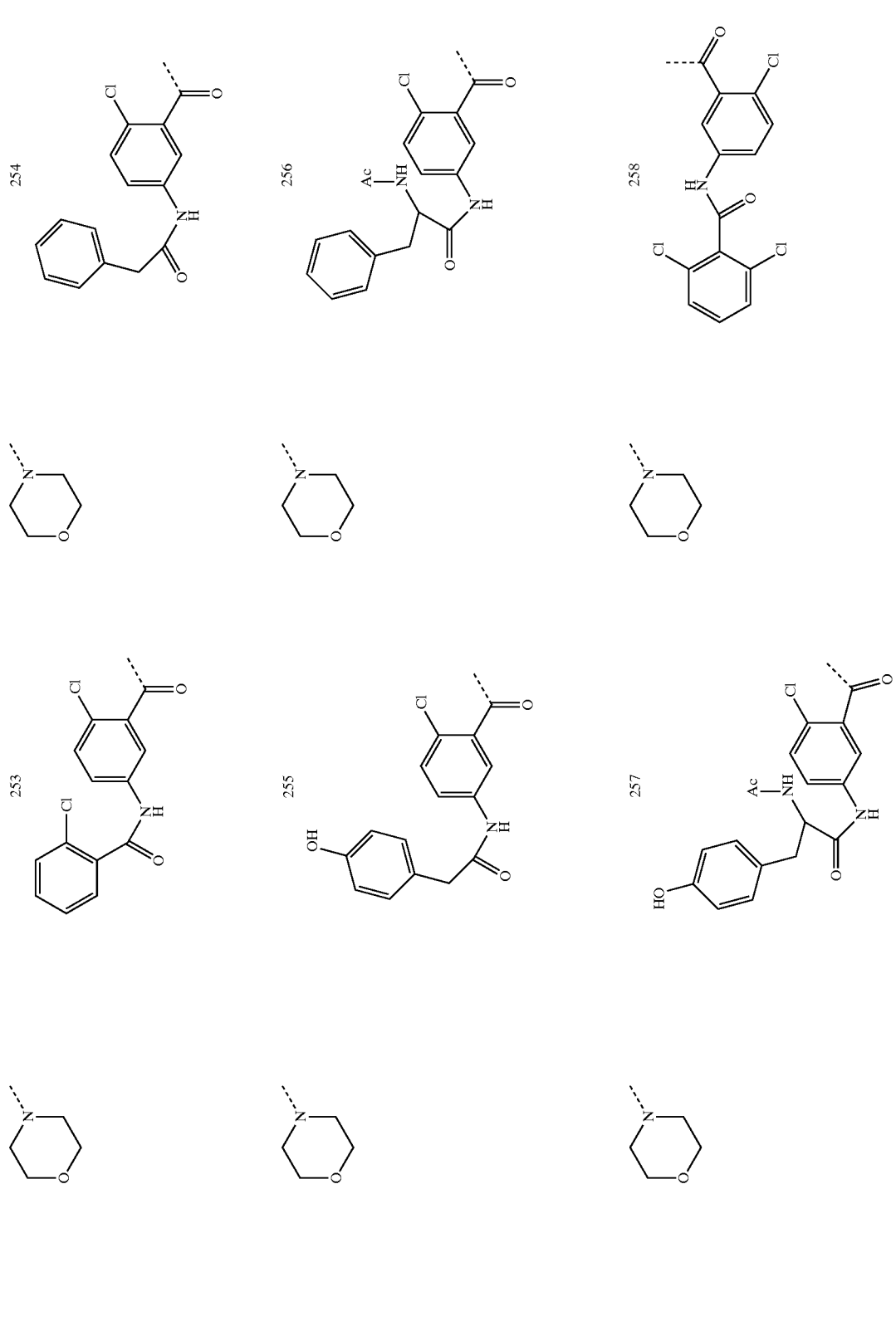

TABLE 2-continued

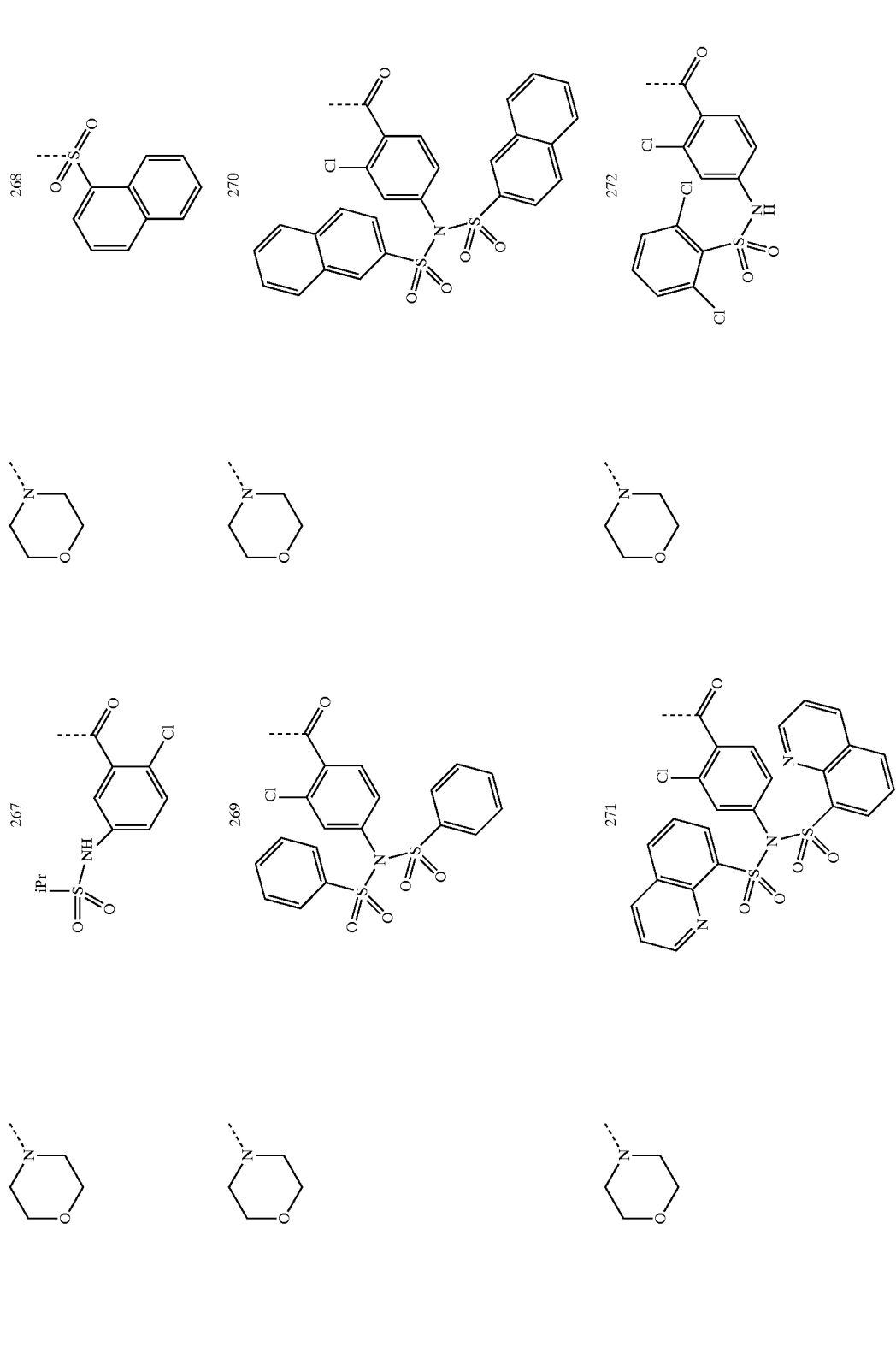

TABLE 2-continued

TABLE 2-continued
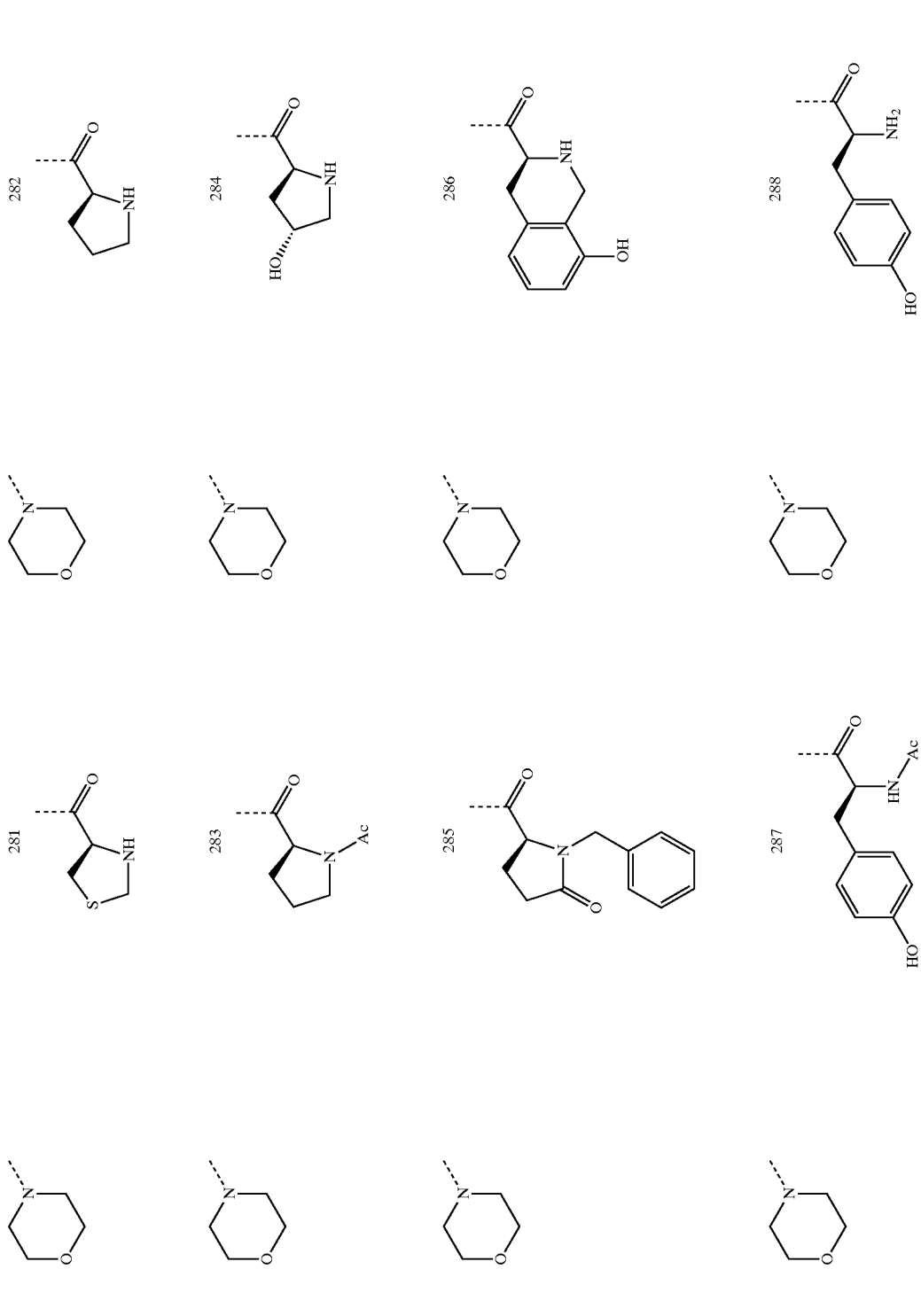

TABLE 2-continued
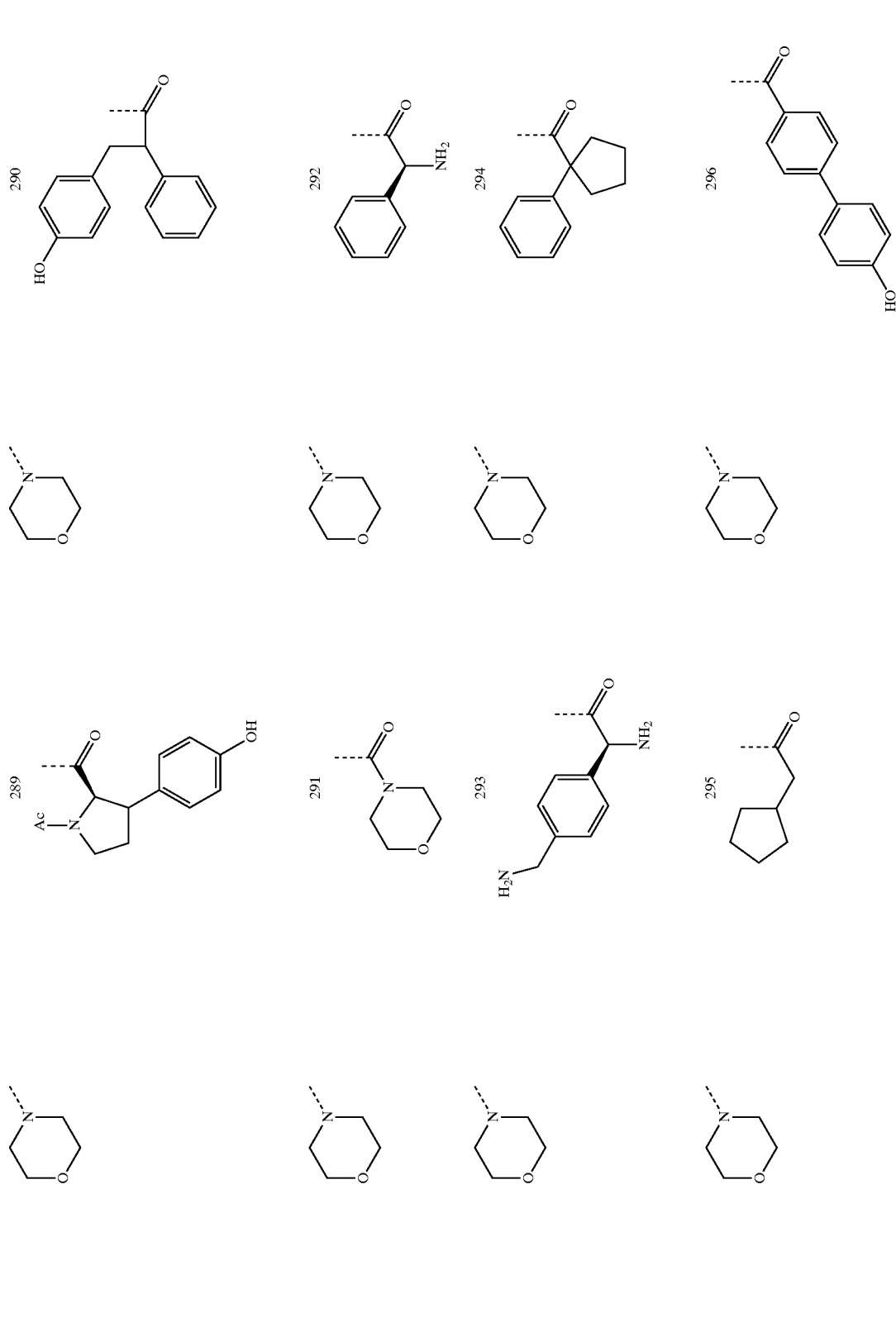

TABLE 2-continued

TABLE 2-continued
| | | | |
|---|---|---|---|
| 305 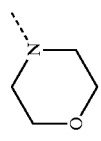 | 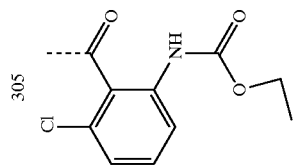 | 306 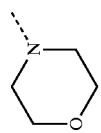 | 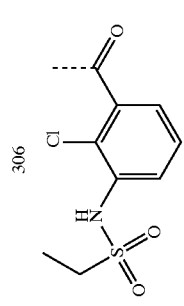 |
| 307 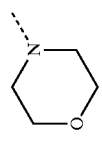 | 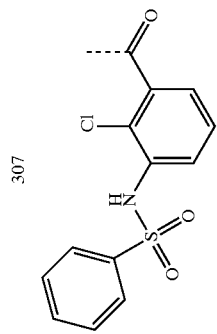 | 308 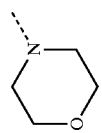 | 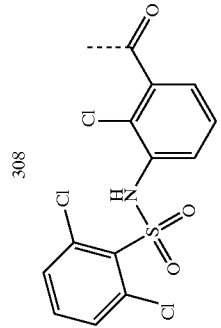 |
| 309 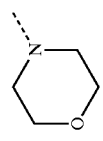 | 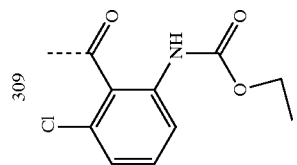 | 310 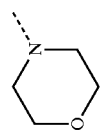 | 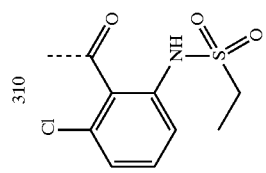 |

TABLE 2-continued

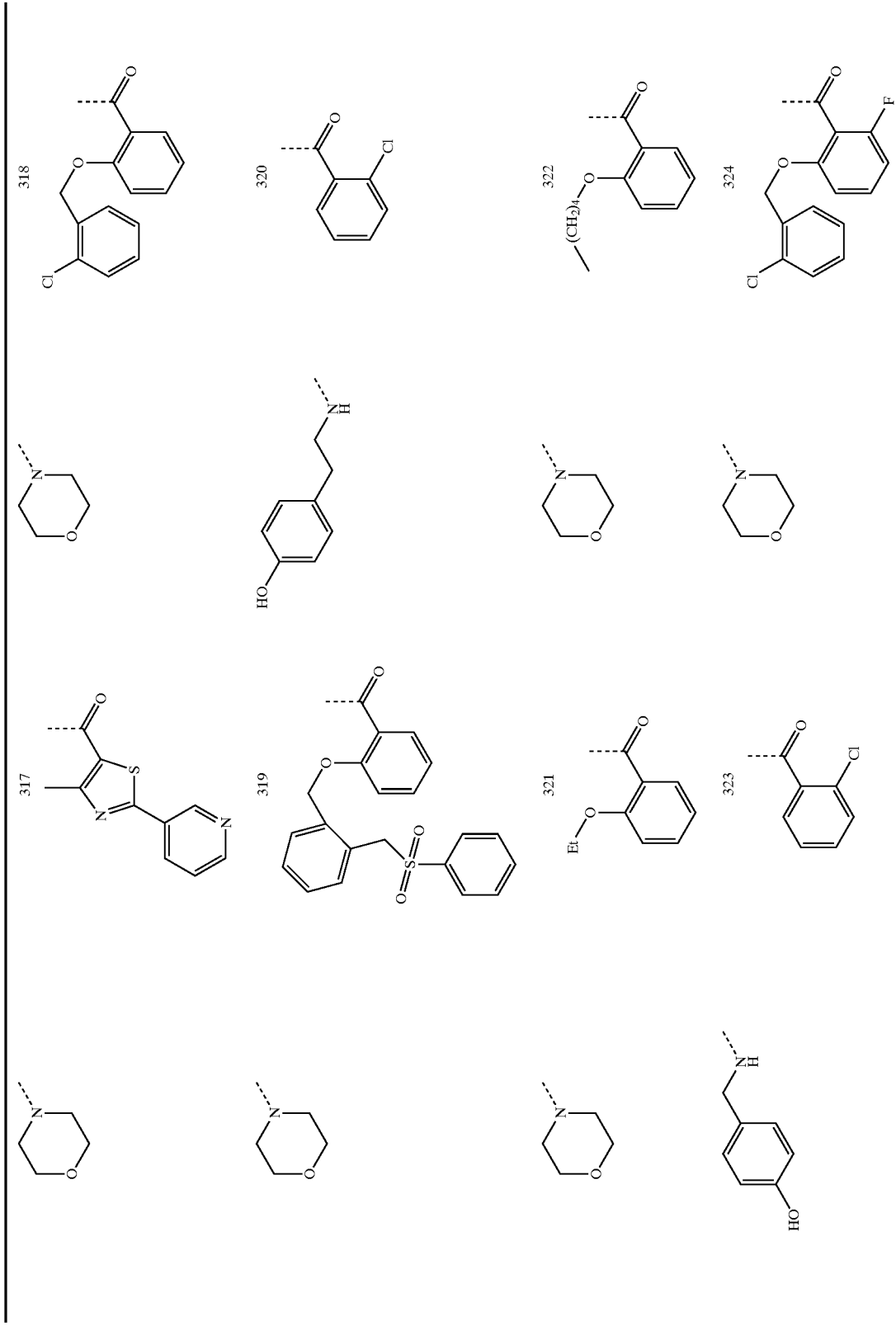

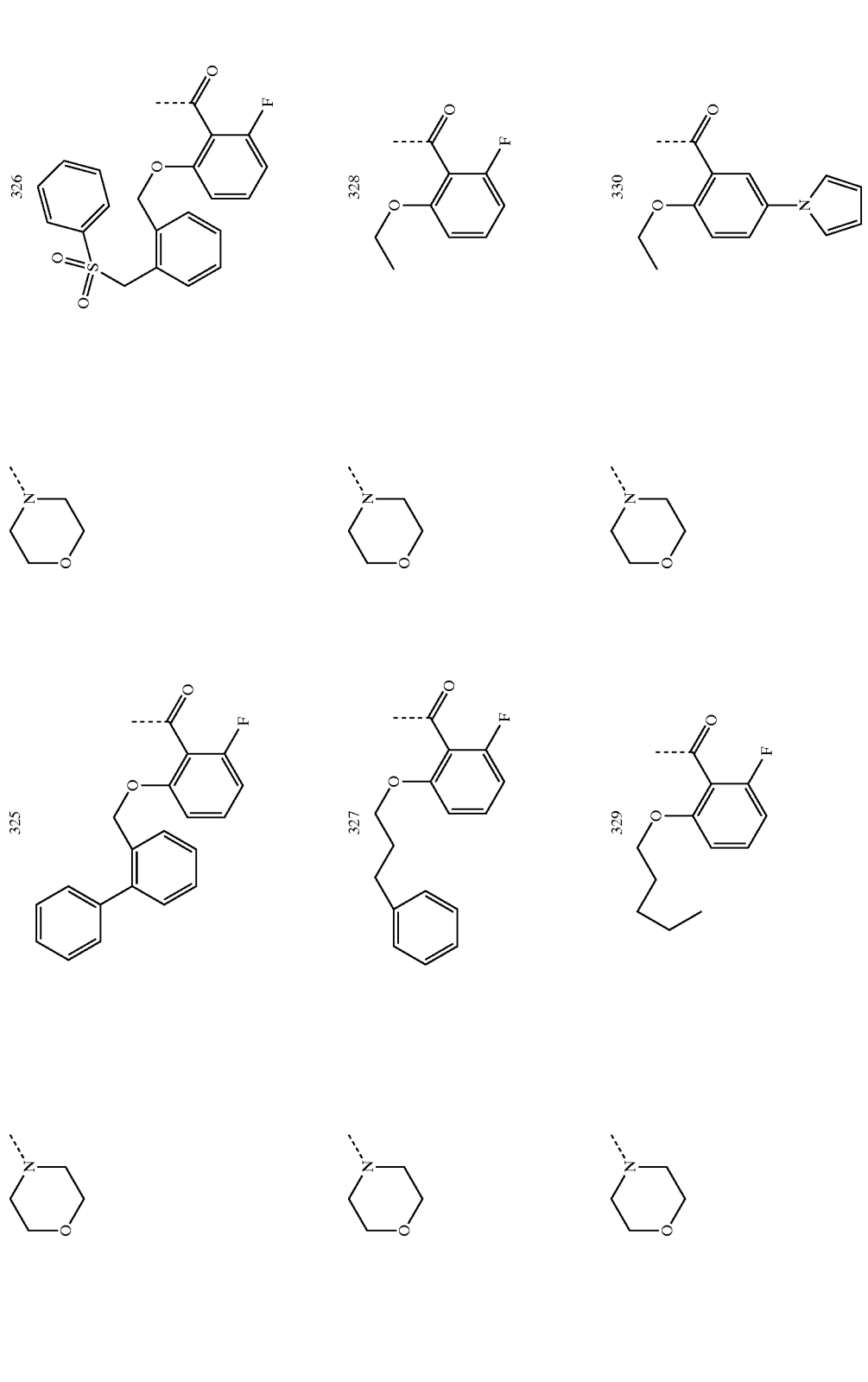

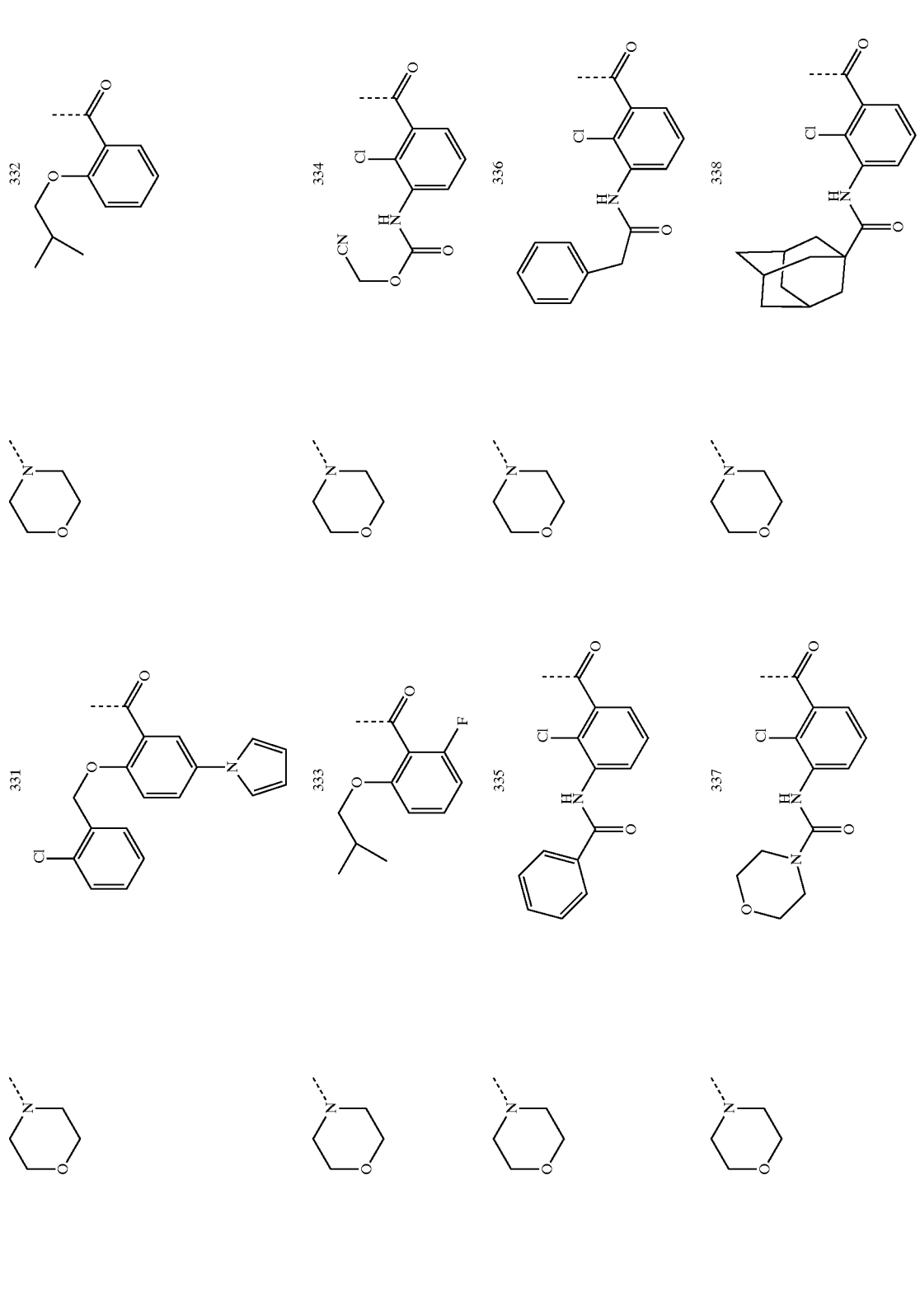

TABLE 2-continued
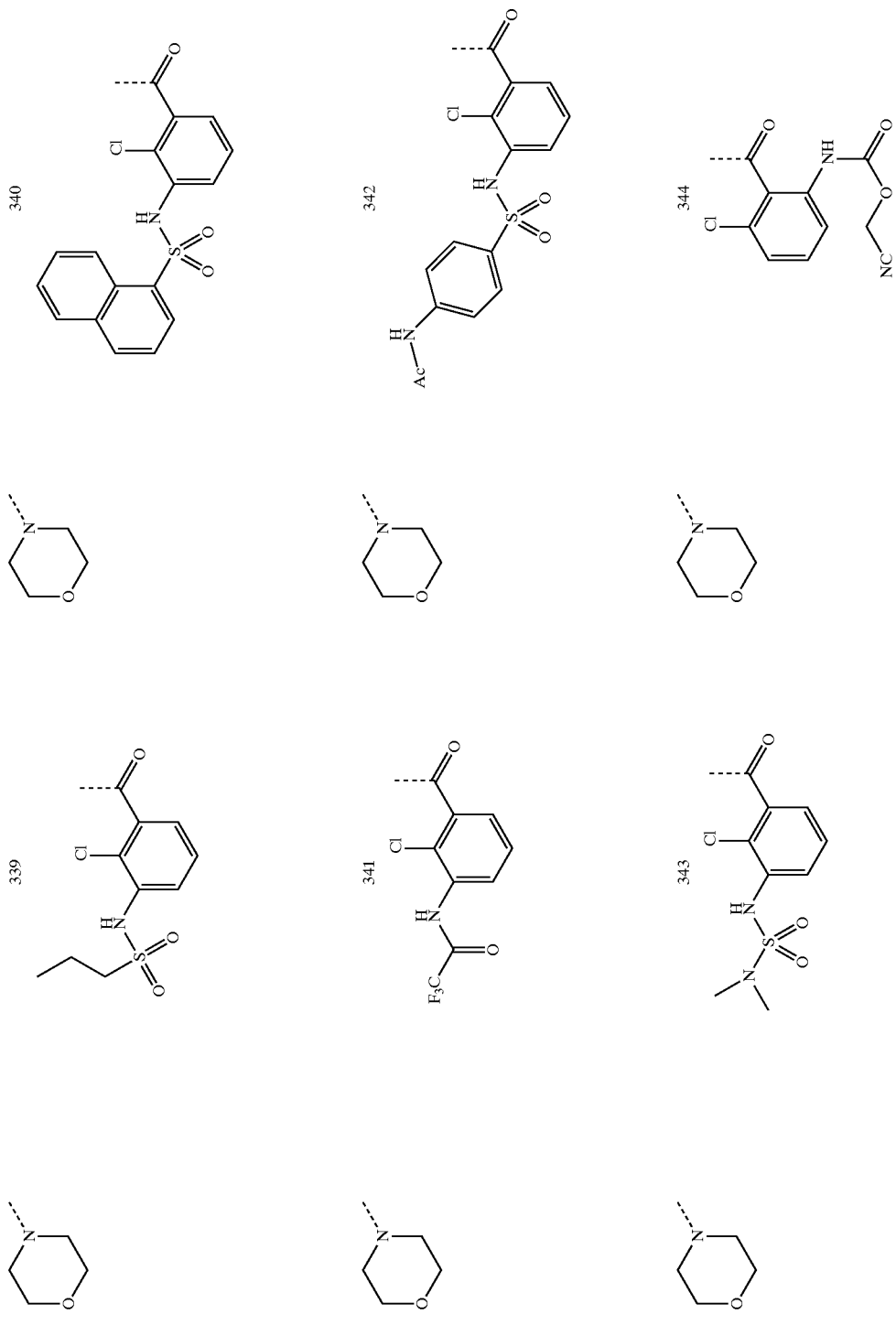

TABLE 2-continued
| | | |
|---|---|---|
| 345 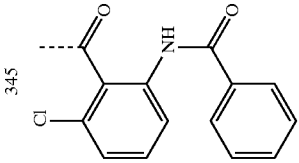 | 347 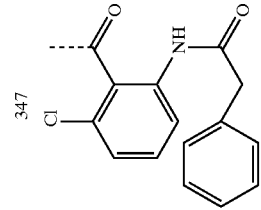 | 349 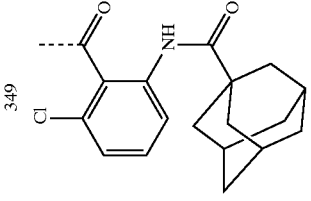 |
| 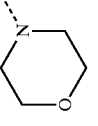 | 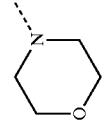 | 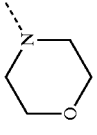 |
| 346 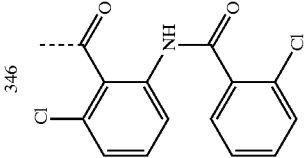 | 348 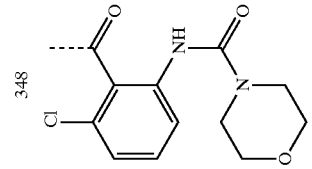 | 350 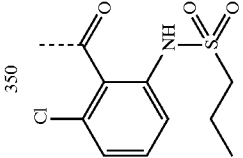 |

TABLE 2-continued
351 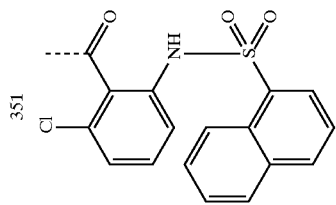 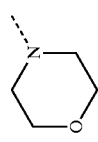
352 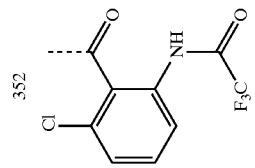 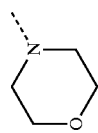
353 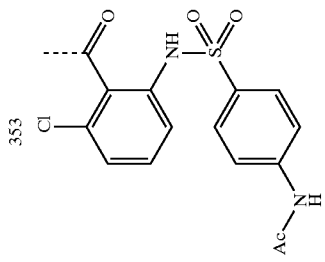 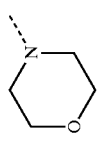
354 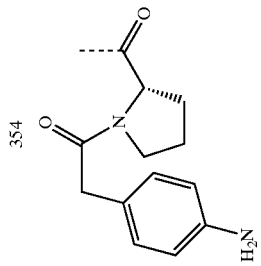 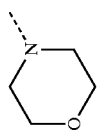

TABLE 2-continued
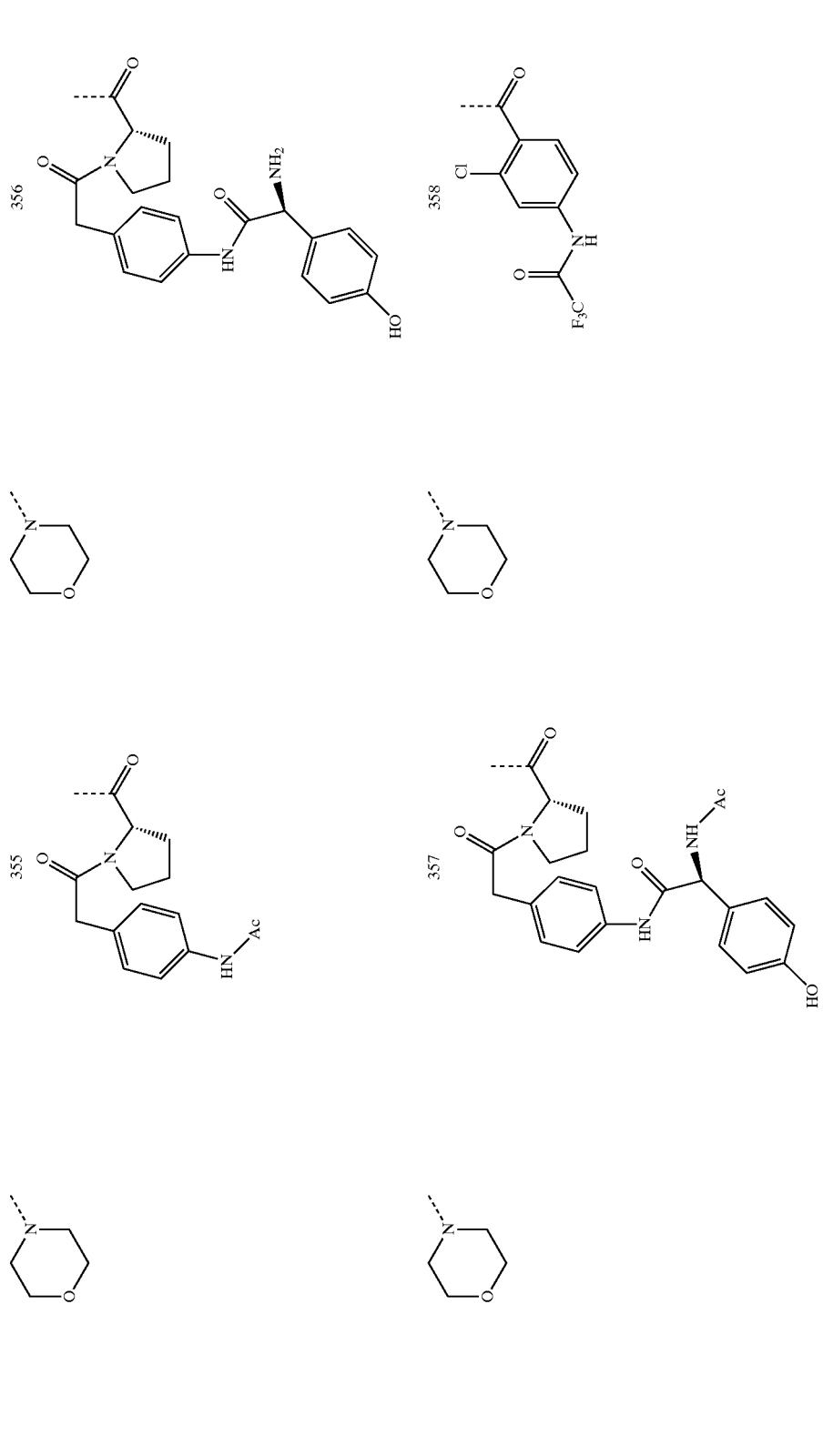

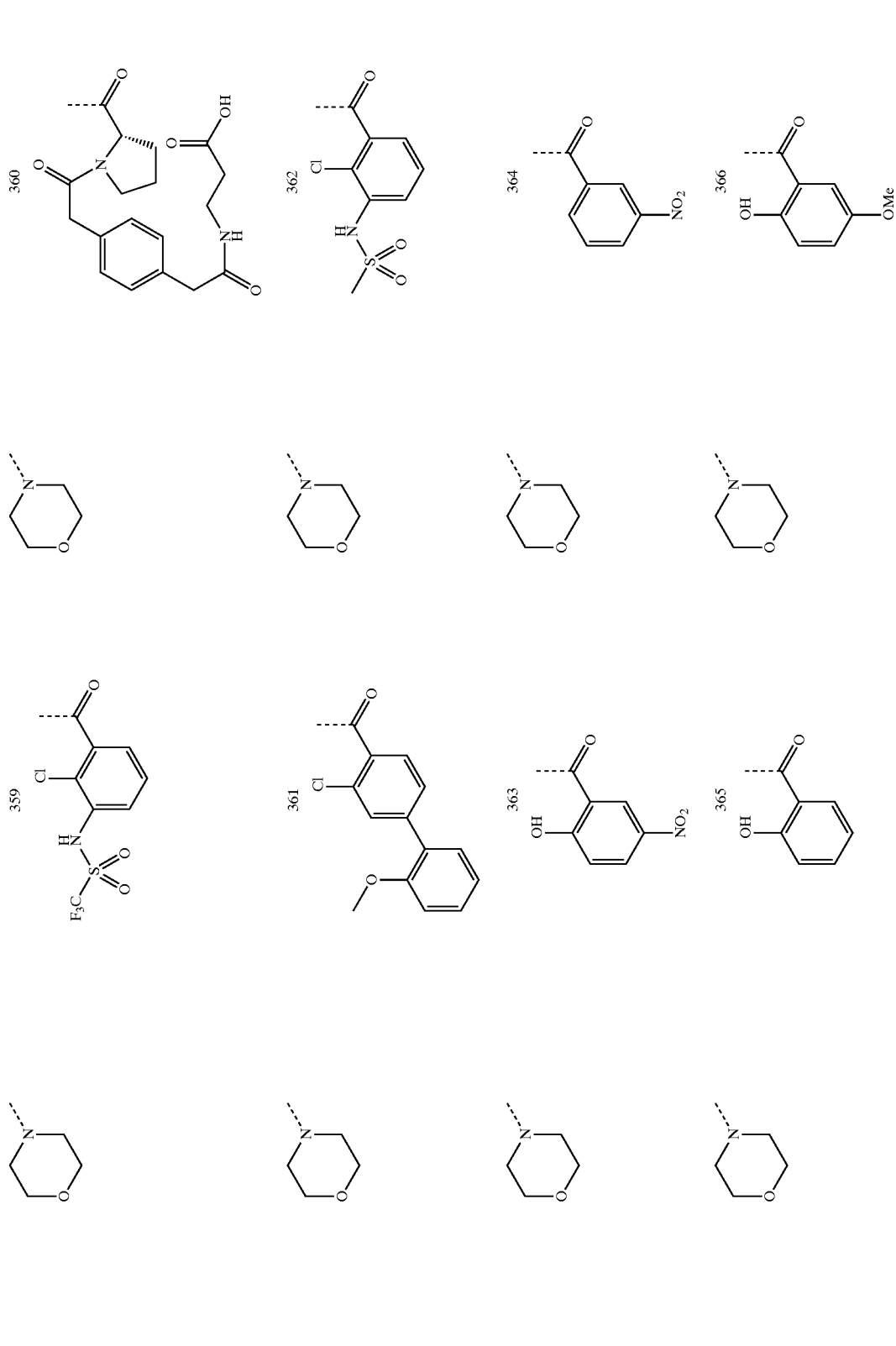

TABLE 2-continued
| 367 | | 368 | |
|---|---|---|---|
| 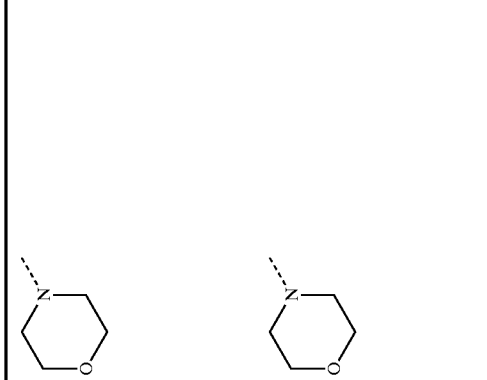 | 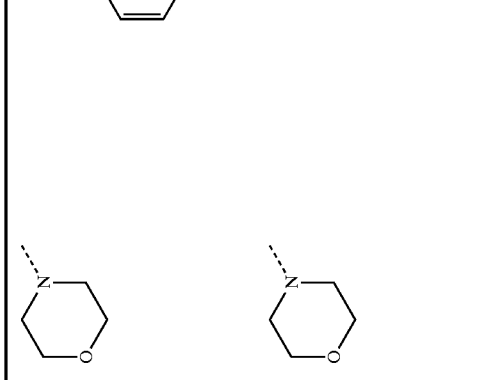 | 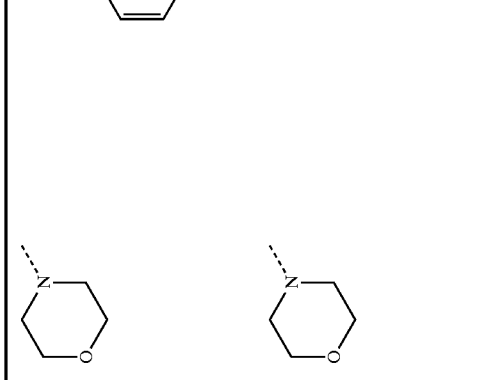 | 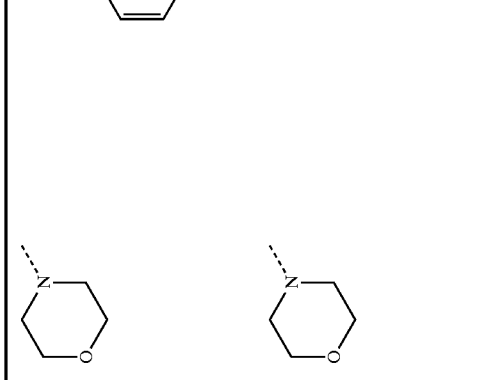 |
| 369 | | 370 | |
|  | 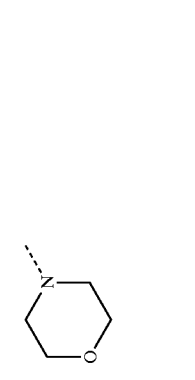 | 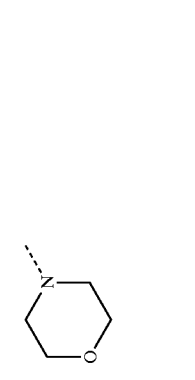 | 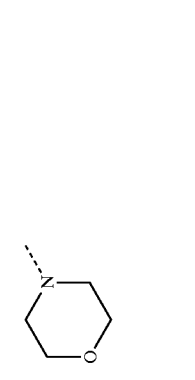 |
| 371 | | 372 | |
|  |  |  |  |
| 373 | | 374 | |
| 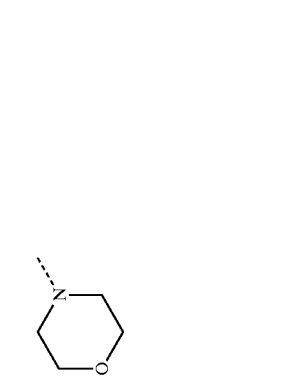 | 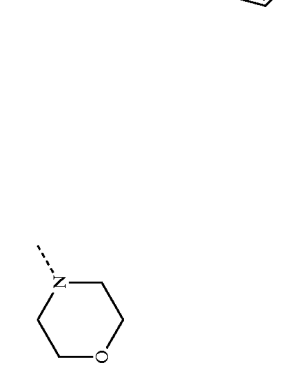 | 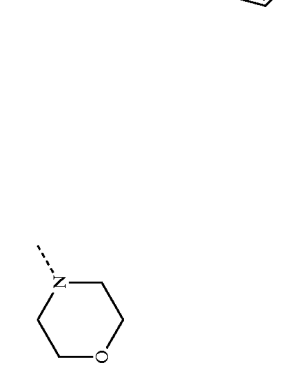 | 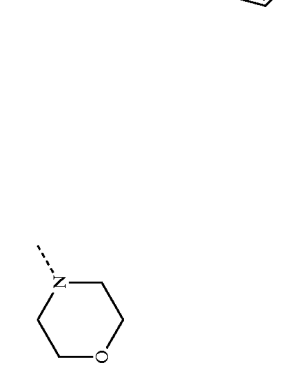 |

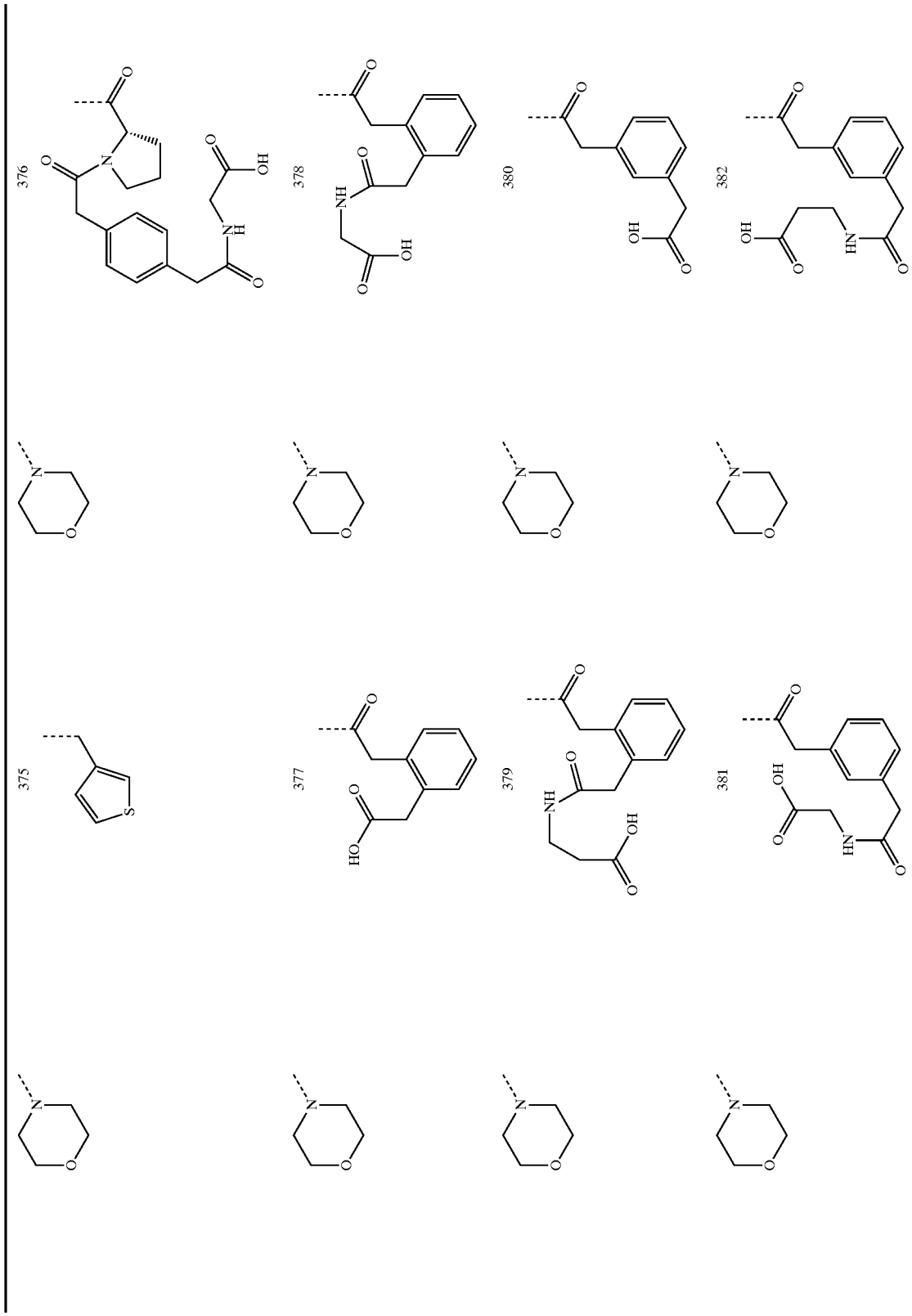

TABLE 2-continued

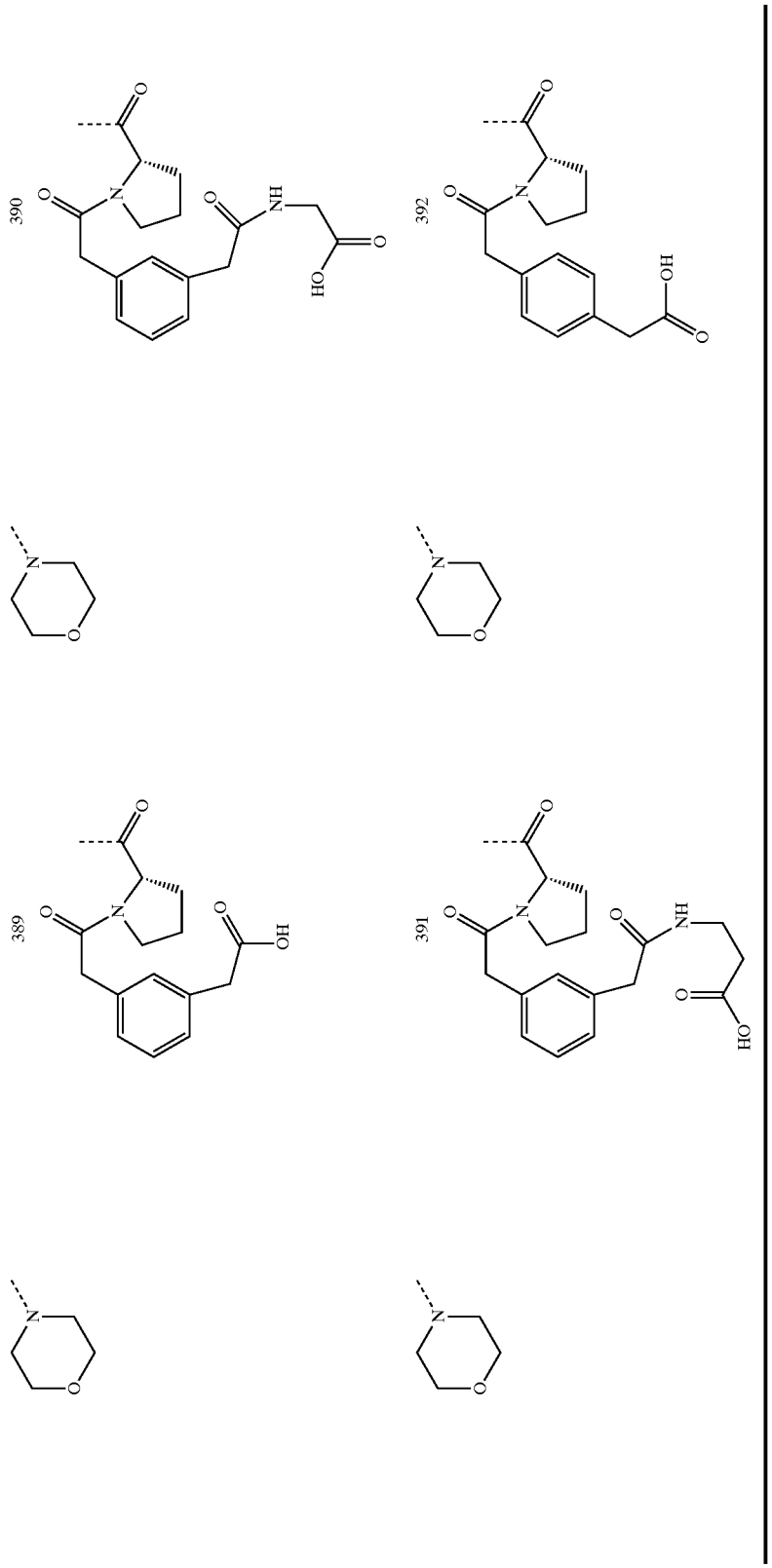

The following table illustrates further compounds prepared and assayed, each of which was found to inhibit binding activity exhibiting an $IC_{50}$ value greater than 1.0 micromolar using the methods described above.
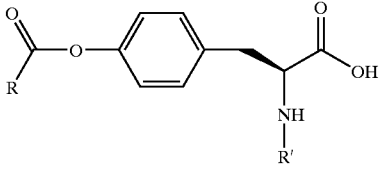
| R | R' |
|---|---|
| 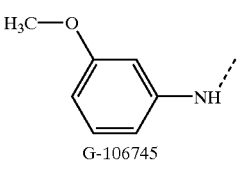 G-106745 | 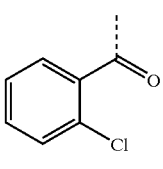 |
| 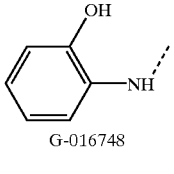 G-016748 | 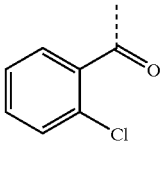 |
| 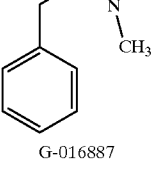 G-016887 | 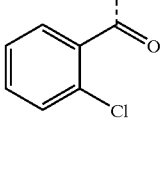 |
| 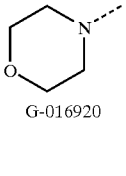 G-016920 | 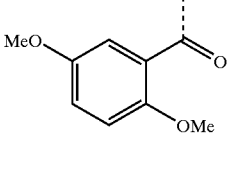 |
| 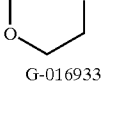 G-016933 | 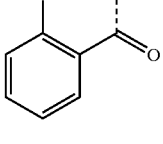 |
| 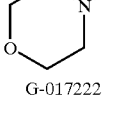 G-017222 | 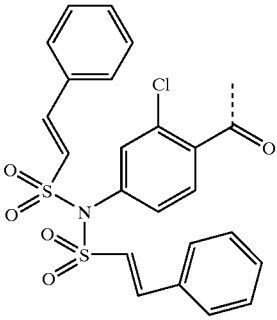 |

-continued
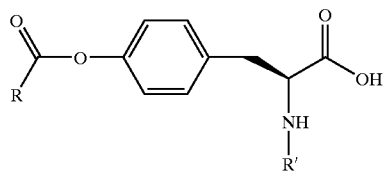
| R | R' |
|---|---|
| 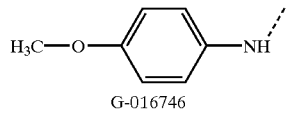 G-016746 | 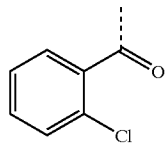 |
| 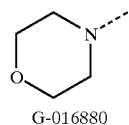 G-016880 |  |
| 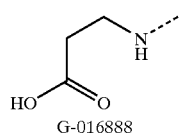 G-016888 | 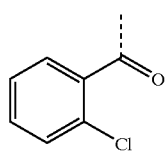 |
| 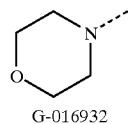 G-016932 | 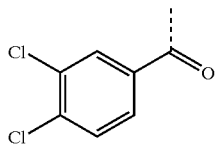 |
| 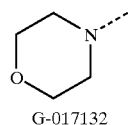 G-017132 | 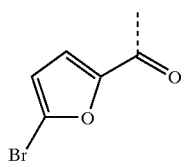 |
| 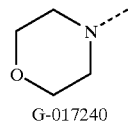 G-017240 | 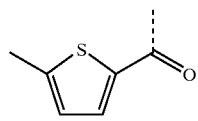 |
| 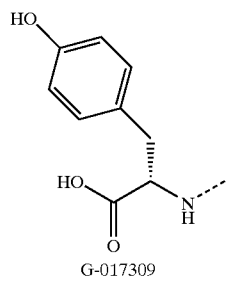 G-017309 | 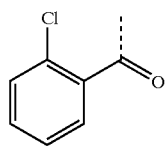 |

-continued
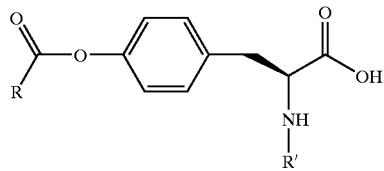
| R | R' |
|---|---|
| 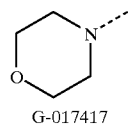<br>G-017417 | 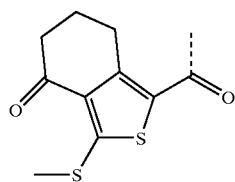 |
| 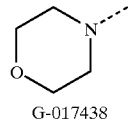<br>G-017438 | 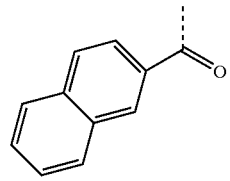 |
| 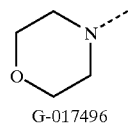<br>G-017496 | 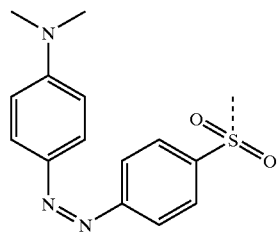 |
| 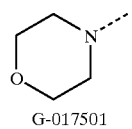<br>G-017501 | 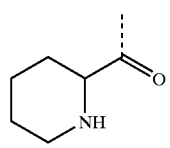 |
| 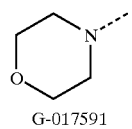<br>G-017591 | 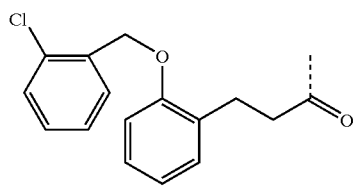 |
| 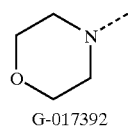<br>G-017392 | 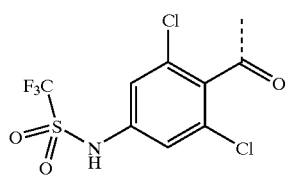 |

-continued
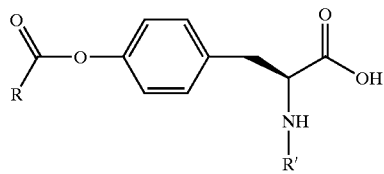
| R | R' |
|---|---|
| 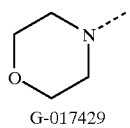<br>G-017429 | HO-C6H4-CH(NH2)-C(=O)- |
| 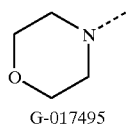<br>G-017495 | 2-(trifluoroacetyl)-1,2,3,4-tetrahydroisoquinolin-7-yl sulfonyl |
| 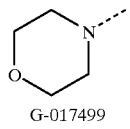<br>G-017499 | 2-(trifluoromethoxy)phenylsulfonyl |
| 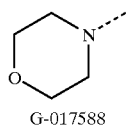<br>G-017588 | 2-(3-phenylpropoxy)benzoyl |
| 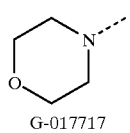<br>G-017717 | 2-((4-(trifluoromethoxy)benzyl)oxy)benzoyl |

What is claimed is:
1. A compound of the formula III:

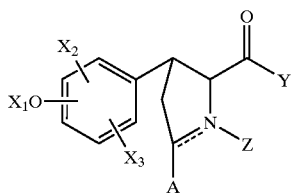

wherein Z is H or lower alkyl; A has the structure:

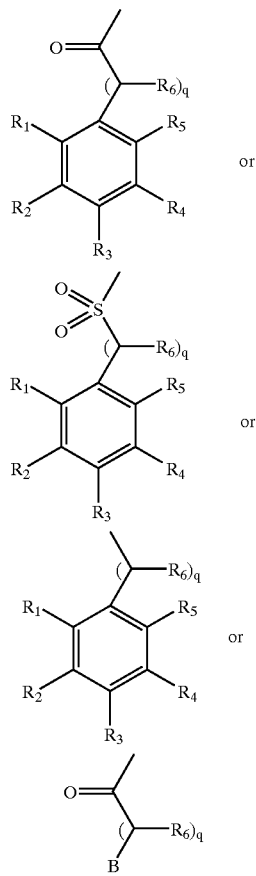

in which
B is cyanoalkyl, a carbocycle or a heterocycle optionally substituted with one or more $R_1$ substituents;
q is 0–3;
$R_1$, $R_2$, $R_3$, $R_4$, $R_5$ and $R_6$ independently are hydrogen, alkyl, amino, alkylamino, dialkylamino, nitro, urea, cyano, thio, alkylthio, hydroxy, alkoxy, alkoxyalkyl, alkoxycarbonyl, alkoxycarbonylamino, aryloxycarbonylamino, alkylsulfinyl, sulfonyl, alkylsulfonyl, aralkylsulfonyl, arylsulfonyl, heteroarylsulfonyl, alkanoyl, alkanoylamino, cycloalkanoylamino, aryl, arylalkyl, halogen, or alkylphosphonyl, and $R_1$, $R_2$, $R_3$, $R_4$ and $R_5$ are substituted with 0–3 substituents selected from the group consisting of hydroxy, carboxyl, lower alkoxycarbonyl, lower alkyl, nitro, oxo, cyano, carbocyclyl, heterocycle, heteroaryl, lower alkylthio, lower alkoxy, lower alkylamino, lower alkanoylamino, lower alkylsulfinyl, lower sulfonyl, lower alkylsulfonyl, lower alkanoyl, aryl, aroyl, heterocyclylcarbonyl, halogen and lower alkylphosphonyl; or two of $R_1$ and $R_5$ together form a carbocycle or heterocyclic ring;
Y is H, alkoxy, alkoxyalkoxy, aryloxy, alkylaminoalkoxy, dialkylaminoalkoxy, alkylamino, arylamino, heterocyclyl or heteroarylalkyl, where each of the forgoing may be substituted or unsubstituted.
$X_1$ is H, C(O)OR, C(O)NRaRb, C(O)R, or C(O)SR wherein R, Ra and Rb, individually, is hydrogen or alkyl, alkoxy, aryl, heterocyclyl, heteroaryl, substituted with 0—4 substituents selected from the group consisting of halogen, hydroxy, amino, carboxyl, nitro, cyano, heterocylyl, heteroaryl, aryl, aroyl, aryloxy, aralkyl, aralkyloxy, aryloxycarbonyl, aralkyloxycarbonyl, alkylenedioxy, lower alkoxycarbonyl, lower alkyl, lower alkenyl, lower alkynyl, lower alkylthio, lower alkoxy, lower alkylamino, lower alkylsulfinyl, lower sulfonyl, lower alkylsulfonyl, lower alkanoyl, lower alkylphosphonyl, aminosulfonyl lower alkyl, hydroxy lower alkyl, alkylsulfinyl lower alkyl, alkylsulfonyl lower alkyl, alkylthio lower alkyl, heteroarylthio lower alkyl, heteroaryloxy lower alkyl, heteroarylamino lower alkyl, halo lower alkyl, and alkoxy lower alkyl; wherein said heterocyclyl, heteroaryl, aryl, aroyl, aryloxy, aralkyl, aralkyloxy, aryloxycarbonyl and aralkyloxycarbonyl is optionally substituted with halogen, hydroxyl, amino, carboxyl, nitro, cyano, alkyl and alkoxy; and wherein Ra and Rb together with the nitrogen to which they are attached may form a heterocyclyl or heteroaryl group substituted with 0–5 substituents R or Rd; wherein Rd has the structure

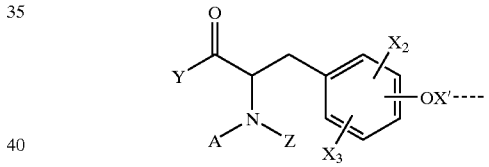

wherein X' is a divalent linker selected from the group consisting of C(O)NRa, C(O) or a bond;
$X_2$ and $X_3$ are each independently hydrogen, halogen, hydroxy, amino, carboxyl, nitro, cyano, or substituted or unsubstituted alkyl, aryl, heterocylyl, heteroaryl, aryl, aroyl, aryloxy, alkylenedioxy, lower alkyl carbonylamino, lower alkenyl carbonylamino, aryl carbonylamino, arylalkyl carbonylamino, lower alkoxy carbonylamino, lower alkylamino carbonylamino, arylamino carbonylamino, lower alkoxycarbonyl, lower alkyl, lower alkenyl, loweralkynyl, lower alkylthio, lower alkoxy, lower alkylamino, lower alkylsulfinyl, lower sulfonyl, lower alkylsulfonyl, lower alkanoyl, lower alkylphosphonyl, aminosulfonyl lower alkyl, hydroxy lower alkyl, alkylsulfinyl lower alkyl, alkylsulfonyl lower alkyl, alkylthio lower alkyl, heteroarylthio lower alkyl, heteroaryloxy lower alkyl, heteroarylamino lower alkyl, halo lower alkyl, alkoxy lower alkyl; and wherein $X_1$ and $X_2$ or $X_3$ may be bonded together to form a heterocylic or heteroaryl ring(s); or $X_3$ and Z together form a heterobicyclic ring;
or a pharmaceutically acceptable salt thereof.
2. The compound of claim 1, wherein $X_1$ is C(O)OR, C(O)R, or C(O)SR.
3. The compound of claim 1, wherein $X_1$ is C(O)NRaRb.

4. The compound of claim 1, wherein $X_1$ is C(O)NRaRb and wherein Ra and Rb together with the nitrogen to which they are attached form a 5-membered or 6-membered heterocyclyl or heteroaryl group substituted with 0–4 substituents R.

5. The compound of claim 4, wherein said heterocyclyl or heteroaryl group is a member selected from the group consisting of

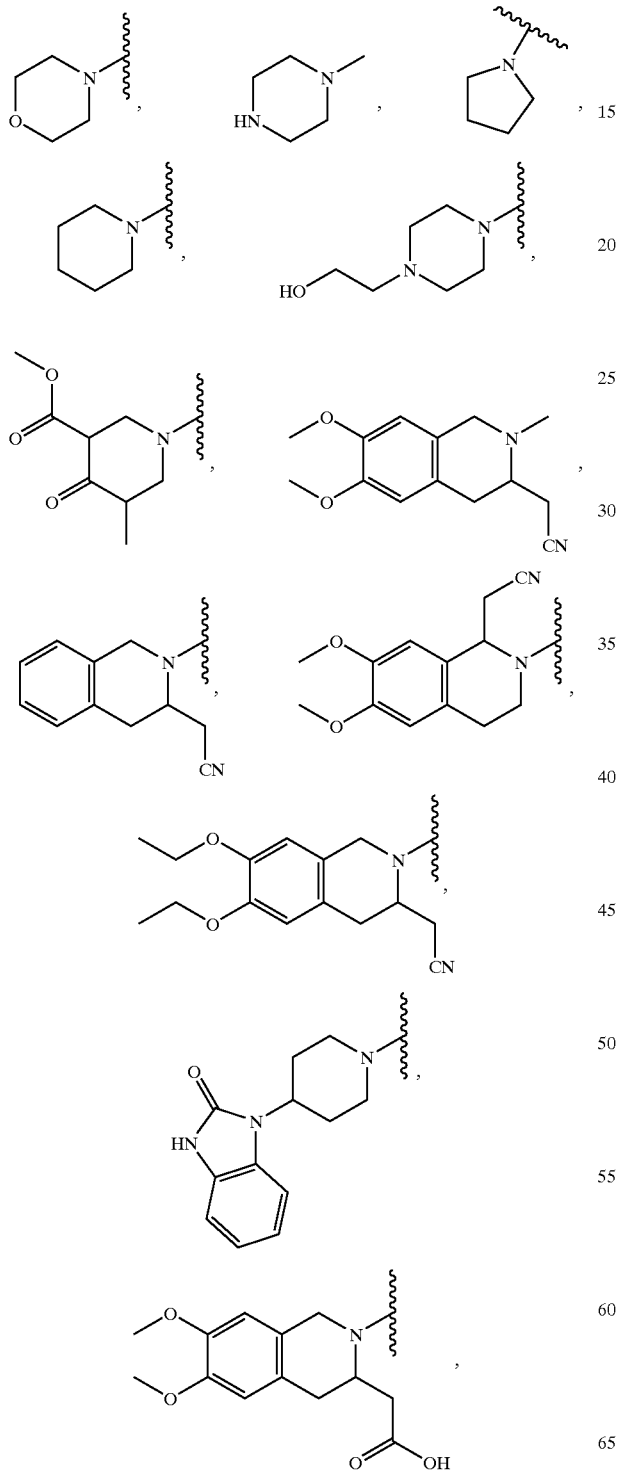

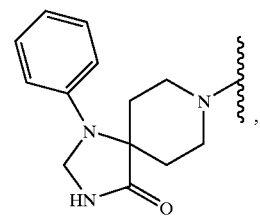

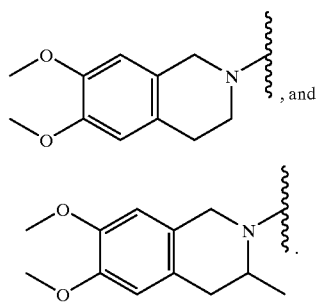, and

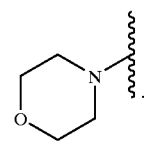

6. The compound of claim 5, wherein said heterocyclyl or heteroaryl group is

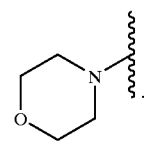

7. The compound of claim 3, wherein $X_1$ is C(O)NRaRb and wherein Ra and Rb are independently hydrogen, substituted or unsubstituted alkyl, aryl heterocyclyl, or heteroaryl.

8. The compound of claim 6, wherein $X_1$ is C(O)R and R is a member selected from the group consisting of

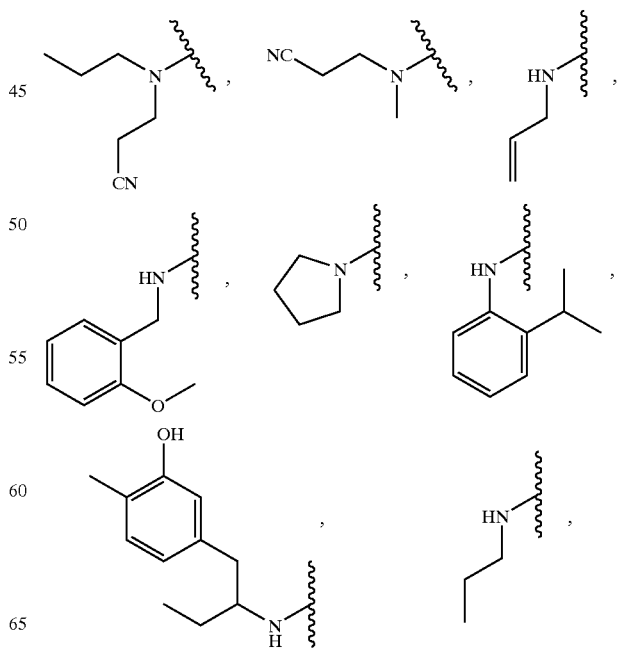

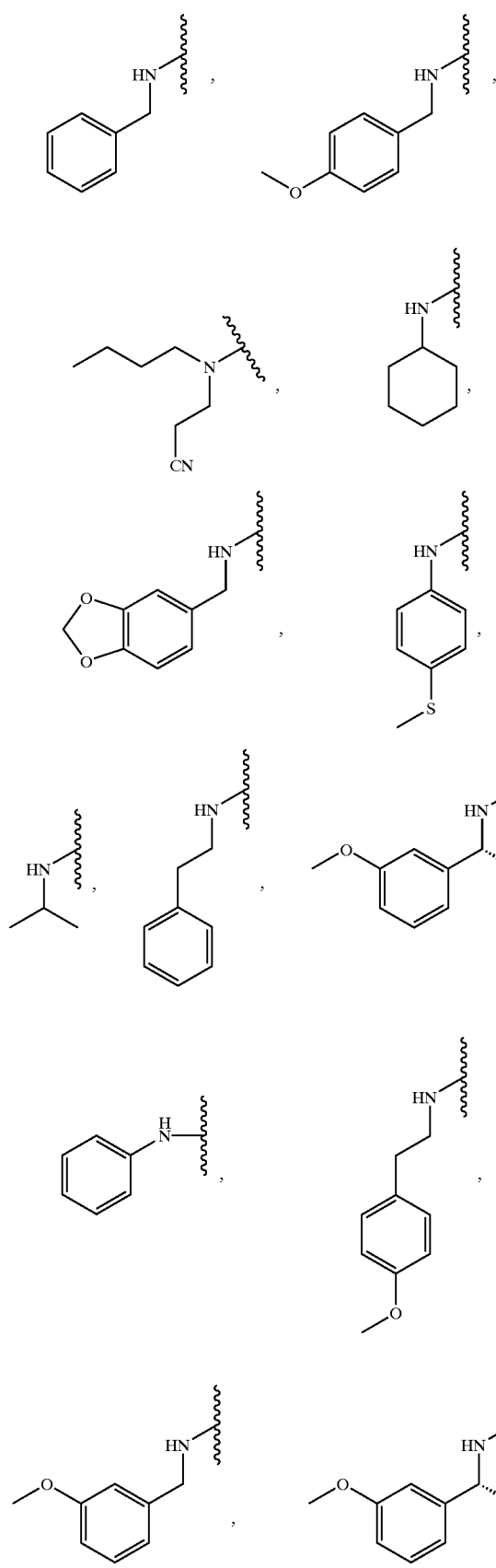
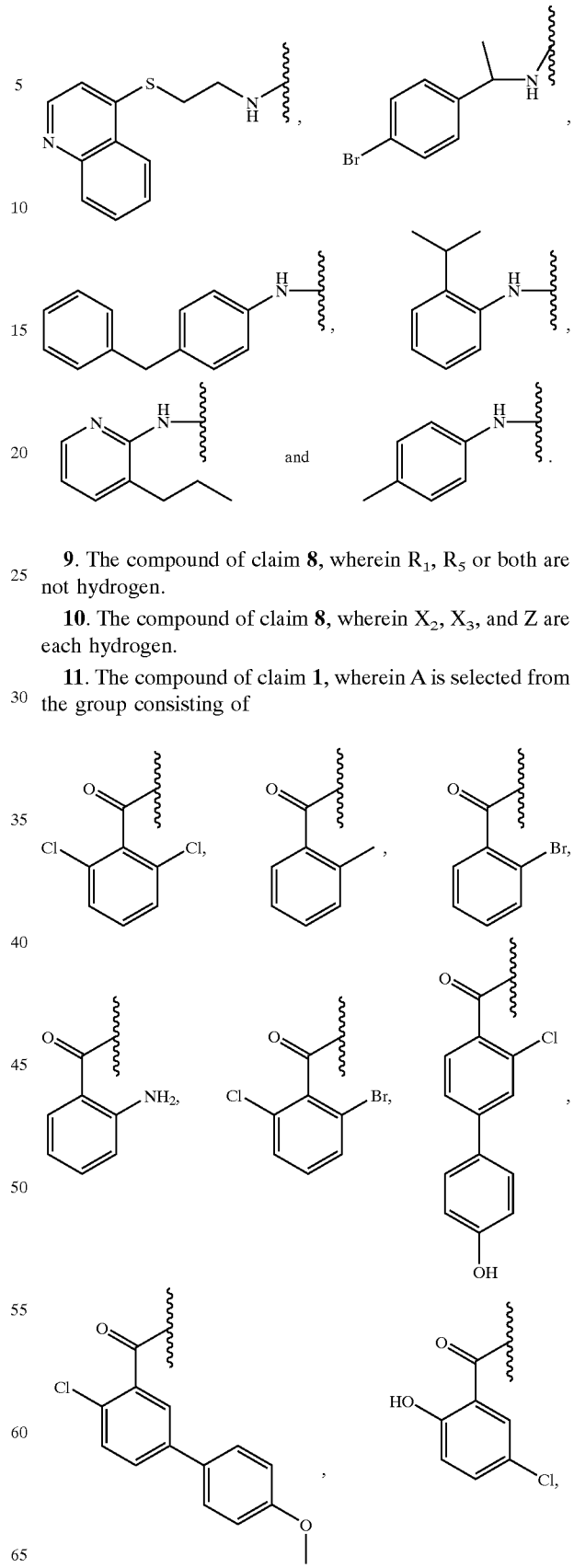
9. The compound of claim 8, wherein $R_1$, $R_5$ or both are not hydrogen.
10. The compound of claim 8, wherein $X_2$, $X_3$, and Z are each hydrogen.
11. The compound of claim 1, wherein A is selected from the group consisting of -continued

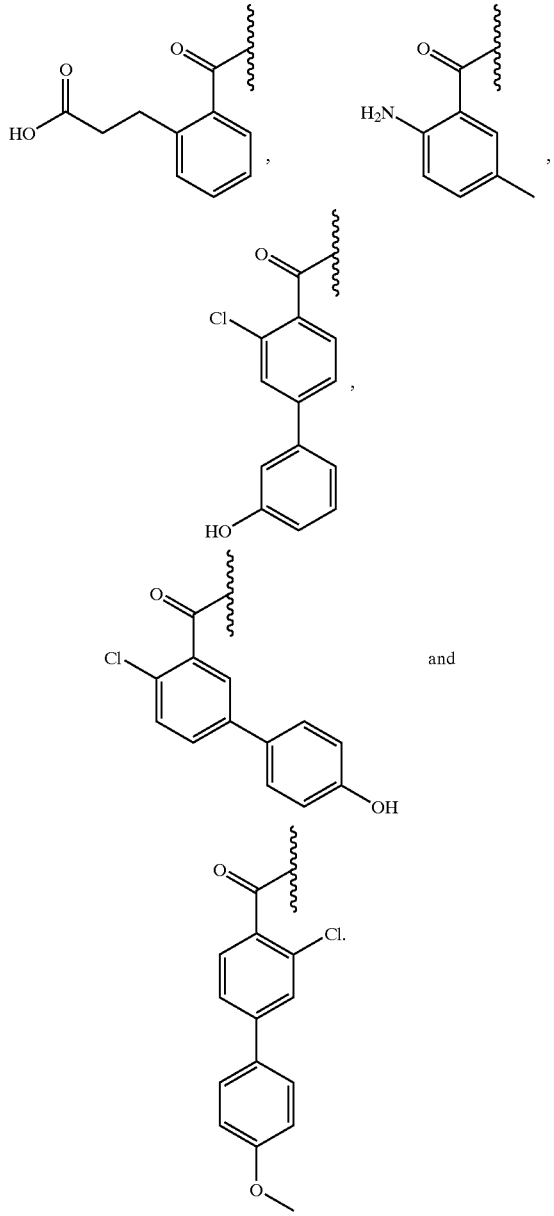

12. The compound of claim 1, wherein A is

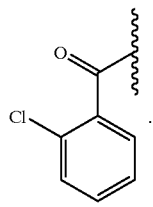

13. The compound of claim 1, wherein $X_2$ is a member selected from the group consisting of

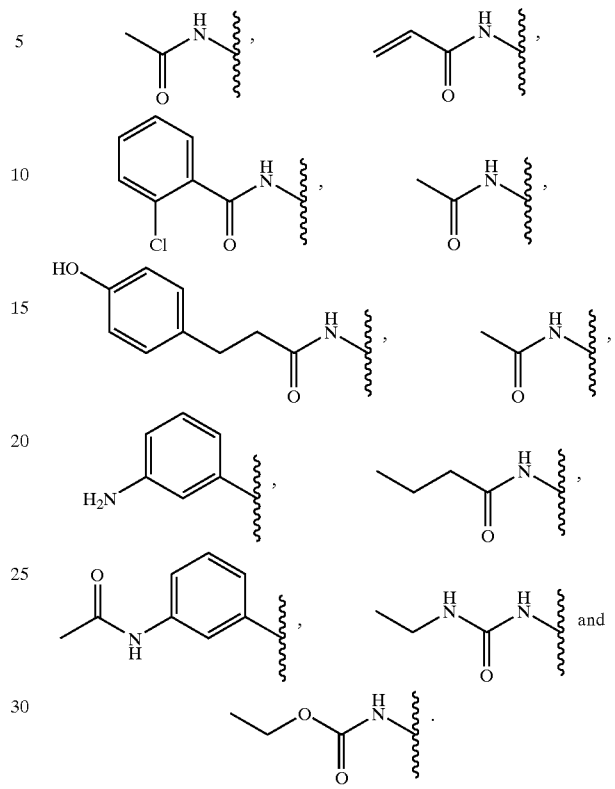

14. The compound of claim 1, wherein the compound has S stereochemical configuration.

15. A composition, comprising the compound of claim 1 and a carrier or excipient.

16. A pharmaceutical composition comprising the compound of claim 1 and a therapeutically inert carrier or excipient.

17. A method for treating a disease or condition associated with binding or alpha4beta7 to MAdCAM-1 or alpha4beta1 to VCAM-1, comprising administering an effective amount of the compound of claim 1 to a mammal in need thereof.

18. A method for treating rheumatoid arthritis, asthma, psoriasis, multiple sclerosis, inflammatory bowel disease, ulcerative colitis, pouchitis, Chron's disease, Celiac disease, nontropical Sprue, graft-versus-host disease, pancreatitis, insulin-dependent diabetes mellitus, masritis, cholecystitis, pericholangitis, chronic sinusitis, chronic bronchitis, pneumonitis, collagen disease, eczema or systemic lupus erythematosis, comprising administering an effective amount of the compound of claim 1 to a mammal in need thereof.

* * * * *

UNITED STATES PATENT AND TRADEMARK OFFICE
CERTIFICATE OF CORRECTION

PATENT NO.      : 6,469,047 B1                                    Page 1 of 1
DATED           : October 22, 2002
INVENTOR(S)     : Jackson, David Y. et al.

It is certified that error appears in the above-identified patent and that said Letters Patent is hereby corrected as shown below:

Column 171,
Line 66, please delete "heterocycle," and insert -- heterocyclyl --;

Column 172,
Line 3, please delete "and" and insert -- to --;
Line 53, please delete "loweralkynyl," and insert -- lower alkynyl --; and Column 178,
Line 53, please delete "masritis," and insert -- mastitis --.

Signed and Sealed this

Twenty-fifth Day of February, 2003

JAMES E. ROGAN
*Director of the United States Patent and Trademark Office*